(12) United States Patent
Shipp et al.

(10) Patent No.: US 9,840,708 B2
(45) Date of Patent: Dec. 12, 2017

(54) COMPOSITIONS AND METHODS FOR THE MODULATION OF DNA DAMAGE RESPONSES USING BAL1 AND BBAP

(71) Applicant: Dana-Farber Cancer Institute, Inc., Boston, MA (US)

(72) Inventors: Margaret A. Shipp, Wellesley, MA (US); Qingsheng Yan, Wayland, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/350,166

(22) PCT Filed: Oct. 5, 2012

(86) PCT No.: PCT/US2012/058960
§ 371 (c)(1),
(2) Date: Apr. 7, 2014

(87) PCT Pub. No.: WO2013/052800
PCT Pub. Date: Apr. 11, 2013

(65) Prior Publication Data
US 2015/0020221 A1 Jan. 15, 2015

Related U.S. Application Data

(60) Provisional application No. 61/543,465, filed on Oct. 5, 2011.

(51) Int. Cl.
| | | |
|---|---|---|
| *C12N 15/113* | (2010.01) | |
| *C12N 15/85* | (2006.01) | |
| *C12Q 1/68* | (2006.01) | |
| *G01N 33/574* | (2006.01) | |
| *C07K 16/40* | (2006.01) | |
| *C12N 9/10* | (2006.01) | |
| *C12N 9/00* | (2006.01) | |
| *C12Q 1/25* | (2006.01) | |
| *C12Q 1/48* | (2006.01) | |
| *G01N 33/573* | (2006.01) | |

(52) U.S. Cl.
CPC ......... *C12N 15/1137* (2013.01); *C07K 16/40* (2013.01); *C12N 9/1077* (2013.01); *C12N 9/93* (2013.01); *C12N 15/8509* (2013.01); *C12Q 1/25* (2013.01); *C12Q 1/48* (2013.01); *C12Q 1/6886* (2013.01); *C12Y 603/02019* (2013.01); *G01N 33/573* (2013.01); *G01N 33/57484* (2013.01); *C12N 2015/859* (2013.01); *C12N 2310/11* (2013.01); *C12N 2310/14* (2013.01); *C12N 2310/16* (2013.01); *C12N 2320/30* (2013.01); *C12N 2320/31* (2013.01); *C12Q 2600/158* (2013.01); *C12Y 204/0203* (2013.01); *C12Y 603/02* (2013.01); *G01N 2333/9015* (2013.01); *G01N 2333/91142* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,852,318 B1 * | 2/2005 | Varner ................... | A61K 38/08 424/130.1 |
| 2004/0197328 A1 * | 10/2004 | Young .............. | A61K 47/48569 424/141.1 |
| 2005/0014186 A1 * | 1/2005 | Shipp .................... | C07K 14/47 435/6.16 |
| 2011/0097329 A1 * | 4/2011 | Chang .................. | C12N 15/113 424/137.1 |

OTHER PUBLICATIONS

Juszczynski et al. (Mol. Cell. Biol. Jul. 2006 26(14): 5348-5359).*
Eisenhauer et al. (European J. Cancer 2009, 45: 228-247).*
Gura (Science, 1997, 278:1041-1042).*
Kaiser (Science, 2006, 313: 1370).*
Gura (Science, 1995, 270:575-577).*
Vyas and Chang (Nature Reviews Cancer, Jul. 2014 14: 502-509).*
Wahlberg et al. (Nature Biotechnology Mar. 2012 30(3): 283-288) t.*
Gerdes et al. (Front. Oncol. Dec. 18, 2014 doi: 10.3389/fonc.2014. 00366, pp. 1-12).*
The National Cancer Institute (Lymphoma-Patient Version http:// www.cancer.gov/types/lymphoma downloaded Dec. 17, 2015).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Aguiar et al., "BAL is a novel risk-related gene in diffuse large B-cell lymphomas that enhances cellular migration," Blood, 96(13):4328-4334 (2000).
Takeyama et al., "The BAL-binding Protein BBAP and Related Deltex Family Members Exhibit Ubiquitin-Protein Isopeptide Ligase Activity," J. Biol. Chem., 278(24):21930-21937 (2003).
Yan et al., "BBAP Monoubiquitylates Histone H4 at Lysine 91 and Selectively Modulates the DNA Damage Response," Molecular Cell, 36:110-120 (2009).

* cited by examiner

*Primary Examiner* — Peter J Reddig
(74) *Attorney, Agent, or Firm* — Foley Hoag LLP

(57) ABSTRACT

The invention provides methods and compositions for enhancing the efficacy of cancer therapies through modulation of BAL1 and/or BBAP. Also provided are methods for predicting the efficacy of cancer therapies or treating cancer in a subject through modulation of BAL1 and/or BBAP. Further provided are methods for identifying compounds that are capable of modulating BAL1-BBAP complexes.

13 Claims, 19 Drawing Sheets

\* Inactive in BAL1

SEQUENCE LISTING

```
<160> NUMBER OF SEQ ID NOS: 55

<210> SEQ ID NO 1
<211> LENGTH: 2565
<212> TYPE: DNA
<213> ORGANISM: Homo sapiens
```

<400> SEQUENCE: 1

```
atggactttt ccatggtggc cggagcagca gcttacaatg aaaaatcagg taggattacc    60
tcgctctcac tcttgtttca gaaagtcttt gctcagatct ttcctcagtg gagaaagggg   120
aatacagaag aatgtctccc ctacaagtgc tcagagactg gtgctcttgg agaaaactat   180
agttggcaaa ttcccattaa ccacaatgac ttcaaaattt taaaaaataa tgagcgtcag   240
ctgtgtgaag tcctccagaa taagtttggc tgtatctcta ccctggtctc tccagttcag   300
gaaggcaaca gcaaatctct gcaagtgttc agaaaaatgc tgactcctag gatagagtta   360
tcagtctgga agatgacctc accacacat gctgttgatg ctgtggtgaa tgcagccaat   420
gaagatcttc tgcatggggg aggcctggcc ctggccctgg taaaagctgg tggatttgaa   480
atccaagaag agagcaaaca gtttgttgcc agatatggta agtgtcagc tggtgagata   540
gctgtcacgg gagcagggag gcttccctgc aaacagatca tccatgctgt tgggcctcgg   600
tggatggaat gggataaaca gggatgtact ggaaagctgc agagggccat tgtaagtatt   660
ctgaattatg tcatctataa aaatactcac attaagacag tagcaattcc agccttgagc   720
tctgggattt ttcagttccc tctgaatttg tgtacaaaga ctattgtaga gactatccgg   780
gttagtttgc aagggaagcc aatgatgagt aatttgaaaa aaattcacct ggtgagcaat   840
gaggaccct ctgttgctgc cttttaaagct gcttcagaat tcatcctagg aagagtgag   900
ctgggacaag aaaccacccc ttctttcaat gcaatggtcg tgaacaacct gaccctccag   960
attgtccagg ccacattga atggcagacg gcagatgtaa ttgttaattc tgtaaaccca  1020
catgatatta cagttggacc tgtggcaaag tcaattctac aacaagcagg agttgaaatg  1080
aaatcggaat tcttgccac aaaggctaaa cagtttcaac ggtcccagtt ggtactggtc  1140
acaaaaggat ttaacttgtt ctgtaaatat ataccatg tactgtggca ttcagaattt  1200
cctaaacctc agatattaaa acatgcaatg aaggagtgtt tggaaaaatg cattgagcaa  1260
aatataactt ccatttcctt tcctgcccct gggactggaa acatggaaat aaagaaggaa  1320
acagcagcag agattttgtt tgatgaagtt ttaacatttg ccaagacca tgtaaaacac  1380
cagttaactg taaaatttgt gatctttcca acagatttgg agatatataa ggctttcagt  1440
tctgaaatgg caaagaggtc caagatgctg agtttgaaca attacagtgt cccccagtca  1500
accagagagg agaaaagaga aaatgggctt gaagctagat ctcctgccat caatctgatg  1560
ggattcaacg tggaagagat gtatgaggcc cacgcatgga tccaaagaat cctgagtctc  1620
cagaaccacc acatcattga gaataatcat attctgtacc ttgggagaaa ggaacatgac  1680
attttgtctc agcttcagaa aacttcaagt gtctccatca cagaaattat cagcccagga  1740
aggacagagt tagagattga aggagcccgg gctgacctca ttgaggtggt tatgaacatt  1800
gaagatatgc tttgtaaagt acaggaggaa atggcaagga aaaggagcg aggcctttgg  1860
cgctcgttag acagtggac tattcagcaa caaaaaccc aagacgaaat gaagaaaat  1920
atcatatttc tgaaatgtcc tgtgcctcca actcaagagc ttctagatca aaagaaacag  1980
tttgaaaaat gtggtttgca ggttctaaag gtggagaaga tagacaatga ggtccttatg  2040
gctgcctttc aaagaaagaa gaaaatgatg aagaaaaac tgcacaggca acctgtgagc  2100
cataggctgt ttcagcaagt cccataccag ttctgcaatg tggtatgcag agttggcttt  2160
caaagaatgt actcgacacc ttgcgatcca aaatacggag ctggcatata cttcaccaag  2220
aacctcaaaa acctggcaga aaggccaag aaaatctctg ctgcagataa gctgatctat  2280
gtgtttgagg ctgaagtact cacaggcttc ttctgccagg acatccgtt aaatattgtt  2340
```

-continued

```
cccccaccac tgagtcctgg agctatagat ggtcatgaca gtgtggttga caatgtctcc    2400
agccctgaaa cctttgttat ttttagtggc atgcaggcta tacctcagta tttgtggaca    2460
tgcacccagg aatatgtaca gtcacaagat tactcatcag gaccaatgag acccttttgca   2520 cagcatcctt ggaggggatt cgcaagtggc agccctgttg attaa                    2565
```

<210> SEQ ID NO 2
<211> LENGTH: 854
<212> TYPE: PRT
<213> ORGANISM: Homo sapiens

<400> SEQUENCE: 2

```
Met Asp Phe Ser Met Val Ala Gly Ala Ala Tyr Asn Glu Lys Ser
1               5                   10                  15

Gly Arg Ile Thr Ser Leu Ser Leu Leu Phe Gln Lys Val Phe Ala Gln
            20                  25                  30

Ile Phe Pro Gln Trp Arg Lys Gly Asn Thr Glu Glu Cys Leu Pro Tyr
        35                  40                  45

Lys Cys Ser Glu Thr Gly Ala Leu Gly Glu Asn Tyr Ser Trp Gln Ile
    50                  55                  60

Pro Ile Asn His Asn Asp Phe Lys Ile Leu Lys Asn Glu Arg Gln
65                  70                  75                  80

Leu Cys Glu Val Leu Gln Asn Lys Phe Gly Cys Ile Ser Thr Leu Val
                85                  90                  95

Ser Pro Val Gln Glu Gly Asn Ser Lys Ser Leu Gln Val Phe Arg Lys
            100                 105                 110

Met Leu Thr Pro Arg Ile Glu Leu Ser Val Trp Lys Asp Asp Leu Thr
        115                 120                 125

Thr His Ala Val Asp Ala Val Asn Ala Ala Asn Glu Asp Leu Leu
130                 135                 140

His Gly Gly Leu Ala Leu Ala Leu Val Lys Ala Gly Gly Phe Glu
145                 150                 155                 160

Ile Gln Glu Glu Ser Lys Gln Phe Val Ala Arg Tyr Gly Lys Val Ser
                165                 170                 175

Ala Gly Glu Ile Ala Val Thr Gly Ala Gly Arg Leu Pro Cys Lys Gln
            180                 185                 190

Ile Ile His Ala Val Gly Pro Arg Trp Met Glu Trp Asp Lys Gln Gly
        195                 200                 205

Cys Thr Gly Lys Leu Gln Arg Ala Ile Val Ser Ile Leu Asn Tyr Val
    210                 215                 220

Ile Tyr Lys Asn Thr His Ile Lys Thr Val Ala Ile Pro Ala Leu Ser
225                 230                 235                 240

Ser Gly Ile Phe Gln Phe Pro Leu Asn Leu Cys Thr Lys Thr Ile Val
                245                 250                 255

Glu Thr Ile Arg Val Ser Leu Gln Gly Lys Pro Met Met Ser Asn Leu
            260                 265                 270

Lys Glu Ile His Leu Val Ser Asn Glu Asp Pro Thr Val Ala Ala Phe
        275                 280                 285

Lys Ala Ala Ser Glu Phe Ile Leu Gly Lys Ser Glu Leu Gly Gln Glu
    290                 295                 300

Thr Thr Pro Ser Phe Asn Ala Met Val Val Asn Asn Leu Thr Leu Gln
305                 310                 315                 320

Ile Val Gln Gly His Ile Glu Trp Gln Thr Ala Asp Val Ile Val Asn
                325                 330                 335
```

```
Ser Val Asn Pro His Asp Ile Thr Val Gly Pro Val Ala Lys Ser Ile
            340                 345                 350

Leu Gln Gln Ala Gly Val Glu Met Lys Ser Glu Phe Leu Ala Thr Lys
            355                 360                 365

Ala Lys Gln Phe Gln Arg Ser Gln Leu Val Leu Val Thr Lys Gly Phe
370                 375                 380

Asn Leu Phe Cys Lys Tyr Ile Tyr His Val Leu Trp His Ser Glu Phe
385                 390                 395                 400

Pro Lys Pro Gln Ile Leu Lys His Ala Met Lys Glu Cys Leu Glu Lys
                405                 410                 415

Cys Ile Glu Gln Asn Ile Thr Ser Ile Ser Phe Pro Ala Leu Gly Thr
            420                 425                 430

Gly Asn Met Glu Ile Lys Lys Glu Thr Ala Ala Glu Ile Leu Phe Asp
            435                 440                 445

Glu Val Leu Thr Phe Ala Lys Asp His Val Lys His Gln Leu Thr Val
            450                 455                 460

Lys Phe Val Ile Phe Pro Thr Asp Leu Glu Ile Tyr Lys Ala Phe Ser
465                 470                 475                 480

Ser Glu Met Ala Lys Arg Ser Lys Met Leu Ser Leu Asn Asn Tyr Ser
                485                 490                 495

Val Pro Gln Ser Thr Arg Glu Glu Lys Arg Glu Asn Gly Leu Glu Ala
            500                 505                 510

Arg Ser Pro Ala Ile Asn Leu Met Gly Phe Asn Val Glu Glu Met Tyr
            515                 520                 525

Glu Ala His Ala Trp Ile Gln Arg Ile Leu Ser Leu Gln Asn His His
            530                 535                 540

Ile Ile Glu Asn His Ile Leu Tyr Leu Gly Arg Lys Glu His Asp
545                 550                 555                 560

Ile Leu Ser Gln Leu Gln Lys Thr Ser Ser Val Ser Ile Thr Glu Ile
                565                 570                 575

Ile Ser Pro Gly Arg Thr Glu Leu Glu Ile Glu Gly Ala Arg Ala Asp
            580                 585                 590

Leu Ile Glu Val Val Met Asn Ile Glu Asp Met Leu Cys Lys Val Gln
            595                 600                 605

Glu Glu Met Ala Arg Lys Lys Glu Arg Gly Leu Trp Arg Ser Leu Gly
610                 615                 620

Gln Trp Thr Ile Gln Gln Lys Thr Gln Asp Glu Met Lys Glu Asn
625                 630                 635                 640

Ile Ile Phe Leu Lys Cys Pro Val Pro Pro Thr Gln Glu Leu Leu Asp
                645                 650                 655

Gln Lys Lys Gln Phe Glu Lys Cys Gly Leu Gln Val Leu Lys Val Glu
            660                 665                 670

Lys Ile Asp Asn Glu Val Leu Met Ala Ala Phe Gln Arg Lys Lys Lys
            675                 680                 685

Met Met Glu Glu Lys Leu His Arg Gln Pro Val Ser His Arg Leu Phe
            690                 695                 700

Gln Gln Val Pro Tyr Gln Phe Cys Asn Val Val Cys Arg Val Gly Phe
705                 710                 715                 720

Gln Arg Met Tyr Ser Thr Pro Cys Asp Pro Lys Tyr Gly Ala Gly Ile
                725                 730                 735

Tyr Phe Thr Lys Asn Leu Lys Asn Leu Ala Glu Lys Ala Lys Lys Ile
            740                 745                 750
```

```
Ser Ala Ala Asp Lys Leu Ile Tyr Val Phe Glu Ala Glu Val Leu Thr
            755                 760                 765
Gly Phe Phe Cys Gln Gly His Pro Leu Asn Ile Val Pro Pro Leu
    770                 775                 780
Ser Pro Gly Ala Ile Asp Gly His Asp Ser Val Val Asp Asn Val Ser
785                 790                 795                 800
Ser Pro Glu Thr Phe Val Ile Phe Ser Gly Met Gln Ala Ile Pro Gln
                805                 810                 815
Tyr Leu Trp Thr Cys Thr Gln Glu Tyr Val Gln Ser Gln Asp Tyr Ser
            820                 825                 830
Ser Gly Pro Met Arg Pro Phe Ala Gln His Pro Trp Arg Gly Phe Ala
        835                 840                 845
Ser Gly Ser Pro Val Asp
    850
```

<210> SEQ ID NO 3
<211> LENGTH: 2460
<212> TYPE: DNA
<213> ORGANISM: Homo sapiens

<400> SEQUENCE: 3

```
atggactttt ccatggtggc cggagcagca gcttacaatg aaaaatcaga gactggtgct      60
cttggagaaa actatagttg gcaaattccc attaaccaca atgacttcaa aattttaaaa     120
aataatgagc gtcagctgtg tgaagtcctc cagaataagt ttggctgtat ctctaccctg     180
gtctctccag ttcaggaagg caacagcaaa tctctgcaag tgttcagaaa atgctgact       240
cctaggatag agttatcagt ctggaaagat gacctcacca cacatgctgt tgatgctgtg     300
gtgaatgcag ccaatgaaga tcttctgcat gggggaggcc tggccctggc cctggtaaaa     360
gctggtggat ttgaaatcca agaagagagc aaacagtttg ttgccagata tggtaaagtg     420
tcagctggtg agatagctgt cacgggagca gggaggcttc cctgcaaaca gatcatccat     480
gctgttgggc tcggtggat ggaatgggat aaacagggat gtactggaaa gctgcagagg     540
gccattgtaa gtattctgaa ttatgtcatc tataaaaata ctcacattaa gacagtagca     600
attccagcct tgagctctgg gatttttcag ttccctctga atttgtgtac aaagactatt     660
gtagagacta tccgggttag tttgcaaggg aagccaatga tgagtaattt gaaagaaatt     720
cacctggtga gcaatgagga ccctactgtt gctgccttta agctgcttc agaattcatc      780
ctagggaaga gtgagctggg acaagaaacc acccttctt tcaatgcaat ggtcgtgaac      840
aacctgaccc tccagattgt ccagggccac attgaatggc agacggcaga tgtaattgtt     900
aattctgtaa acccacatga tattacagtt ggacctgtgg caaagtcaat tctacaacaa     960
gcaggagttg aaatgaaatc ggaatttctt gccacaaagg ctaaacagtt caacggtcc     1020
cagttggtac tggtcacaaa aggatttaac ttgttctgta atatatata ccatgtactg     1080
tggcattcag aatttcctaa acctcagata ttaaaacatg caatgaagga gtgtttggaa    1140
aaatgcattg agcaaaatat aacttccatt tcctttcctg cccttgggac tggaaacatg    1200
gaaataaaga aggaaacagc agcagagatt ttgtttgatg aagttttaac atttgccaaa    1260
gaccatgtaa acaccagtt aactgtaaaa tttgtgatct ttccaacaga tttggagata    1320
tataaggctt tcagttctga atggcaaag aggtccaaga tgctgagttt gaacaattac    1380
agtgtccccc agtcaaccag agaggagaaa agagaaatg gcttgaagc tagatctcct    1440
gccatcaatc tgatgggatt caacgtggaa gagatgtatg aggcccacgc atggatccaa    1500
```

-continued

```
agaatcctga gtctccagaa ccaccacatc attgagaata atcatattct gtaccttggg      1560
agaaaggaac atgacatttt gtctcagctt cagaaaactt caagtgtctc catcacagaa      1620
attatcagcc caggaaggac agagttagag attgaaggag cccgggctga cctcattgag      1680
gtggttatga acattgaaga tatgctttgt aaagtacagg aggaaatggc aaggaaaaag      1740
gagcgaggcc tttggcgctc gttaggacag tggactattc agcaacaaaa aacccaagac      1800
gaaatgaaag aaaatatcat atttctgaaa tgtcctgtgc ctccaactca agagcttcta      1860
gatcaaaaga aacagtttga aaaatgtggt ttgcaggttc taaaggtgga aagatagac       1920 aatgaggtcc ttatggctgc ctttcaaaga aagaagaaaa tgatggaaga aaaactgcac      1980
aggcaacctg tgagccatag gctgtttcag caagtcccat accagttctg caatgtggta      2040
tgcagagttg gctttcaaag aatgtactcg acaccttgcg atccaaaata cggagctggc      2100
atatacttca ccaagaacct caaaaacctg gcagagaagg ccaagaaaat ctctgctgca      2160
gataagctga tctatgtgtt tgaggctgaa gtactcacag gcttcttctg ccagggacat      2220
ccgttaaata ttgttccccc accactgagt cctggagcta tagatggtca tgacagtgtg      2280
gttgacaatg tctccagccc tgaaaccttt gttatttta gtggcatgca ggctatacct       2340
cagtatttgt ggacatgcac ccaggaatat gtacagtcac aagattactc atcaggacca      2400
atgagaccct ttgcacagca tccttggagg ggattcgcaa gtggcagccc tgttgattaa      2460
```

```
<210> SEQ ID NO 4
<211> LENGTH: 819
<212> TYPE: PRT
<213> ORGANISM: Homo sapiens

<400> SEQUENCE: 4
```

```
Met Asp Phe Ser Met Val Ala Gly Ala Ala Tyr Asn Glu Lys Ser
1               5                   10                  15

Glu Thr Gly Ala Leu Gly Glu Asn Tyr Ser Trp Gln Ile Pro Ile Asn
                20                  25                  30

His Asn Asp Phe Lys Ile Leu Lys Asn Asn Glu Arg Gln Leu Cys Glu
            35                  40                  45

Val Leu Gln Asn Lys Phe Gly Cys Ile Ser Thr Leu Val Ser Pro Val
        50                  55                  60

Gln Glu Gly Asn Ser Lys Ser Leu Gln Val Phe Arg Lys Met Leu Thr
65                  70                  75                  80

Pro Arg Ile Glu Leu Ser Val Trp Lys Asp Asp Leu Thr Thr His Ala
                85                  90                  95

Val Asp Ala Val Val Asn Ala Ala Asn Glu Asp Leu Leu His Gly Gly
            100                 105                 110

Gly Leu Ala Leu Ala Leu Val Lys Ala Gly Gly Phe Glu Ile Gln Glu
        115                 120                 125

Glu Ser Lys Gln Phe Val Ala Arg Tyr Gly Lys Val Ser Ala Gly Glu
    130                 135                 140

Ile Ala Val Thr Gly Ala Gly Arg Leu Pro Cys Lys Gln Ile Ile His
145                 150                 155                 160

Ala Val Gly Pro Arg Trp Met Glu Trp Asp Lys Gln Gly Cys Thr Gly
                165                 170                 175

Lys Leu Gln Arg Ala Ile Val Ser Ile Leu Asn Tyr Val Ile Tyr Lys
            180                 185                 190

Asn Thr His Ile Lys Thr Val Ala Ile Pro Ala Leu Ser Ser Gly Ile
        195                 200                 205
```

-continued

```
Phe Gln Phe Pro Leu Asn Leu Cys Thr Lys Thr Ile Val Glu Thr Ile
210                 215                 220

Arg Val Ser Leu Gln Gly Lys Pro Met Met Ser Asn Leu Lys Glu Ile
225                 230                 235                 240

His Leu Val Ser Asn Glu Asp Pro Thr Val Ala Ala Phe Lys Ala Ala
            245                 250                 255

Ser Glu Phe Ile Leu Gly Lys Ser Glu Leu Gly Gln Glu Thr Thr Pro
            260                 265                 270

Ser Phe Asn Ala Met Val Val Asn Leu Thr Leu Gln Ile Val Gln
            275                 280                 285

Gly His Ile Glu Trp Gln Thr Ala Asp Val Ile Val Asn Ser Val Asn
290                 295                 300

Pro His Asp Ile Thr Val Gly Pro Val Ala Lys Ser Ile Leu Gln Gln
305                 310                 315                 320

Ala Gly Val Glu Met Lys Ser Glu Phe Leu Ala Thr Lys Ala Lys Gln
            325                 330                 335

Phe Gln Arg Ser Gln Leu Val Leu Val Thr Lys Gly Phe Asn Leu Phe
            340                 345                 350

Cys Lys Tyr Ile Tyr His Val Leu Trp His Ser Glu Phe Pro Lys Pro
            355                 360                 365

Gln Ile Leu Lys His Ala Met Lys Glu Cys Leu Glu Lys Cys Ile Glu
370                 375                 380

Gln Asn Ile Thr Ser Ile Ser Phe Pro Ala Leu Gly Thr Gly Asn Met
385                 390                 395                 400

Glu Ile Lys Lys Glu Thr Ala Ala Glu Ile Leu Phe Asp Glu Val Leu
            405                 410                 415

Thr Phe Ala Lys Asp His Val Lys His Gln Leu Thr Val Lys Phe Val
            420                 425                 430

Ile Phe Pro Thr Asp Leu Glu Ile Tyr Lys Ala Phe Ser Ser Glu Met
            435                 440                 445

Ala Lys Arg Ser Lys Met Leu Ser Leu Asn Asn Tyr Ser Val Pro Gln
450                 455                 460

Ser Thr Arg Glu Glu Lys Arg Glu Asn Gly Leu Glu Ala Arg Ser Pro
465                 470                 475                 480

Ala Ile Asn Leu Met Gly Phe Asn Val Glu Glu Met Tyr Glu Ala His
            485                 490                 495

Ala Trp Ile Gln Arg Ile Leu Ser Leu Gln Asn His His Ile Ile Glu
            500                 505                 510

Asn Asn His Ile Leu Tyr Leu Gly Arg Lys Glu His Asp Ile Leu Ser
            515                 520                 525

Gln Leu Gln Lys Thr Ser Ser Val Ser Ile Thr Glu Ile Ile Ser Pro
530                 535                 540

Gly Arg Thr Glu Leu Glu Ile Glu Gly Ala Arg Ala Asp Leu Ile Glu
545                 550                 555                 560

Val Val Met Asn Ile Glu Asp Met Leu Cys Lys Val Gln Glu Glu Met
            565                 570                 575

Ala Arg Lys Lys Glu Arg Gly Leu Trp Arg Ser Leu Gly Gln Trp Thr
            580                 585                 590

Ile Gln Gln Gln Lys Thr Gln Asp Glu Met Lys Glu Asn Ile Ile Phe
            595                 600                 605

Leu Lys Cys Pro Val Pro Pro Thr Gln Glu Leu Leu Asp Gln Lys Lys
610                 615                 620

Gln Phe Glu Lys Cys Gly Leu Gln Val Leu Lys Val Glu Lys Ile Asp
```

-continued

```
                625                 630                 635                 640
            Asn Glu Val Leu Met Ala Ala Phe Gln Arg Lys Lys Met Met Glu
                            645                 650                 655
            Glu Lys Leu His Arg Gln Pro Val Ser His Arg Leu Phe Gln Gln Val
                            660                 665                 670
            Pro Tyr Gln Phe Cys Asn Val Val Cys Arg Val Gly Phe Gln Arg Met
                            675                 680                 685
            Tyr Ser Thr Pro Cys Asp Pro Lys Tyr Gly Ala Gly Ile Tyr Phe Thr
                690                 695                 700
            Lys Asn Leu Lys Asn Leu Ala Glu Lys Ala Lys Lys Ile Ser Ala Ala
            705                 710                 715                 720
            Asp Lys Leu Ile Tyr Val Phe Glu Ala Glu Val Leu Thr Gly Phe Phe
                            725                 730                 735
            Cys Gln Gly His Pro Leu Asn Ile Val Pro Pro Leu Ser Pro Gly
                            740                 745                 750
            Ala Ile Asp Gly His Asp Ser Val Val Asp Asn Val Ser Ser Pro Glu
                            755                 760                 765
            Thr Phe Val Ile Phe Ser Gly Met Gln Ala Ile Pro Gln Tyr Leu Trp
                770                 775                 780
            Thr Cys Thr Gln Glu Tyr Val Gln Ser Gln Asp Tyr Ser Ser Gly Pro
            785                 790                 795                 800
            Met Arg Pro Phe Ala Gln His Pro Trp Arg Gly Phe Ala Ser Gly Ser
                            805                 810                 815
            Pro Val Asp
```

<210> SEQ ID NO 5
<211> LENGTH: 2133
<212> TYPE: DNA
<213> ORGANISM: Homo sapiens

<400> SEQUENCE: 5

```
atggactttt ccatggtggc cggagcagca gcttacaatg aaaaatcaga gactggtgct      60
cttggagaaa actatagttg caaattccc attaaccaca atgacttcaa aattttaaaa      120
aataatgagc gtcagctgtg tgaagtcctc cagaataagt ttggctgtat ctctaccctg     180
gtctctccag ttcaggaagg caacagcaaa tctctgcaag tgttcagaaa atgctgact      240
cctaggatag agttatcagt ctggaaagat gacctcacca cacatgctgt tgatgctgtg     300
gtgaatgcag ccaatgaaga tcttctgcat ggggaggc tggccctggc cctggtaaaa      360
gctggtggat tgaaatcca agaagagagc aaacagtttg ttgccagata tggtaaagtg     420
tcagctggtg agatagctgt cacgggagca gggaggcttc cctgcaaaca gatcatccat     480
gctgttgggc ctcggtggat ggaatgggat aaacagggat gtactggaaa gctgcagagg     540
gccattgtaa gtattctgaa ttatgtcatc tataaaaata ctcacattaa gacagtagca     600
attccagcct tgagctctgg gatttttcag ttccctctga atttgtgtac aaagactatt     660
gtagagacta ccgggttag tttgcaaggg aagccaatga tgagtaattt gaaagaaatt     720
cacctggtga gcaatgagga ccctactgtt gctgccttta agctgcttc agaattcatc     780
ctagggaaga gtgagctggg acaagaaacc accccttctt tcaatgcaat ggtcgtgaac     840
aacctgaccc tccagattgt ccagggccac attgaatggc agacggcaga tgtaattgtt     900
aattctgtaa accccacatga tattacagtt ggacctgtgg caaagtcaat tctacaacaa     960
gcaggagttg aaatgaaatc ggaatttctt gccacaaagg ctaaacagtt tcaacggtcc    1020
```

```
cagttggtac tggtcacaaa aggatttaac ttgttctgta aatatatata ccatgtactg    1080
tggcattcag aatttcctaa acctcagata ttaaaacatg caatgaagga gtgtttggaa    1140
aaatgcattg agcaaaatat aacttccatt tcctttcctg cccttgggac tggaaacatg    1200
gaaataaaga aggaaacagc agcagagatt ttgtttgatg aagttttaac atttgccaaa    1260
gaccatgtaa acaccagtt aactgtaaaa tttgtgatct ttccaacaga tttggagata    1320
tataaggctt tcagttctga aatggcaaag aggtccaaga tgctgagttt gaacaattac    1380
agtgtccccc agtcaaccag agaggagaaa agagaaaatg ggcttgaagc tagatctcct    1440
gccatcaatc tgatgggatt caacgtggaa gagatgtatg aggcccacgc atggatccaa    1500
agaatcctga gtctccagaa ccaccacatc attgagaata atcatattct gtaccttggg    1560
agaaaggaac atgacatttt gtctcagctt cagaaaactt caagtgtctc catcacagaa    1620
attatcagcc caggaaggac agagttagag attgaaggag cccgggctga cctcattgag    1680
gtggttatga acattgaaga tatgctttgt aaagtacagg aggaaatggc aaggaaaaag    1740
gagcgaggcc tttggcgctc gttaggacag tggactattc agcaacaaaa aacccaagac    1800
gaaatgaaag aaaatatcat atttctgaaa tgtcctgtgc ctccaactca agagcttcta    1860
gatcaaaaga aacagtttga aaaatgtggt ttgcaggttc taaaggtgga aagatagac    1920 aatgaggtcc ttatggctgc ctttcaaaga aagaagaaaa tgatggaaga aaaactgcac    1980
aggcaacctg tgagccatag gctgtttcag caagtcccat accagttctg caatgtggta    2040
tgcagagttg gctttcaaag aatgtactcg acaccttgcg gtaggtgtca atgcctcatc    2100
attggggcta ctctgtggaa tttggtgagc tga                                2133
```

<210> SEQ ID NO 6
<211> LENGTH: 710
<212> TYPE: PRT
<213> ORGANISM: Homo sapiens

<400> SEQUENCE: 6

```
Met Asp Phe Ser Met Val Ala Gly Ala Ala Tyr Asn Glu Lys Ser
1               5                   10                  15

Glu Thr Gly Ala Leu Gly Glu Asn Tyr Ser Trp Gln Ile Pro Ile Asn
            20                  25                  30

His Asn Asp Phe Lys Ile Leu Lys Asn Asn Glu Arg Gln Leu Cys Glu
        35                  40                  45

Val Leu Gln Asn Lys Phe Gly Cys Ile Ser Thr Leu Val Ser Pro Val
    50                  55                  60

Gln Glu Gly Asn Ser Lys Ser Leu Gln Val Phe Arg Lys Met Leu Thr
65                  70                  75                  80

Pro Arg Ile Glu Leu Ser Val Trp Lys Asp Asp Leu Thr Thr His Ala
                85                  90                  95

Val Asp Ala Val Val Asn Ala Ala Asn Glu Asp Leu Leu His Gly Gly
            100                 105                 110

Gly Leu Ala Leu Ala Leu Val Lys Ala Gly Gly Phe Glu Ile Gln Glu
        115                 120                 125

Glu Ser Lys Gln Phe Val Ala Arg Tyr Gly Lys Val Ser Ala Gly Glu
    130                 135                 140

Ile Ala Val Thr Gly Ala Gly Arg Leu Pro Cys Lys Gln Ile Ile His
145                 150                 155                 160

Ala Val Gly Pro Arg Trp Met Glu Trp Asp Lys Gln Gly Cys Thr Gly
                165                 170                 175
```

-continued

Lys Leu Gln Arg Ala Ile Val Ser Ile Leu Asn Tyr Val Ile Tyr Lys
            180                 185                 190

Asn Thr His Ile Lys Thr Val Ala Ile Pro Ala Leu Ser Ser Gly Ile
            195                 200                 205

Phe Gln Phe Pro Leu Asn Leu Cys Thr Lys Thr Ile Val Glu Thr Ile
    210                 215                 220

Arg Val Ser Leu Gln Gly Lys Pro Met Met Ser Asn Leu Lys Glu Ile
225                 230                 235                 240

His Leu Val Ser Asn Glu Asp Pro Thr Val Ala Ala Phe Lys Ala Ala
                245                 250                 255

Ser Glu Phe Ile Leu Gly Lys Ser Glu Leu Gly Gln Glu Thr Thr Pro
                260                 265                 270

Ser Phe Asn Ala Met Val Val Asn Asn Leu Thr Leu Gln Ile Val Gln
    275                 280                 285

Gly His Ile Glu Trp Gln Thr Ala Asp Val Ile Val Asn Ser Val Asn
    290                 295                 300

Pro His Asp Ile Thr Val Gly Pro Val Ala Lys Ser Ile Leu Gln Gln
305                 310                 315                 320

Ala Gly Val Glu Met Lys Ser Glu Phe Leu Ala Thr Lys Ala Lys Gln
                325                 330                 335

Phe Gln Arg Ser Gln Leu Val Leu Val Thr Lys Gly Phe Asn Leu Phe
                340                 345                 350

Cys Lys Tyr Ile Tyr His Val Leu Trp His Ser Glu Phe Pro Lys Pro
            355                 360                 365

Gln Ile Leu Lys His Ala Met Lys Glu Cys Leu Glu Lys Cys Ile Glu
    370                 375                 380

Gln Asn Ile Thr Ser Ile Ser Phe Pro Ala Leu Gly Thr Gly Asn Met
385                 390                 395                 400

Glu Ile Lys Lys Glu Thr Ala Ala Glu Ile Leu Phe Asp Glu Val Leu
                405                 410                 415

Thr Phe Ala Lys Asp His Val Lys His Gln Leu Thr Val Lys Phe Val
                420                 425                 430

Ile Phe Pro Thr Asp Leu Glu Ile Tyr Lys Ala Phe Ser Ser Glu Met
            435                 440                 445

Ala Lys Arg Ser Lys Met Leu Ser Leu Asn Asn Tyr Ser Val Pro Gln
    450                 455                 460

Ser Thr Arg Glu Glu Lys Arg Glu Asn Gly Leu Glu Ala Arg Ser Pro
465                 470                 475                 480

Ala Ile Asn Leu Met Gly Phe Asn Val Glu Glu Met Tyr Glu Ala His
                485                 490                 495

Ala Trp Ile Gln Arg Ile Leu Ser Leu Gln Asn His His Ile Ile Glu
            500                 505                 510

Asn Asn His Ile Leu Tyr Leu Gly Arg Lys Glu His Asp Ile Leu Ser
    515                 520                 525

Gln Leu Gln Lys Thr Ser Ser Val Ser Ile Thr Glu Ile Ile Ser Pro
    530                 535                 540

Gly Arg Thr Glu Leu Glu Ile Glu Gly Ala Arg Ala Asp Leu Ile Glu
545                 550                 555                 560

Val Val Met Asn Ile Glu Asp Met Leu Cys Lys Val Gln Glu Glu Met
                565                 570                 575

Ala Arg Lys Lys Glu Arg Gly Leu Trp Arg Ser Leu Gly Gln Trp Thr
            580                 585                 590

Ile Gln Gln Gln Lys Thr Gln Asp Glu Met Lys Glu Asn Ile Ile Phe

|  |  | 595 |  |  | 600 |  |  | 605 |  |

Leu Lys Cys Pro Val Pro Pro Thr Gln Glu Leu Leu Asp Gln Lys Lys
610                615                620

Gln Phe Glu Lys Cys Gly Leu Gln Val Leu Lys Val Glu Lys Ile Asp
625                630                635                640

Asn Glu Val Leu Met Ala Ala Phe Gln Arg Lys Lys Met Met Glu
                645                650                655

Glu Lys Leu His Arg Gln Pro Val Ser His Arg Leu Phe Gln Gln Val
            660                665                670

Pro Tyr Gln Phe Cys Asn Val Val Cys Arg Val Gly Phe Gln Arg Met
            675                680                685

Tyr Ser Thr Pro Cys Gly Arg Cys Gln Cys Leu Ile Ile Gly Ala Thr
690                695                700

Leu Trp Asn Leu Val Ser
705                710

```
<210> SEQ ID NO 7
<211> LENGTH: 2493
<212> TYPE: DNA
<213> ORGANISM: Mus musculus

<400> SEQUENCE: 7
```

| atggcctatt acatggatac atgggcggca gctcccgccg aaagaccagc caacaattct | 60 |
|---|---|
| cttgaagaac attatagatg gcaaattccc attaaacaca atgtcttcga aattttaaag | 120 |
| agcaatgaga gtcagctatg tgaagtcctc caaaataagt ttggatgcat ctctaccctg | 180 |
| agctgtccaa ctctagcagg gagcagctct cctgctcaga gagtcttcag aaggaccctg | 240 |
| atccctggga tagagttatc tgtctggaag gatgacctta ccagacacgt tgttgatgct | 300 |
| gtggtgaacg cagccaatga aaaccttttg catggaagtg gcctggccgg aagcttggtg | 360 |
| aaaactggtg gctttgaaat ccaagaagag agcaaaagaa tcattgccaa cgttggtaaa | 420 |
| atctcagttg gtggaatcgc tatcaccggt gcggggagac ttccttgcca tttgattatc | 480 |
| catgcggttg gacctcggtg gacagttacg aacagccaga cagctatcga attactgaaa | 540 |
| tttgccatta ggaacattct agattatgtc accaaatatg atctacgcat taagacagta | 600 |
| gcaattccag ccctgagctc tggaattttc cagttccctc tggatttgtg tacaagcata | 660 |
| attttagaaa ctatccggct ttatttccaa gacaagcaaa tgttcggtaa tttgagagag | 720 |
| attcatctgg tgagcaatga ggaccccact gttgcgtcct taaatccgc tcagaaagc | 780 |
| atcctaggga gggacctgag ctcttggggg ggtccagaaa ctgaccctgc ttccaccatg | 840 |
| actcttcgca tcggccgggg cctgactctc cagattgtcc aaggctgtat tgaaatgcaa | 900 |
| acaacagatg taattgttaa ttctggatac atgcaggatt ttaaatcagg acgagtggca | 960 |
| cagtcgattc ttagacaagc aggggttgaa atggaaaagg aacttgacaa ggttaacctg | 1020 |
| tccacagatt atcaagaggt gtgggtcaca aaaggattta aattgtcctg tcagtatgtc | 1080 |
| ttccatgtgg catggcattc ccaaatcaac aaataccaga tattgaaaga tgcaatgaag | 1140 |
| tcctgtctag aaaaatgcct taaccagat ataaattcca tttcctttcc tgctctcggg | 1200 |
| acaggattga tggatttgaa gagagtacag cagctcaga taatgtttga ggaagttttt | 1260 |
| gcatttgcta agagcacaa ggaaaaaacg ctaactgtaa agattgtgat ctttccagta | 1320 |
| gatgtggaga cgtacaagat tttttatgct gaaatgacaa aaaggtccaa cgagctgaat | 1380 |
| ctcagcggta atagtggtgc tttagccctg cagtggtcca gtggggagca aagaagaggc | 1440 |

```
ggccttgaag ctggatctcc tgccatcaat ctcatgggtg taaaagtggg agagatgtgt   1500
gaggcccagg aatggattga aaggttgctg gtctccctgg accaccacat cattgagaat   1560
aatcatattc tctatcttgg gaaaaagag cacgacgtgc tgtctgagct ccagaccagc   1620
acaagagtct ccatttcaga gactgtcagt ccaagaacgg ccactttgga gattaaaggt   1680
ccccaggctg acctcattga cgcagttatg aggattgaat gtatgctgtg tgacgttcag   1740
gaagaagtgg caggaaaaag ggagaaaaat ctttggagct tgtcaggaca ggggaccaac   1800
cagcaagaaa aactggataa aatggaagaa tcgtacacat ttcaacgata cccagcatca   1860
ttaactcagg aacttcagga ccgaagaaa cagtttgaaa agtgtggctt gtgggttgtg   1920
caggtggagc agatagacaa taaggtgctg ctggctgcct ccaagagaa gaagaaaatg   1980 atggaagaga ggacgccaaa gggatctggg agccaaaggt tgtttcagca ggtcccacat   2040
cagttctgca atacggtgtg cagagtcggc ttccacagaa tgtattcgac atcctataac   2100
ccagtttatg gagccggcat atatttcacc aagagcctca aaatctagc agacaaggtc   2160 aagaaaacct caagcacaga caagctaatc tatgtgtttg aggcagaagt actcacaggg   2220
tccttctgtc agggtaattc ctcaaatatc atccctccac cattgagtcc tggggcctta   2280
gatgtcaatg acagcgtagt tgacaatgtt ccagccctg aaaccattgt tgttttaat    2340 ggcatgcagg ccatgcccct gtacttgtgg acttgcacac aggataggac attctcacag   2400
catccgatgt ggtcacaggg ctactcatca ggaccaggaa tggtctcttc gctgcagtcc   2460
tgggaatggg tcttaaatgg cagctctgtt tag                                2493
```

<210> SEQ ID NO 8
<211> LENGTH: 830
<212> TYPE: PRT
<213> ORGANISM: Mus musculus

<400> SEQUENCE: 8

```
Met Ala Tyr Tyr Met Asp Thr Trp Ala Ala Pro Ala Glu Arg Pro
1               5                   10                  15

Ala Asn Asn Ser Leu Glu Glu His Tyr Arg Trp Gln Ile Pro Ile Lys
            20                  25                  30

His Asn Val Phe Glu Ile Leu Lys Ser Asn Glu Ser Gln Leu Cys Glu
        35                  40                  45

Val Leu Gln Asn Lys Phe Gly Cys Ile Ser Thr Leu Ser Cys Pro Thr
    50                  55                  60

Leu Ala Gly Ser Ser Pro Ala Gln Arg Val Phe Arg Arg Thr Leu
65                  70                  75                  80

Ile Pro Gly Ile Glu Leu Ser Val Trp Lys Asp Asp Leu Thr Arg His
                85                  90                  95

Val Val Asp Ala Val Val Asn Ala Ala Asn Glu Asn Leu Leu His Gly
            100                 105                 110

Ser Gly Leu Ala Gly Ser Leu Val Lys Thr Gly Gly Phe Glu Ile Gln
        115                 120                 125

Glu Glu Ser Lys Arg Ile Ile Ala Asn Val Gly Lys Ile Ser Val Gly
    130                 135                 140

Gly Ile Ala Ile Thr Gly Ala Gly Arg Leu Pro Cys His Leu Ile Ile
145                 150                 155                 160

His Ala Val Gly Pro Arg Trp Thr Val Thr Asn Ser Gln Thr Ala Ile
                165                 170                 175

Glu Leu Leu Lys Phe Ala Ile Arg Asn Ile Leu Asp Tyr Val Thr Lys
            180                 185                 190
```

-continued

```
Tyr Asp Leu Arg Ile Lys Thr Val Ala Ile Pro Ala Leu Ser Ser Gly
        195                 200                 205

Ile Phe Gln Phe Pro Leu Asp Leu Cys Thr Ser Ile Ile Leu Glu Thr
210                 215                 220

Ile Arg Leu Tyr Phe Gln Asp Lys Gln Met Phe Gly Asn Leu Arg Glu
225                 230                 235                 240

Ile His Leu Val Ser Asn Glu Asp Pro Thr Val Ala Ser Phe Lys Ser
                245                 250                 255

Ala Ser Glu Ser Ile Leu Gly Arg Asp Leu Ser Ser Trp Gly Gly Pro
                260                 265                 270

Glu Thr Asp Pro Ala Ser Thr Met Thr Leu Arg Ile Gly Arg Gly Leu
                275                 280                 285

Thr Leu Gln Ile Val Gln Gly Cys Ile Glu Met Gln Thr Thr Asp Val
290                 295                 300

Ile Val Asn Ser Gly Tyr Met Gln Asp Phe Lys Ser Gly Arg Val Ala
305                 310                 315                 320

Gln Ser Ile Leu Arg Gln Ala Gly Val Glu Met Glu Lys Glu Leu Asp
                325                 330                 335

Lys Val Asn Leu Ser Thr Asp Tyr Gln Glu Val Trp Val Thr Lys Gly
                340                 345                 350

Phe Lys Leu Ser Cys Gln Tyr Val Phe His Val Ala Trp His Ser Gln
                355                 360                 365

Ile Asn Lys Tyr Gln Ile Leu Lys Asp Ala Met Lys Ser Cys Leu Glu
                370                 375                 380

Lys Cys Leu Lys Pro Asp Ile Asn Ser Ile Ser Phe Pro Ala Leu Gly
385                 390                 395                 400

Thr Gly Leu Met Asp Leu Lys Lys Ser Thr Ala Ala Gln Ile Met Phe
                405                 410                 415

Glu Glu Val Phe Ala Phe Ala Lys Glu His Lys Glu Lys Thr Leu Thr
                420                 425                 430

Val Lys Ile Val Ile Phe Pro Val Asp Val Glu Thr Tyr Lys Ile Phe
        435                 440                 445

Tyr Ala Glu Met Thr Lys Arg Ser Asn Glu Leu Asn Leu Ser Gly Asn
450                 455                 460

Ser Gly Ala Leu Ala Leu Gln Trp Ser Ser Gly Glu Gln Arg Arg Gly
465                 470                 475                 480

Gly Leu Glu Ala Gly Ser Pro Ala Ile Asn Leu Met Gly Val Lys Val
                485                 490                 495

Gly Glu Met Cys Glu Ala Gln Glu Trp Ile Glu Arg Leu Leu Val Ser
                500                 505                 510

Leu Asp His His Ile Ile Glu Asn Asn His Ile Leu Tyr Leu Gly Lys
                515                 520                 525

Lys Glu His Asp Val Leu Ser Glu Leu Gln Thr Ser Thr Arg Val Ser
                530                 535                 540

Ile Ser Glu Thr Val Ser Pro Arg Thr Ala Thr Leu Glu Ile Lys Gly
545                 550                 555                 560

Pro Gln Ala Asp Leu Ile Asp Ala Val Met Arg Ile Glu Cys Met Leu
                565                 570                 575

Cys Asp Val Gln Glu Val Ala Gly Lys Arg Glu Lys Asn Leu Trp
                580                 585                 590

Ser Leu Ser Gly Gln Gly Thr Asn Gln Gln Glu Lys Leu Asp Lys Met
                595                 600                 605
```

```
Glu Glu Ser Tyr Thr Phe Gln Arg Tyr Pro Ala Ser Leu Thr Gln Glu
610                 615                 620

Leu Gln Asp Arg Lys Lys Gln Phe Glu Lys Cys Gly Leu Trp Val Val
625                 630                 635                 640

Gln Val Glu Gln Ile Asp Asn Lys Val Leu Leu Ala Ala Phe Gln Glu
                645                 650                 655

Lys Lys Lys Met Met Glu Glu Arg Thr Pro Lys Gly Ser Gly Ser Gln
                660                 665                 670

Arg Leu Phe Gln Gln Val Pro His Gln Phe Cys Asn Thr Val Cys Arg
                675                 680                 685

Val Gly Phe His Arg Met Tyr Ser Thr Ser Tyr Asn Pro Val Tyr Gly
690                 695                 700

Ala Gly Ile Tyr Phe Thr Lys Ser Leu Lys Asn Leu Ala Asp Lys Val
705                 710                 715                 720

Lys Lys Thr Ser Ser Thr Asp Lys Leu Ile Tyr Val Phe Glu Ala Glu
                725                 730                 735

Val Leu Thr Gly Ser Phe Cys Gln Gly Asn Ser Ser Asn Ile Ile Pro
                740                 745                 750

Pro Pro Leu Ser Pro Gly Ala Leu Asp Val Asn Asp Ser Val Val Asp
                755                 760                 765

Asn Val Ser Ser Pro Glu Thr Ile Val Val Phe Asn Gly Met Gln Ala
                770                 775                 780

Met Pro Leu Tyr Leu Trp Thr Cys Thr Gln Asp Arg Thr Phe Ser Gln
785                 790                 795                 800

His Pro Met Trp Ser Gln Gly Tyr Ser Ser Gly Pro Gly Met Val Ser
                805                 810                 815

Ser Leu Gln Ser Trp Glu Trp Val Leu Asn Gly Ser Ser Val
                820                 825                 830

<210> SEQ ID NO 9
<211> LENGTH: 2223
<212> TYPE: DNA
<213> ORGANISM: Homo sapiens

<400> SEQUENCE: 9
atggcctccc acctgcgccc gccgtccccg ctcctcgtgc gggtgtacaa gtccggcccc     60
cgagtacgaa ggaagctgga gagctacttc cagagctcta agtcctcggg cggcggggag    120
tgcacggtca gcacccagga cacgaagcc cgggcacct tccgggtgga gttcagtgaa     180 aggcagcta aggagagagt gttgaaaaaa ggagagcacc aaatacttgt tgacgaaaaa    240
cctgtgccca ttttcctggt acccactgaa aattcaataa agaagaacac gagacctcaa    300
atttcttcac tgacacaatc acaagcgaaa caccgtctg gtgatatgca tcaacatgaa    360
ggacatattc ctaatgctgt ggattcctgt ctccaaaaga tctttcttac tgtaacagct    420
gacctgaact gtaacctgtt ctccaaagag cagagggcat acataaccac actgtgccct    480
agtatcagaa aaatggaagg tcacgatgga attgagaagg tgtgtggtga cttccaagac    540
attgaaagaa tacatcaatt tttgagtgag cagttcctgg aaagtgagca gaacaacaa    600 ttttccctt caatgacaga gaggaagcca ctcagtcagc aggagaggga cagctgcatt    660
tctccttctg aaccagaaac caaggcagaa caaaaaagca actatttga gttcccttg    720 ccttactttg aatacttta atatatctgt cctgataaaa tcaactcaat agagaaaga    780 tttggtgtaa acattgaaat ccaggagagt tctccaaata tggtctgttt agatttcacc    840
tcaagtcgat caggtgacct ggaagcagct cgtgagtctt ttgctagtga atttcagaag    900
```

```
aacacagaac ctctgaagca agaatgtgtc tctttagcag acagtaagca ggcaaataaa    960
ttcaaacagg aattgaatca ccagtttaca aagctcctta taaggagaa aggaggcgaa   1020
ttaactctcc ttgggaccca agatgacatt tcagctgcca aacaaaaaat ctctgaagct   1080
tttgtcaaga tacctgtgaa actatttgct gccaattaca tgatgaatgt aattgaggtt   1140
gatagtgccc actataaact tttagaaact gaattactac aggagatatc agagatcgaa   1200
aaaaggtatg acatttgcag caaggtttct gagaaaggtc agaaacctg cattctgttt    1260
gaatccaagg acaggcaggt agatctatct gtgcatgctt atgcaagttt catcgatgcc   1320
tttcaacatg cctcatgtca gttgatgaga aagttctttt tactgaagtc tttgggcaag   1380
gagagaaagc acttacatca gaccaagttt gctgatgact ttagaaaaag acatccaaat   1440
gtacactttg tgctaaatca agagtcaatg actttgactg gtttgccaaa tcaccttgca   1500
aaggcgaagc agtatgttct aaaaggagga ggaatgtctt cattggctgg aaagaaattg   1560
aaagagggtc atgaaacacc gatggacatt gatagcgatg attccaaagc agcttctccg   1620
ccactcaagg gctctgtgag ttctgaggcc tcagaactgg acaagaagga aaagggcatc   1680
tgtgtcatct gtatggacac cattagtaac aaaaaagtgc taccaaagtg caagcatgaa   1740
ttctgcgccc cttgtatcaa caaagccatg tcatataagc caatctgtcc cacatgccag   1800
acttcctatg gtattcagaa aggaaatcag ccagagggaa gcatggtttt cactgtttca   1860
agagactcac ttccaggtta tgagtccttt ggcaccattg tgattactta ttctatgaaa   1920
gcaggcatac aaacgaaga acacccaaac ccaggaaaga gatacctgg aatacagcga    1980
actgcatact tgcctgataa taaggaagga aggaaggttt tgaaactgct ttatagggcc   2040
tttgaccaaa agctgatttt tacagtgggg tactctcgcg tattaggagt ctcagatgtc   2100
atcacttgga atgatattca ccacaaaaca tcccggtttg gaggaccaga aatgtatggc   2160
tatcctgatc cttcttacct gaaacgtgtc aaagaggagc tgaaagccaa aggaattgag   2220
taa                                                                2223
```

<210> SEQ ID NO 10
<211> LENGTH: 740
<212> TYPE: PRT
<213> ORGANISM: Homo sapiens

<400> SEQUENCE: 10

```
Met Ala Ser His Leu Arg Pro Pro Pro Leu Leu Val Arg Val Tyr
1               5                   10                  15

Lys Ser Gly Pro Arg Val Arg Arg Lys Leu Glu Ser Tyr Phe Gln Ser
            20                  25                  30

Ser Lys Ser Ser Gly Gly Gly Glu Cys Thr Val Ser Thr Gln Glu His
        35                  40                  45

Glu Ala Pro Gly Thr Phe Arg Val Glu Phe Ser Glu Arg Ala Ala Lys
    50                  55                  60

Glu Arg Val Leu Lys Lys Gly Glu His Gln Ile Leu Val Asp Glu Lys
65                  70                  75                  80

Pro Val Pro Ile Phe Leu Val Pro Thr Glu Asn Ser Ile Lys Lys Asn
                85                  90                  95

Thr Arg Pro Gln Ile Ser Ser Leu Thr Gln Ser Gln Ala Glu Thr Pro
            100                 105                 110

Ser Gly Asp Met His Gln His Glu Gly His Ile Pro Asn Ala Val Asp
        115                 120                 125
```

-continued

Ser Cys Leu Gln Lys Ile Phe Leu Thr Val Thr Ala Asp Leu Asn Cys
    130                 135                 140

Asn Leu Phe Ser Lys Glu Gln Arg Ala Tyr Ile Thr Thr Leu Cys Pro
145                 150                 155                 160

Ser Ile Arg Lys Met Glu Gly His Asp Gly Ile Glu Lys Val Cys Gly
                165                 170                 175

Asp Phe Gln Asp Ile Glu Arg Ile His Gln Phe Leu Ser Glu Gln Phe
            180                 185                 190

Leu Glu Ser Glu Gln Lys Gln Gln Phe Ser Pro Ser Met Thr Glu Arg
        195                 200                 205

Lys Pro Leu Ser Gln Gln Glu Arg Asp Ser Cys Ile Ser Pro Ser Glu
210                 215                 220

Pro Glu Thr Lys Ala Glu Gln Lys Ser Asn Tyr Phe Glu Val Pro Leu
225                 230                 235                 240

Pro Tyr Phe Glu Tyr Phe Lys Tyr Ile Cys Pro Asp Lys Ile Asn Ser
                245                 250                 255

Ile Glu Lys Arg Phe Gly Val Asn Ile Glu Ile Gln Glu Ser Ser Pro
            260                 265                 270

Asn Met Val Cys Leu Asp Phe Thr Ser Ser Arg Ser Gly Asp Leu Glu
        275                 280                 285

Ala Ala Arg Glu Ser Phe Ala Ser Glu Phe Gln Lys Asn Thr Glu Pro
    290                 295                 300

Leu Lys Gln Glu Cys Val Ser Leu Ala Asp Ser Lys Gln Ala Asn Lys
305                 310                 315                 320

Phe Lys Gln Glu Leu Asn His Gln Phe Thr Lys Leu Leu Ile Lys Glu
                325                 330                 335

Lys Gly Gly Glu Leu Thr Leu Leu Gly Thr Gln Asp Asp Ile Ser Ala
            340                 345                 350

Ala Lys Gln Lys Ile Ser Glu Ala Phe Val Lys Ile Pro Val Lys Leu
        355                 360                 365

Phe Ala Ala Asn Tyr Met Met Asn Val Ile Glu Val Asp Ser Ala His
    370                 375                 380

Tyr Lys Leu Leu Glu Thr Glu Leu Leu Gln Glu Ile Ser Glu Ile Glu
385                 390                 395                 400

Lys Arg Tyr Asp Ile Cys Ser Lys Val Ser Glu Lys Gly Gln Lys Thr
                405                 410                 415

Cys Ile Leu Phe Glu Ser Lys Asp Arg Gln Val Asp Leu Ser Val His
            420                 425                 430

Ala Tyr Ala Ser Phe Ile Asp Ala Phe Gln His Ala Ser Cys Gln Leu
        435                 440                 445

Met Arg Glu Val Leu Leu Leu Lys Ser Leu Gly Lys Glu Arg Lys His
    450                 455                 460

Leu His Gln Thr Lys Phe Ala Asp Asp Phe Arg Lys Arg His Pro Asn
465                 470                 475                 480

Val His Phe Val Leu Asn Gln Glu Ser Met Thr Leu Thr Gly Leu Pro
                485                 490                 495

Asn His Leu Ala Lys Ala Lys Gln Tyr Val Leu Lys Gly Gly Gly Met
            500                 505                 510

Ser Ser Leu Ala Gly Lys Lys Leu Lys Glu Gly His Glu Thr Pro Met
        515                 520                 525

Asp Ile Asp Ser Asp Asp Ser Lys Ala Ala Ser Pro Pro Leu Lys Gly
    530                 535                 540

Ser Val Ser Ser Glu Ala Ser Glu Leu Asp Lys Lys Glu Lys Gly Ile

-continued

```
                545                 550                 555                 560
            Cys Val Ile Cys Met Asp Thr Ile Ser Asn Lys Lys Val Leu Pro Lys
                            565                 570                 575
            Cys Lys His Glu Phe Cys Ala Pro Cys Ile Asn Lys Ala Met Ser Tyr
                            580                 585                 590
            Lys Pro Ile Cys Pro Thr Cys Gln Thr Ser Tyr Gly Ile Gln Lys Gly
                            595                 600                 605
            Asn Gln Pro Glu Gly Ser Met Val Phe Thr Val Ser Arg Asp Ser Leu
                            610                 615                 620
            Pro Gly Tyr Glu Ser Phe Gly Thr Ile Val Ile Thr Tyr Ser Met Lys
            625                 630                 635                 640
            Ala Gly Ile Gln Thr Glu Glu His Pro Asn Pro Gly Lys Arg Tyr Pro
                            645                 650                 655
            Gly Ile Gln Arg Thr Ala Tyr Leu Pro Asp Asn Lys Glu Gly Arg Lys
                            660                 665                 670
            Val Leu Lys Leu Leu Tyr Arg Ala Phe Asp Gln Lys Leu Ile Phe Thr
                            675                 680                 685
            Val Gly Tyr Ser Arg Val Leu Gly Val Ser Asp Val Ile Thr Trp Asn
                            690                 695                 700
            Asp Ile His His Lys Thr Ser Arg Phe Gly Gly Pro Glu Met Tyr Gly
            705                 710                 715                 720
            Tyr Pro Asp Pro Ser Tyr Leu Lys Arg Val Lys Glu Glu Leu Lys Ala
                            725                 730                 735
            Lys Gly Ile Glu
                            740

<210> SEQ ID NO 11
<211> LENGTH: 2247
<212> TYPE: DNA
<213> ORGANISM: Mus musculus

<400> SEQUENCE: 11
atggcttcca gtcccgaccc gccgtccccg ctactcgtac ggctgcggga gtccatcccc         60
aaggcgcaca ggaagctcga gatatacttc cagagccggg cctcgggagg tggggagtgc        120
tctgtccagc ccgtgggccc cagcgccccg gacacctacg aggtgaagtt cctaaaaaaa        180
gcagataagg agaaagtgtt gaaaaagagc gaacacgaga tgttggtcca taacaaacct        240
gtgaccattg tcctggaaac tactaaaaag ccagtagagg acctgagacc cagactccca        300
tccttgacac agccagtgga gacaccaagc tccagacctc cgtccttgac ggggtctctg        360
gatgaagcac tttgtgatga catacatccc caggacgggc tcgtttctaa ctctgttgac        420
tcagttgtcc aaaagatctt tcttgctgtg accgctgagc tgaactgtga cctgctctct        480
aaagagcaga gagcatctat aaccactgtc tgccctcaca tcatcaaaag catggagggt        540
agtgatggaa ttaagaaggt gtgtggcaac ttcaaagata ttgaaaagat acatcacttc        600
ttgagtgagc agcttttgga acgggagcag aaacggaagg gaagcgagca gaaacggaag        660
tgcgccccac agaaacacac acctcccgat gtggagcggg agcccctga  tcagagcagt        720 attcaagttc ctgtgcttct ccttgaatat ttcaagcatg ttaatccggg tagactagag        780
ttcatagagt acaaatttgg tgtaaacatt gaaatccaag ctagttctcc caatatggtc        840
actgtaggct tcacctccag cccatttggc aacgtagaag aagcaagtca gtcctttgtc        900
agagactttc gaaatgctc  gcagtctctg agcaagatt  gtatctcttt agaggagcac        960
cagagagcaa aggaggtcag acaggagctg agtcgctgct cccaaagct  cttgataaag       1020
```

```
ggacagggaa gaacgctgac tctcctcggc tctcctgctg acatttcagc cgccacagaa    1080
aaagtctccc aaggtcttgg cctgagacct gtgaaaataa ccgcatctgg gtacacgacg    1140
ggcatcgagg tcgattcaac acgctttaag cttctagagc ctgaactgct ccaggaaatc    1200
tcagagatcg agcagaagtt taacacccgt ggcaaagtcc aggaaaaagg ccagaaaacc    1260
tgcattcttt ttgtccccaa ggataaagac ttagacctgt cagtgcagtc ctacacaggt    1320
tttactgatg ccttccagcg tgccacgtgg cagctgagga cagaagttct gtcgctgaaa    1380
gggttgggca aggagagagc tcgcttacac aataccaagt tgccgacaa  ctttaaaaaa    1440 gagcacccga atgtgcactt tgtgacatct caggagtcag tgaccttgac tggcttgcca    1500
catcaccttg cgcaggcaat gcagtatgtc tccaaaagaa tgggactggc accgtcatct    1560
ggagagaaac tcgctatgga tcaggaaacc cccatggaga tcagcagtag tgaccccat     1620 ggagatcagc aggagaatgc agccttacct gctccccgag gcacctctag cagccctgca    1680
gcttcgaagg ggactgagga ctactgtgtc atctgcatgg ataccatcag caacaagcac    1740
gtgctcccca gtgcaagca  tgaattctgc acctcgtgta tcagcaaagc catgcttatc    1800
aagcctgtct gtcctgtgtg tctgacttcc tacggcatcc agaaagggaa ccagccagag    1860
ggaaccatgt cttactccac tcaaaaaggg tcacttccag gttatgaagg ctgtggcacc    1920
attgtgatta attatgaaat aaaagatggc atccaaacaa aagagcaccc aaacccagga    1980
aaggcttatc atggaacacg gcgaactgca tacttgcctg ataatactga gggaagaaag    2040
gttttggatc tgctccacga agcctttaag cacagactga cttttcacaat aggatactct    2100 cgagcaacag gagtctcgga tgtcattaca tggaatgata ttcatcacaa acatccaag     2160 tttggaggac cagcaaattt tggctaccct gatcctgatt acctgaaacg tgtcaaggag    2220
gagctgaaag caaaaggcat tgagtaa                                       2247
```

<210> SEQ ID NO 12
<211> LENGTH: 748
<212> TYPE: PRT
<213> ORGANISM: Mus musculus

<400> SEQUENCE: 12

```
Met Ala Ser Ser Pro Asp Pro Ser Pro Leu Leu Val Arg Leu Arg
1               5                   10                  15

Glu Ser Ile Pro Lys Ala His Arg Lys Leu Glu Ile Tyr Phe Gln Ser
            20                  25                  30

Arg Ala Ser Gly Gly Gly Glu Cys Ser Val Gln Pro Val Gly Pro Ser
        35                  40                  45

Ala Pro Asp Thr Tyr Glu Val Lys Phe Leu Lys Lys Ala Asp Lys Glu
    50                  55                  60

Lys Val Leu Lys Lys Ser Glu His Glu Met Leu Val His Asn Lys Pro
65                  70                  75                  80

Val Thr Ile Val Leu Glu Thr Thr Lys Lys Pro Val Glu Asp Leu Arg
                85                  90                  95

Pro Arg Leu Pro Ser Leu Thr Gln Pro Val Glu Thr Pro Ser Ser Arg
            100                 105                 110

Pro Pro Ser Leu Thr Gly Ser Leu Asp Glu Ala Leu Cys Asp Asp Ile
        115                 120                 125

His Pro Gln Asp Gly Leu Val Ser Asn Ser Val Asp Ser Val Val Gln
    130                 135                 140

Lys Ile Phe Leu Ala Val Thr Ala Glu Leu Asn Cys Asp Leu Leu Ser
```

```
            145                 150                 155                 160
Lys Glu Gln Arg Ala Ser Ile Thr Thr Val Cys Pro His Ile Ile Lys
                    165                 170                 175
Ser Met Glu Gly Ser Asp Gly Ile Lys Lys Val Cys Gly Asn Phe Lys
                    180                 185                 190
Asp Ile Glu Lys Ile His His Phe Leu Ser Glu Gln Leu Leu Glu Arg
                    195                 200                 205
Glu Gln Lys Arg Lys Gly Ser Glu Gln Lys Arg Lys Cys Ala Pro Gln
        210                 215                 220
Lys His Thr Pro Pro Asp Val Glu Arg Glu Pro Pro Asp Gln Ser Ser
225                 230                 235                 240
Ile Gln Val Pro Val Leu Leu Leu Glu Tyr Phe Lys His Val Asn Pro
                    245                 250                 255
Gly Arg Leu Glu Phe Ile Glu Tyr Lys Phe Gly Val Asn Ile Glu Ile
                    260                 265                 270
Gln Ala Ser Ser Pro Asn Met Val Thr Val Gly Phe Thr Ser Ser Pro
                275                 280                 285
Phe Gly Asn Val Glu Glu Ala Ser Gln Ser Phe Val Arg Asp Phe Gln
            290                 295                 300
Lys Cys Ser Gln Ser Leu Lys Gln Asp Cys Ile Ser Leu Glu Glu His
305                 310                 315                 320
Gln Arg Ala Lys Glu Val Arg Gln Glu Leu Ser Arg Cys Phe Pro Lys
                    325                 330                 335
Leu Leu Ile Lys Gly Gln Gly Arg Thr Leu Thr Leu Leu Gly Ser Pro
                    340                 345                 350
Ala Asp Ile Ser Ala Ala Thr Glu Lys Val Ser Gln Gly Leu Gly Leu
                355                 360                 365
Arg Pro Val Lys Ile Thr Ala Ser Gly Tyr Thr Thr Gly Ile Glu Val
            370                 375                 380
Asp Ser Thr Arg Phe Lys Leu Leu Glu Pro Glu Leu Leu Gln Glu Ile
385                 390                 395                 400
Ser Glu Ile Glu Gln Lys Phe Asn Thr Arg Gly Lys Val Gln Glu Lys
                    405                 410                 415
Gly Gln Lys Thr Cys Ile Leu Phe Val Pro Lys Asp Lys Asp Leu Asp
                    420                 425                 430
Leu Ser Val Gln Ser Tyr Thr Gly Phe Thr Asp Ala Phe Gln Arg Ala
                435                 440                 445
Thr Trp Gln Leu Arg Thr Glu Val Leu Ser Leu Lys Gly Leu Gly Lys
            450                 455                 460
Glu Arg Ala Arg Leu His Asn Thr Lys Phe Ala Asp Asn Phe Lys Lys
465                 470                 475                 480
Glu His Pro Asn Val His Phe Val Thr Ser Gln Glu Ser Val Thr Leu
                    485                 490                 495
Thr Gly Leu Pro His His Leu Ala Gln Ala Met Gln Tyr Val Ser Lys
                    500                 505                 510
Arg Met Gly Leu Ala Pro Ser Ser Gly Glu Lys Leu Ala Met Asp Gln
                515                 520                 525
Glu Thr Pro Met Glu Ile Ser Ser Asp Pro His Gly Asp Gln Gln
            530                 535                 540
Glu Asn Ala Ala Leu Pro Ala Pro Arg Gly Thr Ser Ser Pro Ala
545                 550                 555                 560
Ala Ser Lys Gly Thr Glu Asp Tyr Cys Val Ile Cys Met Asp Thr Ile
                    565                 570                 575
```

```
Ser Asn Lys His Val Leu Pro Lys Cys Lys His Glu Phe Cys Thr Ser
            580                 585                 590

Cys Ile Ser Lys Ala Met Leu Ile Lys Pro Val Cys Pro Val Cys Leu
            595                 600                 605

Thr Ser Tyr Gly Ile Gln Lys Gly Asn Gln Pro Glu Gly Thr Met Ser
            610                 615                 620

Tyr Ser Thr Gln Lys Gly Ser Leu Pro Gly Tyr Glu Gly Cys Gly Thr
625                 630                 635                 640

Ile Val Ile Asn Tyr Glu Ile Lys Asp Gly Ile Gln Thr Lys Glu His
                645                 650                 655

Pro Asn Pro Gly Lys Ala Tyr His Gly Thr Arg Arg Thr Ala Tyr Leu
            660                 665                 670

Pro Asp Asn Thr Glu Gly Arg Lys Val Leu Asp Leu Leu His Glu Ala
            675                 680                 685

Phe Lys His Arg Leu Thr Phe Thr Ile Gly Tyr Ser Arg Ala Thr Gly
            690                 695                 700

Val Ser Asp Val Ile Thr Trp Asn Asp Ile His His Lys Thr Ser Lys
705                 710                 715                 720

Phe Gly Gly Pro Ala Asn Phe Gly Tyr Pro Asp Pro Asp Tyr Leu Lys
                725                 730                 735

Arg Val Lys Glu Glu Leu Lys Ala Lys Gly Ile Glu
            740                 745

<210> SEQ ID NO 13
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 13
gcccacgcau ggauccaaag aau                                              23

<210> SEQ ID NO 14
<211> LENGTH: 27
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 14
ggauucuuug gauccaugcg ugggccu                                          27

<210> SEQ ID NO 15
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 15
cccauaccag uucugcaaug ugg                                              23

<210> SEQ ID NO 16
<211> LENGTH: 27
<212> TYPE: RNA
<213> ORGANISM: Artificial Sequence
<220> FEATURE:
```

```
<223> OTHER INFORMATION: /note="Description of Artificial Sequence:
      Synthetic siRNA"

<400> SEQUENCE: 16
uaccacauug cagaacuggu augggac                                             27

<210> SEQ ID NO 17
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 17
ggaaguagcu cuccagcuuc cuu                                                 23

<210> SEQ ID NO 18
<211> LENGTH: 27
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 18
cgaaggaagc uggagagcua cuuccag                                             27

<210> SEQ ID NO 19
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 19
ccaaaggaag gaacgcuaac aau                                                 23

<210> SEQ ID NO 20
<211> LENGTH: 27
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 20
aaauuguuag cguuccuucc uuugguc                                             27

<210> SEQ ID NO 21
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 21
agcuaucaga gaagcuaaua aau                                                 23

<210> SEQ ID NO 22
<211> LENGTH: 27
<212> TYPE: RNA
<213> ORGANISM: Artificial Sequence
<220> FEATURE:
<223> OTHER INFORMATION: /note="Description of Artificial Sequence:
```

Synthetic siRNA"

<400> SEQUENCE: 22
uaauuuauua gcuucucuga uagcuuc       27

<210> SEQ ID NO 23
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 23
ccacuaggag aaagacaaau agg       23

<210> SEQ ID NO 24
<211> LENGTH: 27
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 24
gaccuauuug ucuuucuccu aguggcc       27

<210> SEQ ID NO 25
<211> LENGTH: 23
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 25
cccuuguaca uauaucuuua gag       23

<210> SEQ ID NO 26
<211> LENGTH: 27
<212> TYPE: RNA
<213> ORGANISM: Artificial Sequence
<220> FEATURE:
<223> OTHER INFORMATION: /note="Description of Artificial Sequence:
      Synthetic siRNA"

<400> SEQUENCE: 26
cucucuaaag auauauguac aagggug       27

<210> SEQ ID NO 27
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 27
atggactttt ccatggtggc cggag       25

<210> SEQ ID NO 28
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

-continued

```
<400> SEQUENCE: 28
ttaatcaaca gggctgccac ttg                                              23

<210> SEQ ID NO 29
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 29
gtttcagcaa gtcccataac agttctgcaa tgtggt                                36

<210> SEQ ID NO 30
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 30
accacattgc agaactgtta tgggacttgc tgaaac                                36

<210> SEQ ID NO 31
<211> LENGTH: 39
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31
gggaagagtg agctgggaca ataaaccacc ccttctttc                             39

<210> SEQ ID NO 32
<211> LENGTH: 39
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32
gaaagaaggg gtggtttatt gtcccagctc actcttccc                             39

<210> SEQ ID NO 33
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
ctagggaaga gtgagctggg acaagaaacc                                       30

<210> SEQ ID NO 34
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic primer"
```

<400> SEQUENCE: 34
accacattgc agaactgtta tgggacttgc tgaaac    36

<210> SEQ ID NO 35
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 35
ctagggaaga gtgagctggg acaagaaacc    30

<210> SEQ ID NO 36
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
ggatccatgc gtgggcctat tacatctctt ccacgttg    38

<210> SEQ ID NO 37
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
tggcagacgg cagatgtaat tgtt    24

<210> SEQ ID NO 38
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
ggatccatgc gtgggcctat tacatctctt ccacgttg    38

<210> SEQ ID NO 39
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 39
cagtctggaa agatgccctc accacacatg ctg    33

<210> SEQ ID NO 40
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 40

```
cagcatgtgt ggtgagggca tctttccaga ctg                                33
```

<210> SEQ ID NO 41
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 41

```
gtccagggcc acgctgcatg gcagacggca gatg                               34
```

<210> SEQ ID NO 42
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42

```
catctgccgt ctgccatgca gcgtggccct ggac                               34
```

<210> SEQ ID NO 43
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 43

```
atggcctccc acctgcgccc gccgtc                                        26
```

<210> SEQ ID NO 44
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 44

```
ttactcaatt cctttggctt tcagctc                                       27
```

<210> SEQ ID NO 45
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 45

```
atggcggagt cttcggataa gctc                                          24
```

<210> SEQ ID NO 46
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 46
ttaccacagg gaggtcttaa aattg    25

<210> SEQ ID NO 47
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 47
caccatggcc tcccacctgc gcccgccgtc    30

<210> SEQ ID NO 48
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 48
ctcaattcct ttggctttca gctc    24

<210> SEQ ID NO 49
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 49
acccggtcga catggacttt tccatggtgg ccggag    36

<210> SEQ ID NO 50
<211> LENGTH: 35
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 50
caccgcggcc gcttaatcaa cagggctgcc acttg    35

<210> SEQ ID NO 51
<211> LENGTH: 55
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 51
caccatggac tacaaggatg acgatgacaa gatggcggag tcttcggata agctc    55

<210> SEQ ID NO 52
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 52
ttaccacagg gaggtcttaa aattg    25

```
<210> SEQ ID NO 53
<211> LENGTH: 6
<212> TYPE: PRT
<213> ORGANISM: Artificial Sequence
<220> FEATURE:
<223> OTHER INFORMATION: /note="proline rich domain"
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 53

Xaa Pro Xaa Xaa Pro Xaa
1               5

<210> SEQ ID NO 54
<211> LENGTH: 4
<212> TYPE: PRT
<213> ORGANISM: Artificial Sequence
<220> FEATURE:
<223> OTHER INFORMATION: /note="tyrosine phosphorylation site"
<220> FEATURE:
<221> NAME/KEY: misc_feature
<222> LOCATION: (2)..(4)
<223> OTHER INFORMATION: Xaa can be any naturally occurring amino acid

<400> SEQUENCE: 54

Tyr Xaa Xaa Xaa
1

<210> SEQ ID NO 55
<211> LENGTH: 66
<212> TYPE: PRT
<213> ORGANISM: Artificial Sequence
<220> FEATURE:
<223> OTHER INFORMATION: /note="C3HC4-type zinc finger motif"
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Xaa = Ile or Val
<220> FEATURE:
<221> NAME/KEY: MISC_FEATURE
<222> LOCATION: (5)..(34)
<223> OTHER INFORMATION: Xaa at positions 5-34 may be any naturally-
     occurring amino acid and up to nineteen of them may be absent
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: VARIANT
<222> LOCATION: (39)..(39)
<223> OTHER INFORMATION: Xaa = Phe or Ile or Leu
<220> FEATURE:
<221> NAME/KEY: MISC_FEATURE
<222> LOCATION: (41)..(42)
<223> OTHER INFORMATION: Xaa at positions 41-42 may be any naturally-
```

```
                occurring amino acid and up to one of them may be absent
<220> FEATURE:
<221> NAME/KEY: VARIANT
<222> LOCATION: (44)..(44)
<223> OTHER INFORMATION: Xaa = Ile or Leu or Met
<220> FEATURE:
<221> NAME/KEY: MISC_FEATURE
<222> LOCATION: (45)..(62)
<223> OTHER INFORMATION: Xaa at positions 45-62 may be any naturally-
                occurring amino acid and up to eight of them may be absent
<220> FEATURE:
<221> NAME/KEY: misc_feature
<222> LOCATION: (65)..(65)
<223> OTHER INFORMATION: Xaa can be any naturally occurring amino acid

<400> SEQUENCE: 55

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Cys Xaa His Xaa Xaa Cys Xaa Xaa Cys Xaa Xaa Xaa Xaa Xaa
        35                  40                  45

Xaa Xaa Xaa Xaa Xaa Xaa Xaa Xaa Xaa Xaa Xaa Xaa Xaa Xaa Cys Pro
    50                  55                  60

Xaa Cys
65
```

COMPOSITIONS AND METHODS FOR THE MODULATION OF DNA DAMAGE RESPONSES USING BAL1 AND BBAP

CROSS-REFERENCE TO RELATED APPLICATIONS

This application is the U.S. National Stage Application of International Application No. PCT/US2012/058960, filed on Oct. 5, 2012, which claims the benefit of U.S. Provisional Application No. 61/543,465, filed on Oct. 5, 2011; the entire contents of each of said applications is incorporated herein in its entirety by this reference.

SEQUENCE LISTING

This application contains a Sequence Listing that sets forth the amino acid or nucleotide sequence for SEQ ID NOs: 1-55, which was submitted electronically in ASCII text file format on Aug. 26, 2014. Said electronically submitted ASCII text file, created on Jun. 4, 2014, is named "DFS-108_01_Sequence_Listing.txt" and is 71,680 bytes in size. The subject matter in the ASCII text file is incorporated herein by reference in its entirety.

STATEMENT OF RIGHTS

This invention was made with government support under grant number PO1CA092625 awarded by The National Institutes of Health. The government has certain rights in the invention.

BACKGROUND OF THE INVENTION

Cancer is a global health concern affecting millions of people. Since it represents the phenotypic end-point of multiple genetic lesions, cancer endows cells with a full range of biological properties required for tumorigenesis. This complex myriad of biological causes resulting in the same phenotype indicates that novel compositions and methods for effectively diagnosing and treating cancer are needed to combat the ineffectiveness of any given cancer therapy. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. Yet cancer cells commonly develop resistance to the chemotherapeutic agent thereby rendering a given chemotherapeutic agent or cancer therapy targeting a certain biological mechanism ineffective. Despite decades of scientific research, few effective therapies have emerged to target alternative biological pathways critical to the development of cancer. Accordingly, there is a great need to identify compositions and methods to effectively target such biological pathways.

SUMMARY OF THE INVENTION

The present invention provides methods and compositions for enhancing the efficacy of cancer therapies through modulation of BAL1 and/or BBAP. In one aspect, a method of treating cancer by enhancing the efficacy of cancer therapies in a subject, comprising administering to the subject an effective amount of (a) an agent that inhibits one or more functions of BAL1, BBAP, or a BAL1-BBAP complex and (b) the cancer therapy is provided. In one embodiment, the cancer is selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, colon cancer, melanoma, and vagina. In another embodiment, the cancer therapy is selected from the group consisting of chemotherapy, radiation therapy, immunotherapy, hormone therapy, hyperthermic, laser therapy, gene therapy, PARP inhibitor therapy, and combinations thereof (e.g., treatment with a PARP-1 inhibitor). In still another embodiment, the agent is selected from the group consisting of an antibody or an antigen binding fragment thereof, which specifically binds to a protein corresponding to BAL1, BBAP, and/or a BAL1-BBAP complex; an RNA interfering agent which inhibits expression of BAL1 and/or BBAP; an antisense oligonucleotide complementary to BAL1 and/or BBAP; a small molecule which inhibits activity of BAL1, BBAP, and/or a BAL1-BBAP complex; an aptamer which inhibits expression or activity of BAL1, BBAP, and/or a BAL1-BBAP complex; and a BAL1 and/or BBAP polypeptide described herein. In such embodiments, the antibody can be conjugated to a toxin or a chemotherapeutic agent; or the RNA interfering agent is an siRNA molecule or an shRNA molecule; or the small molecule inhibits a protein-protein interaction between BAL1 and BBAP. In yet another embodiment, the efficacy of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the subject is a human.

In another aspect, a method of enhancing the efficacy of cancer therapies in inhibiting hyperproliferation of a hyperproliferative cell in a medium, comprising applying to said medium an effective amount of (a) an agent that inhibits one or more functions of BAL1, BBAP, or a BAL1-BBAP complex and (b) the cancer therapy is provided. In one embodiment, the hyperproliferative cells are selected from the group consisting of breast cancer cells, ovarian cancer cells, transitional cell bladder cancer cells, bronchogenic lung cancer cells, thyroid cancer cells, pancreatic cancer cells, prostate cancer cells, uterine cancer cells, testicular cancer cells, gastric cancer cells, soft tissue and osteogenic sarcoma cells, neuroblastoma cells, Wilms' tumor cells, malignant lymphoma (Hodgkin's and non-Hodgkin's) cells, acute myeloblastic leukemia cells, acute lymphoblastic leukemia cells, Kaposi's sarcoma cells, Ewing's tumor cells, refractory multiple myeloma cells, and squamous cell carcinoma of the head, neck, cervix, colon cancer, melanoma, and vagina cells. In another embodiment, cancer therapy is selected from the group consisting of chemotherapy, radiation therapy, immunotherapy, hormone therapy, hyperthermic therapy, laser therapy, gene therapy, PARP inhibitor therapy, and combinations thereof (e.g., treatment with a PARP-1 inhibitor). In still another embodiment, the agent is selected from the group consisting of an antibody or an antigen binding fragment thereof, which specifically binds to a protein corresponding to BAL1, BBAP, and/or a BAL1-

BBAP complex; an RNA interfering agent which inhibits expression of BAL1 and/or BBAP; an antisense oligonucleotide complementary to BAL1 and/or BBAP; a small molecule which inhibits activity of BAL1, BBAP, and/or a BAL1-BBAP complex; an aptamer which inhibits expression or activity of BAL1, BBAP, and/or a BAL1-BBAP complex; and a BAL1 and/or BBAP polypeptide described herein. In such embodiments, the antibody can be conjugated to a toxin or a chemotherapeutic agent; or the RNA interfering agent is an siRNA molecule or an shRNA molecule; or the small molecule inhibits a protein-protein interaction between BAL1 and BBAP. In yet another embodiment, the efficacy of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the cells are human cells.

In still another aspect, a method of predicting the efficacy of a cancer therapy in a subject, comprising obtaining a biological sample from the subject, and comparing: a) the amount, structure, subcellular localization, and/or activity of at least one marker selected from the group consisting of BAL1, BBAP, and/or BAL1-BBAP complex in a subject sample; and b) the amount, structure, subcellular localization, and/or activity of the at least one marker in a control, wherein a significant difference in the amount, structure, subcellular localization, and/or activity of the at least one marker in the sample and the amount, structure, subcellular localization, and/or activity in the control is predictive of the outcome of treatment of the subject with the cancer therapy. In one embodiment, the control is selected from the group consisting of a non-cancerous cell sample from the subject or member of the same species to which the subject belongs; a non-cancerous tissue that is the same tissue type as the cancerous tissue of the subject; and a non-cancerous tissue that is not the same tissue type as the cancerous tissue of the subject. In another embodiment, the control amount, subcellular localization, structure, and/or activity is the wild type amount, subcellular localization, structure, and/or activity in the species to which the subject belongs. In still another embodiment, the subject sample is obtained before the subject has received cancer therapy or the subject sample is obtained after the subject has received cancer therapy. In yet another embodiment, the sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In another embodiment, the cancer is selected from the group consisting of breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, and squamous cell carcinomas of the head, neck, cervix, and vagina. In still another embodiment, the amount of the marker is determined by determining the level of expression or copy number of the marker. In yet another embodiment, the copy number is determined by using at least one technique selected from the group consisting of fluorescence in situ hybridization (FISH), quantitative PCR (qPCR), comparative genomic hybridization (CGH), and single-nucleotide polymorphism (SNP) array. In another embodiment, an increased copy number in the subject sample indicates reduced efficacy of the cancer therapy and a decreased copy number in the subject sample indicates increased efficacy of the cancer therapy, thereby predicting the efficacy of the cancer therapy in the subject. In still another embodiment, the level of expression of the marker in the sample is assessed by detecting the presence in the sample of a protein corresponding to the marker (e.g., by using a reagent selected from the group consisting of an antibody, an antibody derivative, and an antibody fragment). In yet another embodiment, the level of expression of the marker in the sample is assessed by detecting the presence in the sample of a transcribed polynucleotide (e.g., mRNA or cDNA) or portion thereof, wherein the transcribed polynucleotide comprises the marker. In another embodiment, determining the level of expression of the marker comprises the use of at least one technique selected from the group consisting of Northern blot analysis, reverse transcriptase PCR, real-time PCR, RNAse protection, and microarray analysis. In still another embodiment, the level of expression of the marker in the sample is assessed by detecting the presence in the sample of a transcribed polynucleotide which anneals with the marker or anneals with a portion of a polynucleotide wherein the polynucleotide comprises the marker, under stringent hybridization conditions. In yet another embodiment, the significant difference is an increase in the amount, structure, subcellular localization, and/or activity of the marker in the subject sample relative to the control, indicating a reduced likelihood of efficacy of the cancer therapy in the subject. In another embodiment, the significant difference is a decrease in the amount, structure, subcellular localization, and/or activity of the marker in the subject sample relative to the control, indicating an increased likelihood of efficacy of the cancer therapy in the subject. In still another embodiment, the efficacy of treatment is measured by at least one criteria selected from the group consisting of survival until mortality, pathological complete response, clinical complete remission, clinical partial remission, clinical stable disease, recurrence-free survival, metastasis free survival, and disease free survival. In yet another embodiment, cancer therapy is selected from the group consisting of chemotherapy, radiation therapy, immunotherapy, hormone therapy, hyperthermic therapy, laser therapy, gene therapy, PARP inhibitor therapy, and combinations thereof (e.g., treatment with a PARP-1 inhibitor).

In yet another aspect, the present invention provides a use of an agent that that inhibits one or more functions of BAL1, BBAP, or a BAL1-BBAP complex for the preparation of a medicament for enhancing the efficacy of a cancer therapy in a subject. In one embodiment, the one or more functions of BAL1, BBAP, or a BAL-BBAP complex is inhibited using an agent selected from the group consisting of an anti-BAL1 and/or anti-BBAP antisense nucleic acid molecule; an anti-BAL1 and/or anti-BBAP RNA interference molecule; a blocking anti-BAL1, anti-BBAP, and/or anti-BAL1-BBAP antibody; a non-activating form of BAL1, BBAP, or a BAL1-BBAP polypeptide or fragment thereof; and a small molecule that binds to BAL1, BBAP, or a BAL1-BBAP. In another embodiment, the use further comprises contacting the cell with an additional cancer therapeutic agent.

In another aspect, a method for assessing the efficacy of an agent that modulates the expression and/or activity of BAL1, BBAP, or a BAL-BBAP complex for enhancing the efficacy of a cancer therapy in a subject comprising a) detecting in a subject sample at a first point in time, the expression and/or activity of BAL1, BBAP, or a BAL-BBAP complex; b) repeating step a) during at least one subsequent point in time after administration of the agent; and c) comparing the expression and/or activity detected in steps a) and b), wherein a significantly higher expression and/or activity of BAL1, BBAP, or a BAL-BBAP complex expression and/or activity in the first subject sample relative to at least one subsequent subject sample, indicates that the agent enhances the efficacy of the cancer therapy in the subject and/or wherein a significantly decreased amount of an activity selected from the group consisting of a) increased binding to a BAL1 polypeptide or fragment thereof; b) increased binding of a BBAP polypeptide or fragment thereof; c) increased formation of a BAL1-BBAP complex; d) inhibition of localization and/or binding of BAL1 and/or BBAP to DNA damage sites; e) inhibition of binding of BAL1 to poly(ADP-ribose) (PAR) chains; f) inhibition of BBAP monoubiquitylation of histones; g) inhibition of BBAP-mediated methylation of histones; h) inhibition of localization and/or binding to DNA damage sites of at least one polypeptide selected from the group consisting of 53 BP1, RAP80, BRCA1, ATM, γH2AX, and MDC1; and i) inhibition of DNA damage responses (DDR); in the first subject sample relative to at least one subsequent subject sample, indicates that the test agent enhances the efficacy of the cancer therapy in the subject is provided. In one embodiment, the agent is selected from the group consisting of an anti-BAL1 and/or anti-BBAP antisense nucleic acid molecule; an anti-BAL1 and/or anti-BBAP RNA interference molecule; a blocking anti-BAL1, anti-BBAP, and/or anti-BAL1-BBAP antibody; a non-activating form of BAL1, BBAP, or a BAL1-BBAP polypeptide or fragment thereof; and a small molecule that binds to BAL1, BBAP, or a BAL1-BBAP. In another embodiment, the subject has undergone cancer therapy treatment, has completed cancer therapy treatment, and/or is in remission from the cancer between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of a cancer. In another embodiment, the first and/or at least one subsequent sample is selected from the group consisting of tissue, whole blood, serum, plasma, buccal scrape, saliva, cerebrospinal fluid, urine, stool, and bone marrow. In still another embodiment, the first and/or at least one subsequent sample is a portion of a single sample or pooled samples obtained from the subject. In yet another embodiment, a significantly modulated expression and/or activity comprises modulating the expression and/or activity by at least 25% relative to the second sample.

In still another aspect, an isolated nucleic acid molecule selected from the group consisting of a) an isolated nucleic acid molecule which encodes at least one BBAP binding domain of a BAL1 protein and which does not encode full-length BAL1; b) an isolated nucleic acid molecule which encodes at least one BBAP binding domain of a BAL1 protein and which does not encode one or more functional domain(s) of a BAL1 protein selected from the group consisting of Macro 1, Macro 2, and PARP domains; c) an isolated nucleic acid molecule which encodes a polypeptide comprising an amino acid sequence having at least 70% identity to the amino acid sequence of 453-702 of SEQ ID NO:2 and which does not encode full-length BAL1 and/or which does not encode one or more functional domain(s) of a BAL1 protein selected from the group consisting of Macro 1, Macro 2, and PARP domains; d) an isolated nucleic acid molecule which encodes a polypeptide consisting essentially of an amino acid sequence having at least 70% identity to the amino acid sequence of 453-702 of SEQ ID NO:2 and which does not encode full-length BAL1 and/or which does not encode one or more functional domain(s) of a BAL1 protein selected from the group consisting of Macro 1, Macro 2, and PARP domains; e) an isolated nucleic acid molecule which encodes at least one BAL1 binding domain of a BBAP protein and which does not encode full-length BBAP; f) an isolated nucleic acid molecule which encodes at least one BAL1 binding domain of a BBBAP protein and which does not encode one or more functional domain(s) of a BBAP protein selected from the group consisting of BBAP dimerization and RING domains; g) an isolated nucleic acid molecule which encodes a polypeptide comprising an amino acid sequence having at least 70% identity to the amino acid sequence of 423-617 of SEQ ID NO:10 and which does not encode full-length BBAP and/or which does not encode one or more functional domain(s) of a BBAP protein selected from the group consisting of BBAP dimerization and RING domains; and h) an isolated nucleic acid molecule which encodes a polypeptide consisting essentially of an amino acid sequence having at least 70% identity to the amino acid sequence of 423-617 of SEQ ID NO:10 and which does not encode full-length BBAP and/or which does not encode one or more functional domain(s) of a BBAP protein selected from the group consisting of BBAP dimerization and RING domains, as well as isolated nucleic acid molecules comprising a nucleotide sequence which is complementary to such nucleic acid sequences, is provided. In one embodiment, the isolated nucleic acid molecules further comprise a nucleic acid sequence encoding a heterologous polypeptide (e.g., a signal peptide, a peptide tag, a dimerization domain, an oligomerization domain, an antibody, or an antibody fragment).

In yet another aspect, vectors (e.g., an expression vector) comprising isolated nucleic acid molecules described herein are provided.

In another aspect, host cells transfected with a vector described herein are provided.

In still another aspect, a method of producing a polypeptide comprising culturing host cells described herein in an appropriate culture medium to thereby produce the polypeptide are provided. In one embodiment, the host cell is selected from the group consisting of a bacterial cell, a eukaryotic cell, and a cell genetically engineered to express a selectable marker. In another embodiment, the method further comprises the step of isolating the polypeptide from the medium or host cell.

In yet another aspect, an isolated polypeptide selected from the group consisting of a) an isolated polypeptide fragment of a BAL1 protein comprising at least one BBAP binding domain and is not full-length BAL1; b) an isolated polypeptide fragment of a BAL1 protein comprising at least one BBAP binding domain and which lacks one or more functional domain(s) selected from the group consisting of Macro 1, Macro 2, and PARP domains; c) an isolated polypeptide comprising an amino acid sequence that is at least 70% identical to the amino acid sequence of residues 453-702 of SEQ ID NO:2 and is not full-length BAL1 and/or which lacks one or more functional domain(s) of a BAL1 protein selected from the group consisting of Macro 1, Macro 2, and PARP domains; d) an isolated polypeptide consisting essentially of an amino acid sequence that is at least 70% identical to the amino acid sequence comprising residues 453-702 of SEQ ID NO:2 and is not full-length BAL1 and/or which lacks one or more functional domain(s) of a BAL1 protein selected from the group consisting of Macro1, Macro 2, and PARP domains; e) an isolated polypeptide fragment of a BBAP protein which is encoded by a nucleic acid molecule comprising a nucleotide sequence encoding at least one BBAP binding domain and does not encode full-length BAL1; f) an isolated polypeptide fragment of a BAL1 protein which is encoded by a nucleic acid molecule comprising a nucleotide sequence encoding at least one BBAP binding domain and which does not encode one or more functional domain(s) selected from the group consisting of Macro1, Macro 2, and PARP domains; g) an isolated polypeptide which is encoded by a nucleic acid molecule comprising a nucleotide sequence encoding an amino acid sequence that is at least 70% identical to the amino acid sequence of residues 453-702 of SEQ ID NO:2 and which does not encode full-length BAL1 and/or which does not encode one or more functional domain(s) of a BAL1 protein selected from the group consisting of Macro 1, Macro 2, and PARP domains; h) an isolated polypeptide which is encoded by a nucleic acid molecule consisting essentially of a nucleotide sequence encoding an amino acid sequence that is at least 70% identical to the amino acid sequence of residues 453-702 of SEQ ID NO:2 and does not encode full-length BAL1 and/or does not encode one or more functional domain(s) of a BAL1 protein selected from the group consisting of Macro1, Macro 2, and PARP domains; i) an isolated polypeptide fragment of a BBAP protein comprising at least one BAL1 binding domain and is not full-length BBAP; j) an isolated polypeptide fragment of a BBAP protein comprising at least one BAL1 binding domain and which lacks one or more functional domain(s) selected from the group consisting of BBAP dimerization and RING domains; k) an isolated polypeptide comprising an amino acid sequence that is at least 70% identical to the amino acid sequence of residues 423-617 of SEQ ID NO:10 and is not full-length BBAP and/or which lacks one or more functional domain(s) of a BBAP protein selected from the group consisting of BBAP dimerization and RING domains; l) an isolated polypeptide consisting essentially of an amino acid sequence that is at least 70% identical to the amino acid sequence comprising residues 423-617 of SEQ ID NO:10 and is not full-length BBAP and/or which lacks one or more functional domain(s) of a BBAP protein selected from the group consisting of BBAP dimerization and RING domains; m) an isolated polypeptide fragment of a BBAP protein which is encoded by a nucleic acid molecule comprising a nucleotide sequence encoding at least one BAL1 binding domain and does not encode full-length BBAP; n) an isolated polypeptide fragment of a BBAP protein which is encoded by a nucleic acid molecule comprising a nucleotide sequence encoding at least one BAL1 binding domain and which does not encode one or more functional domain(s) selected from the group consisting of BBAP dimerization and RING domains; o) an isolated polypeptide which is encoded by a nucleic acid molecule comprising a nucleotide sequence encoding an amino acid sequence that is at least 70% identical to the amino acid sequence of residues 423-617 of SEQ ID NO:10 and which does not encode full-length BBAP and/or which does not encode one or more functional domain(s) of a BBAP protein selected from the group consisting of BBAP dimerization and RING domains; and p) an isolated polypeptide which is encoded by a nucleic acid molecule consisting essentially of a nucleotide sequence encoding an amino acid sequence that is at least 70% identical to the amino acid sequence of residues 423-617 of SEQ ID NO:0 and does not encode full-length BBAP and/or does not encode one or more functional domain(s) of a BBAP protein selected from the group consisting of BBAP dimerization and RING domains is provided. In one embodiment, the isolated polypeptide maintains the ability to promote one or more biological activities selected from the group consisting of a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR). In another embodiment, the isolated polypeptide contains one or more conservative amino acid substitutions. In still another embodiment, the isolated polypeptide further comprises a heterologous polypeptide. In yet another embodiment, a composition comprising the isolated polypeptide is provided and the composition can contain, for example, a pharmaceutically acceptable agent selected from the group consisting of excipients, diluents, and carriers. In another embodiment, the isolated polypeptide is immobilized on an object selected from the group consisting of a cell, a metal, a resin, a polymer, a ceramic, a glass, a microelectrode, a graphitic particle, a bead, a gel, a plate, an array, and a capillary tube.

In another aspect, an isolated antibody or antigen binding portion thereof that specifically binds to a polypeptide described herein is provided. In one embodiment, the isolated antibody or antigen binding portion thereof is a monoclonal antibody, polyclonal antibody, chimeric antibody, humanized antibody, single-chain antibody, antibody fragment, or is detectably labeled.

In still another aspect, a method of making an isolated hybridoma which produces an antibody that specifically binds to a polypeptide described herein is provided, wherein the method comprises a) immunizing a mammal using a composition comprising said polypeptide or a nucleic acid molecule encoding said polypeptide; b) isolating splenocytes from the immunized mammal; c) fusing the isolated splenocytes with an immortalized cell line to form hybridomas; and d) screening individual hybridomas for production of an antibody which specifically binds with said polypeptide thereof to isolate the hybridoma. In one embodiment, an antibody produced by such a hybridoma is provided herein.

In yet another aspect, a method for detecting the presence of a polypeptide of claim 62 in a sample comprising a) contacting the sample with a compound which selectively binds to the polypeptide; and b) determining whether the compound binds to the polypeptide in the sample to thereby detect the presence of the polypeptide in the sample is provided. In one embodiment, the compound which binds to the polypeptide is an antibody.

In another aspect, a non-human animal model engineered to express a polypeptide described herein is provided. In one embodiment, the polypeptide is overexpressed. In another embodiment, the animal is a knock-in or a transgenic animal. In still another embodiment, the animal is a rodent.

In still another aspect, a cell-free assay for screening for compounds which bind to a polypeptide described herein or biologically active portion thereof described herein with a test compound and determining the ability of the test compound to bind to the polypeptide or biologically active portion thereof is provided. In one embodiment, the binding of the test compound to the polypeptide or biologically active portion thereof is detected by a method selected from the group consisting of a) detection of binding by direct detection of test compound/polypeptide binding; b) detection of binding using a competition binding assay; and c) detection of binding using an assay for measuring activity and/or expression of BAL1, BBAP, and/or a BAL1-BBAP complex.

In yet another aspect, a method for identifying a compound which binds to a polypeptide described herein or biologically active portion thereof described herein comprising a) contacting the polypeptide or biologically active portion thereof, or a cell expressing the polypeptide or biologically active portion thereof, with a test compound; and b) determining whether the polypeptide or biologically active portion thereof binds to the test compound is provided. In one embodiment, the binding of the test compound to the polypeptide or biologically active portion thereof is detected by a method selected from the group consisting of a) detection of binding by direct detection of test compound/polypeptide binding; b) detection of binding using a competition binding assay; and c) detection of binding using an assay for measuring activity and/or expression of BAL1, BBAP, and/or a BAL1-BBAP complex.

In another aspect, an isolated protein complex comprising (a) a BAL1 polypeptide described herein and (b) a BBAP polypeptide described herein is provided. In one embodiment, the BAL1 polypeptide comprises an amino acid sequence having at least about 70% identity to the amino acid sequence of SEQ ID NO:2. In another embodiment, the BBAP polypeptide comprises an amino acid sequence having at least about 70% identity to the amino acid sequence of SEQ ID NO:10. In still another embodiment, the complex is at least about 75% pure by weight as compared to the weight of the total protein in the sample. In yet another embodiment, at least one polypeptide or fragment thereof of the complex is a fusion protein and/or is labeled. In another embodiment, the complex is generated within a host cell. In still another embodiment, two or more polypeptides within the complex are covalently linked.

In still another aspect, a composition comprising an isolated protein complex described herein is provided.

In yet another aspect, an isolated antibody that has a higher binding affinity for an isolated protein complex described herein than for the uncomplexed polypeptides of the complex is provided.

In another aspect, a method for identifying a compound that modulates a BAL1-BBAP protein complex comprising (a) contacting a protein complex comprising (i) a BAL1 polypeptide and a polypeptide of claim 62 or (ii) a BBAP polypeptide and a polypeptide of claim 62, with a test compound; and (b) assaying the amount or activity of the complex, wherein a change in the amount or activity of the complex in the presence of the test compound as compared to the amount or activity of the complex in the absence of the test compound is indicative of a compound that modulates a BAL1-BBAP protein complex is provided. In one embodiment, activity of the BAL1-BBAP protein complex is selected from the group consisting of a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR).

BRIEF DESCRIPTION OF FIGURES

FIGS. 1A and 1B show GFP-BAL1 (FIG. 1A) and GFP-BBAP (FIG. 1B) recruitment to sites of laser microirradiation. Hela cells were transfected with GFP-BAL1 or BBAP, laser micro-irradiated and subsequently analyzed at serial timepoints for GFP-fluorescence in the DNA damage site (representative photos, left, kinetics of recruitment, right). Variations in fluorescence intensity (I) were plotted as a function of time (t). GFP levels at each time point were determined by averaging values from 10 cells (+standard error) from a representative experiment. FIG. 1C shows the kinetics of endogenous BAL1 recruitment to laser-induced DNA breaks. Endogenous BAL1 is shown at the top; DAPI is shown in the middle; and merged images are shown at the bottom. Images were obtained at baseline (0) and at serial timepoints (0.25-60 min) following laser microirradiation. FIG. 1D shows endogenous BBAP localization to laser-induced DNA breaks (0, 1 and 4 min) FIG. 1E shows the kinetics of BAL1 foci formation following γ-irradiation. Hela cells were treated with low-dose (100 cGy) irradiation and analyzed for BAL1 foci at baseline and at serial timepoints (0.5-60 min) thereafter.

FIGS. 3A and 3B shows the co-localization of PARP1, PAR, and BAL1 (FIG. 3A) or PARP1, PAR and BBAP (FIG. 3B) at laser-induced DNA breaks (2 min following laser microirradiation). FIG. 3C shows co-localization of BAL1 and PAR foci in γ-irradiated cells. Hela cells were treated with low-dose irradiation (100 cGy) and analyzed for BAL1 and PAR foci at baseline and at serial timepoints (0.5-60 min) thereafter. BAL1 is shown at the top; PAR is shown in the middle; and merged images are shown at the bottom. FIG. 3D shows co-immunoprecipitation of PAR n-proteins and BAL1. Hela cells were untreated or treated with low-dose Dox (50 ng) for 10 min with or without PJ-34 pretreatment. Cell lysates were immunoprecipitated (IP) with anti-PARP1, anti-BAL1 or control IgG and immunoblotted with anti-PARP1, -PAR, -BAL1 or -BBAP antibodies. Input whole cell lysates (left panel) were similarly analyzed and immunoblotted for actin as a loading control. Molecular weight markers are shown at the right. FIG. 3E shows the recruitment of GFP-tagged PARP1, BAL1 and BBAP to laser-induced breaks in control cells or cells pretreated with the PARP inhibitor, PJ-34 (2 min following laser microirradiation). FIG. 3F shows the kinetics of GFP-BAL1 recruitment to laser-induced DNA breaks in control or PJ-34 pre-treated cells. GFP-BAL1 levels at each time point were determined by averaging values from 10 cells (+standard error) in a representative experiment.

FIG. 4A shows co-immunoprecipitation of PAR-n-protein and BAL1 (see FIG. 2D for construct details). Hela cells were untreated or treated with low-dose Dox (50 ng) for 10 min with or without PJ-34 pretreatment. Cell lysates were immunoprecipitated (IP) with anti-PARP1, anti-BAL1 or control IgG and immunoblotted with anti-PARP1, -PAR, -BAL1 or -BBAP antibodies. Input whole cell lysates (left panel) were similarly analyzed and immunoblotted for actin as a loading control. Molecular weight markers are shown at the right. FIG. 4B shows scanning densitometric analysis results of PARP1 immunoprecipitates in untreated cells and cells treated with Dox alone or Dox following PJ-34 pretreatment. PARP1 is shown in the left box. BAL1 co-immunoprecipitated with PARP1 is shown in the middle box. BBAP is shown in the right box. There was only a modest increase in PARP1 immunoprecipitated following Dox treatment (1× control, 1.2× Dox-treated cells). In contrast, there was a 4.8 fold increase in BAL1 and a 1.8× increase in BBAP co-immunoprecipitated with PARP1 in Dox-treated cells. In addition, chemical PARP inhibition (PJ-34 pretreatment) decreased the coimmunoprecipitation of BAL1 and BBAP with PARP1 in Dox-treated cells. FIG. 4C shows recombinant GST-tagged BAL1 proteins (BAL1 full length and DM [IE-AA and D126A] mutants (see FIG. 1F for construct details). Proteins were synthesized, size-fractionated by NuPAGE and analyzed by Coomassie Blue staining. FIG. 4D shows FLAG-tagged PARP1. FLAG-tagged PARP1 (M2) was purified from whole cell lysate (WL), size-fractionated by NuPAGE and analyzed by Coomassie Blue staining FIG. 4E shows immunoblotting of PAR-n-proteins following PARP1 activation in vitro. In vitro assays included ~200 ng purified FLAG-tagged PARP1 and 0, 0.5 or 1 mM NAD+. Assays were performed in the presence (+) or absence (−) of the PARP inhibitor, PJ-34. Thereafter, samples were size-fractionated and immunoblotted with anti-PARP1 and anti-PAR antibodies. FLAG-tagged PARP1 was ADP-ribosylated in a dose-dependent manner by NAD+. This enzymatic activity was inhibited by PJ-34, confirming its specificity. FIG. 4F shows pulldown of PAR-n-FLAG-tagged PARP1 by GST-BAL1. GST-BAL1 (1 µg) was immobilized on glutathione-sepharose 4B beads and incubated with products of in vitro PARP1 activation (+ or −NAD+, as in FIG. 4E). After multiple washes, GST-BAL1 bound proteins were size-fractionated and immunoblotted with anti-PAR and anti-PARP1 antibodies (upper and lower panels, respectively). The products of the in vitro PARP1 assay (Input, + or −NAD+) were similarly analyzed. GST-tagged BAL1 selectively pulled down PAR-modified PARP1 but did not bind unmodified PARP1 protein. FIG. 4G shows pulldown of PAR-n-FLAG-tagged PARP1 by GST-BAL1 mutants. Assays including GST-BAL1, or -BAL1 DM were performed as in FIG. 4F. GST-tagged BAL1 pulled down PAR-modified PARP1 in a macro domain-dependent manner.

FIG. 5A shows recruitment of endogenous PARP1, PAR, BAL1 and BBAP to laser-induced breaks in control or PJ-34 pre-treated cells (2 min following laser microirradiation). FIG. 5B shows depletion of PARP1, BAL1 and BBAP in Hela cells. FIG. 5C shows recruitment of BAL1, PARP1, BBAP and PAR to laser-induced breaks in control cells or cells depleted of PARP1, BAL1 or BBAP (2 min following laser microirradiation).

FIG. 7A shows that BAL1 depletion augments the cellular response to DNA damaging agents. Hela cells were transfected with control or BAL1 siRNAs (siRNA#1, #2), treated with Dox at 50 ng/ml, 200 ng/ml, or left untreated for 1-96 hrs and subsequently evaluated by MTS assay. The consequences of BAL1 depletion were most striking in cells treated with low-dose Dox (50 ng) ($p<0.001$, two-way ANOVA). After 72 hr of treatment with low-dose Dox (50 ng), cellular proliferation (as assessed by MTS assay) was ~70-80% lower in BAL1-depleted cells than in control RNAi or parental cells. FIG. 7B shows cellular apoptosis following BAL1 depletion and Dox treatment. Parental, control and BAL1 siRNA-transfected Hela cells were untreated or treated with Dox at 50 ng/ml and 200 ng/ml for 24 hrs and analyzed for apoptosis with Annexin V/PI staining. Error bars shown in FIG. 7A-7B represent the standard deviation (SD) of the mean for three replicates in a representative experiment. FIG. 7C shows the recruitment of GFP-control, GFP-BAL1 or GFP BAL1DM to laser-induced breaks in (5' UTR-specific) BAL1 siRNA knockdown cells. Panels a-c) show GFP-control, GFP-BAL1, and GFP-BAL1DM; panels d-f) show PARP-1 in these cells; panels g-i) show merged images. FIG. 7D shows apoptosis of BAL1-depleted Hela cells depleted with GFP-control, GFP-BAL1 or GFP-BAL1DM and subsequently treated with doxorubicin (50 nM) or left untreated. Apoptosis was assessed with Annexin V/PI staining. Error bars represent the SD of the mean for 3 replicates in a representative experiment.

FIG. 9A shows PARP1 localization and ubiquitylation (conjugated ubiquitin, FK2 immunostaining) at laser-induced breaks in control or PJ-34 pre-treated Hela cells. FIGS. 9B-9C show BBAP (FIG. 9B) and RNF8 (FIG. 9C) recruitment in cells treated as in FIG. 9A. Assays were performed as in FIG. 7 and analyzed at serial timepoints following laser microirradiation (baseline [0] and 5-60 min).

FIG. 10A shows recruitment of PARP1, ATM and MDC1 to laser-induced breaks in control or PJ-34 pretreated cells (5 min following laser microirradiation). FIG. 10B shows depletion of ATM or MDC1 following siRNA. Hela cells treated with a scrambled control (SC) or ATM or MDC1 siRNA were lysed, size-fractionated and immunoblotted with the respective antibodies and actin (as a loading control). FIG. 10C shows recruitment of BAL1 and PARP1 to laser-induced breaks in control cells or cells depleted of ATM or MDC1. Assays were performed and analyzed at serial timepoints following laser microirradiation (baseline [0] and 1-9 min).

FIG. 11C shows depletion of BBAP or RNF8 following siRNA. Hela cells treated with a scrambled control (SC) or BBAP or RNF8 siRNA were lysed, size-fractionated and immunoblotted with the respective antibodies and actin (as a loading control). Comet tail moment (% DNA in tail X tail length) determined for 50-100 cells/condition using TriTek Comet Score™ software (bar graphs [mean+/−SD] is shown above and representative photographs are shown below). Data are from one of three similar experiments.

FIG. 12A show recruitment of PARP1 and 53BP1 to laser-induced breaks in control or PJ-34 treated cells. Images were obtained at baseline (0) and 10-45 30 min following laser microirradiation. FIG. 12B show PARP1 and 53BP1 recruitment to laser-induced breaks in control cells or cells depleted of PARP1, BAL1 or BBAP (via siRNA) (20 min following laser microirradiation). FIGS. 12C-12F show the kinetics of 53BP1 and H2AX foci formation following γ-irradiation of control or PJ-34-treated cells (FIGS. 12C-12D) or control siRNA or BAL1 siRNA treated cells (FIG. 12E-12F). Cells were treated with PJ-34 or vehicle alone (FIG. 12C-12D) or control siRNA or BAL1 siRNA (FIGS. 12E-12F), subjected to low-dose (100 cGy) irradiation and analyzed for 53BP1 and γH2AX foci at baseline and 1-60 min thereafter. FIGS. 12C and 12E show the percentage of cells with >10 foci/nuclei at each time point and condition. Error bars represent the standard deviation (SD) of the mean for 3 independently stained slides for each time point and condition. At the earliest timepoints following irradiation (0-4 min), the development of repair foci (percent of cells with >10 foci/nucleus) was compared in control vs. PJ-34-treated cells and control siRNA vs. BAL siRNA-treated cells with an ANOVA. FIGS. 12D and 12F show 53BP1 at the top; γH2AX in the middle; and merged images at the bottom.

FIG. 14C shows recruitment of PARP1, RAP80 (left panel) and BRCA1 (right panel) to laser-induced breaks in control cells (panels a-f) or cells depleted of PARP1 (panels g-l), BAL1 (panels m-r) or BBAP (panels s-x) (via siRNA) (10 min following laser microirradiation). FIG. 13D shows that DNA-damage induced ubiquitylation and recruitment of 53BP1 and RAP80/BRCA1 occurs via an early PARP1, BAL1 and BBAP-dependent pathway and a later phosphorylation-dependent ATM/MDC1/RNF8-associated route.

FIGS. 14A-14D show the kinetics of recruitment of RAP80/BRCA1 and PARP1 to laser-induced breaks. RAP80 (FIG. 14A-14B) or BRCA1 (FIGS. 14C-14D) and PARP1 localization in laser-induced breaks in control cells (FIGS. 14A and 14C) or cells depleted of BAL1 (via siRNA) (FIGS. 14B and 14D). Assays were performed as in FIG. 12 and analyzed at serial timepoints following laser microirradiation (baseline [0] and 5-60 min).

BRIEF DESCRIPTION OF THE TABLES

Figure 1:
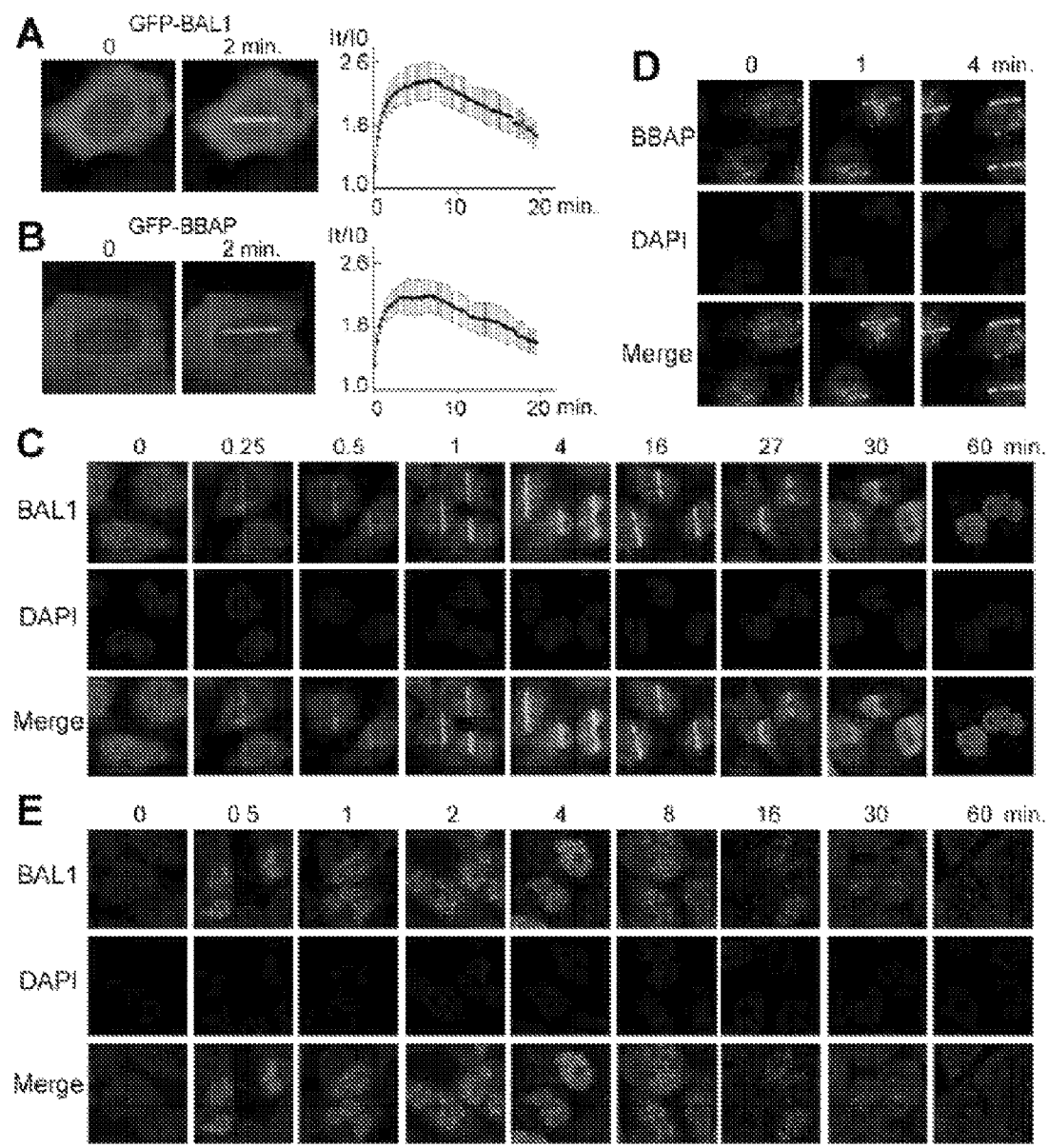
FIGS. 1A-1E show that BAL1 and BBAP are recruited to DNA damage sites.

Table 1 shows a list of representative BAL1 and BBAP nucleic acid and amino acid sequences from various organisms.

Table 2 shows a list of siRNA sequences used to knockdown BAL1, PARP1, ATM, MDC1, and RNF8 expression.

Table 3 shows sequences of oligonucleotides and primers used to generate various constructs, including GFP-BAL1, GFP-BBAP, and GFP-PARP1 constructs.

Table 4 shows sequences of oligonucleotides and primers used to generate recombinant BBAP, BAL1, and PARP1 proteins in E. coli.

DETAILED DESCRIPTION OF THE INVENTION

The present invention is based in part on the discovery that the macro domain-containing protein, BAL1, and BBAP, its natural binding partner and an E3 ligase, link PARP1 activation, ubiquitylation, and DNA repair. It is demonstrated herein that BAL1 and BBAP are overexpressed in chemotherapy-resistant cancer cells (e.g., lymphoma cells) and that BAL1 localizes to DNA damage sites by binding to PARP1-generated poly(ADP-ribose) (PAR) chains, recruits BBAP to generate a BAL1-BBAP protein complex, and thus localizes BBAP to DNA damage sites. It is further demonstrated that BBAP initiates the recruitment of early-stage DNA damage repair (DDR) factors, such as 53BP1, RAP80, and BRCA1, independent of the ATM/MDC1 DNA repair pathway in part, by selectively ubiquitylating and modulating methylation of nucleosomes at histone H4. Accordingly, the methods and compositions described herein are capable of enhancing the efficacy of cancer therapies by disrupting DDR mechanisms in cancer cells via modulation of the amount and/or activity of BAL1, BBAP, and/or BAL1-BBAP complexes. In addition, methods and compositions are described herein to identify agents useful for modulating the amount and/or activity of BAL1, BBAP, and/or BAL1-BBAP complexes, methods and compositions are also provided for predicting cancer therapy.

In order that the present invention may be more readily understood, certain terms are first defined. Additional definitions are set forth throughout the detailed description.

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., BAL1 polypeptide or fragment thereof or BBAP polypeptide or fragment thereof or BAL1-BBAP complexes). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) Science 242: 423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein. Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The term "BAL" refers to a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. For example, BAL family members encode nuclear proteins with multiple N-terminal macro domains (MACRO) and a C-terminal poly(ADP-ribose) polymerase (PARP) domain (Aguiar et al. (2005) *J. Biol. Chem.* 280: 33756-33765). Macro domains are so named because of their original identification in the variant histone, histone macroH2A. In a positioned nucleosome, the macro domain of histone macroH2A interferes with transcription factor binding, whereas the histone sequences disrupts SWI/SWF nucleosome remodeling (Angelov et al. (2003) *Mol. Cell.* 11:1033-1041). Without being bound by theory, BAL macro domain-containing proteins are believed to function like histone macroH2A by sterically blocking the access of transcription factors and co-activators to specific chromatin regions. BAL1 and two additional family members, BAL2 and BAL3, are the only known proteins with multiple N-terminal macro domains (Aguiar et al. (2000) *Blood* 96:4328-4334 and Aguiar et al. (2005) *J. Biol. Chem.* 280:33756-33765). BAL family members also include C-terminal regions with similarities to the PARP catalytic domain and BAL2 and 3, but not BAL1, which catalyze ADP ribosylation (Aguiar et al. (2005) *J. Biol. Chem.* 280:33756-33765 and Hottiger et al. (2010) *Trends Biochem. Sci.* 35:208-219).

In addition, the family of BAL proteins comprise at least one "proline rich domain." As used herein, the term "proline rich domain" includes an amino acid sequence of about 4-6 amino acid residues in length having the general sequence X-Pro-X-X-Pro-X (where X can be any amino acid) (SEQ ID NO: 53). Proline rich domains are usually located in a helical structure and bind through hydrophobic interactions to SH3 domains. SH3 domains recognize proline rich domains in both forward and reverse orientations. Proline rich domains are described in, for example, Sattler M. et al., *Leukemia* (1998) 12:637-644, the contents of which are incorporated herein by reference. BAL proteins of the invention preferably include at least one proline rich domain, but may contain two or more. Amino acid residues 781-786 of the human BAL and amino acid residues 748-753 of the murine BAL comprise proline rich domains. In addition, BAL protein family members can be identified based on the presence of at least one "tyrosine phosphorylation site" in the protein or corresponding nucleic acid molecule. As used herein, the term "tyrosine phosphorylation site" includes an amino acid sequence of about 4 amino acid residues in length having the general sequence Tyr-X-X-X (where X can be any amino acid) (SEQ ID NO: 54). The tyrosine in this domain is phosphorylated in response to a cellular stimulus, for example, in response to a hematopoietic growth factor (e.g., thrombopoietin, erythropoietin, or steel factor) stimulation. Tyrosine phosphorylation of cellular proteins plays a major role in cell signaling, e.g., hematopoietic cell signaling. Tyrosine phosphorylation sites are described in, for example, Sattler M. et al., *Leukemia* (1998) 12:637-644, the contents of which are incorporated herein by reference. BAL proteins of the invention include at least one or two tyrosine phosphorylation sites, but may contain three or more. Amino acid residues 392-395 and 495-498 of the human BAL comprise tyrosine phosphorylation sites. It is to be noted that the term can further be used to refer to any combination of features described herein regarding BAL molecules. For example, any combination of sequence composition, percentage identify, sequence length, domain structure, functional activity, etc. can be used to describe a BAL molecule of the present invention.

The related term "BAL1" refers to a specific BAL family member originally named B-aggressive lymphoma 1 (BAL1) due to its overexpression in diffuse large B-cell lymphomas (DLBCL) (Aguiar et al. (2000) *Blood* 96:4328-4334 and Takeyama et al. (2003) *J. Biol. Chem.* 278:21930-21937). The term is intended to include fragments, variants (e.g., allelic variants) and derivatives thereof. At least six splice variants encoding three human Ball isoforms exist.

The sequence of human BAL1 transcript variant 1, which encodes the longest of the three human Ball isoforms (i.e., isoform a), is available to the public at the GenBank database under NM_031458.2 and NP_113646.2. The sequence of human BAL1 transcript variant 2 differs in the 5' untranslated region (UTR) compared to variant 1 while still encoding the same Ball isoform a and the sequences can be found under NM_001146102.1 and NP_001139574.1. The sequence of human BAL1 transcript variant 3 uses an alternative in-frame splice site in the 5' coding region relative to variant 1 resulting in a shorter protein (i.e., isoform b), and can be found under NM_001146103.1 and NP_001139575.1. The sequence of human BAL1 transcript variant 4 uses an alternative 5' UTR and alternative in-frame splice site in the 5' coding region relative to variant 1 resulting in isoform b, and can be found under NM_001146104.1 and NP_001139576.1. The sequence of human BAL1 transcript variant 5 uses an alternative 5' UTR and alternative in-frame splice site in the 5' coding region relative to variant 1 resulting in isoform b, and can be found under NM_001146105.1 and NP_001139577.1. The sequence of human BAL1 transcript variant 6 uses an alternative 5' UTR, 3' UTR, and 3' coding region relative to variant 1 resulting in a frameshift and can be found under NM_001146106.1 and NP_001139578.1. The frameshift results in a human Ball isoform c, which has a shorter and distinct C-terminus relative to isoform a. Nucleic acid and polypeptide sequences of BAL1 orthologs in organisms other than humans are well known and include, for example, mouse BAL1 (NM_030253.2 and NP_084529.1), chimpanzee BAL1 (XM_516693.2 and XP_516693.2), rat BAL1 (XM_221404.4 and XP_221404.4), cow BAL1 (NM_001076828.1 and NP_001070296.1), dog BAL1 (XM_545132.2 and XP_545132.2), and chicken BAL1 (XM_422116.2 and XP_422116.2). In some embodiments, BAL1 does not catalyze ADP ribosylation. As further indicated in the Examples, BAL1 orthologs have high sequence identity and retain common structural domains and functions well known in the art (see, Aguiar et al. (2000) Blood 96:4328-4334 and Takeyama et al. (2003) J. Biol. Chem. 278:21930-21937). Representative sequences of BAL1 orthologs are presented below in Table 1. In addition, numerous annotations of BAL1 sequences and structural features have previously been described in U.S. Pat. Nos. 6,870,040 and 7,858,742, each of which is incorporated herein in its entirety by this reference. It is to be noted that the term can further be used to refer to any combination of features described herein regarding BAL1 molecules. For example, any combination of sequence composition, percentage identify, sequence length, domain structure, functional activity, etc. can be used to describe a BAL1 molecule of the present invention.

The term "BBAP" can refer to a family of molecules having certain conserved structural and functional features. For example, the family of BBAP proteins comprise at least one "nuclear localization signal." As used herein, the term "nuclear localization signal" includes an amino acid sequence of about 4-20 amino acid residues in length, which serves to direct a protein to the nucleus. Typically, the nuclear localization sequence is rich in basic amino acids and exemplary sequences are well known in the art (Gorlich D. (1998) EMBO 5.17:2721-7). Amino acid residues 20-26, 462-478, and 475-478 of the human BBAP comprise nuclear localization signals. In addition BBAP proteins can be identified based on the presence of at least one "C3HC4-type zinc finger motif" in the protein or corresponding nucleic acid molecule. As used herein, the term "C3HC4-type zinc finger motif" includes an amino acid sequence of about 40-70 amino acid residues in length and having the general sequence C-X-(I,V)-C-X(11-30)-C-X-H-X-(F,I,L)-C-X(2)-C-(I,L,M)-X(10-18)-C-P-X-C, where X can be any amino acid (SEQ ID NO: 55). Proteins comprising such a ring-$H_2$-finger motif are believed to interact with DNA and to be involved in diverse functions, including site specific recombination, DNA repair, and transcriptional regulation. The ring-$H_2$-finger may also bind zinc/divalent metal ions to form a structure that is involved in specific protein-protein interactions (similar to the zinc-cysteine clusters of the adenovirus E1A). Amino acid residues 561-599 of the human BBAP comprise a C3HC4-type zinc finger motif.

In some embodiments, however, the term "BBAP" can refer to a specific BBAP family member originally named B-lymphoma and BAL-associated protein due to its E3 ligase activity and RING domain-containing C-terminus having near identity to that of Deltex (DTX) family members (Takeyama et al. (2003) J. Biol. Chem. 278:21930-21937). BBAP promotes self-ubiquitylation in a RING finger-dependent manner and can selectively monoubiquitylates histone H4 at lysine 91 (Takeyama et al. (2003) J. Biol. Chem. 278:21930-21937 and Yan et al. (2009) Mol. Cell. 36:110-120). BBAP also selectively modulated the kinetics of 53BP1 accumulation at DNA damage sites based on the disruption of BBAP-mediated histone H4K91 ubiquitylation and associated loss of chromatin-associated histone H4K20 methylase and methylated H4K20, since 53BP1 localizes to DNA damage sites by binding to methylated H4K20 (Yan et al. (2009) Mol. Cell. 36:110-120). The term is intended to include fragments, variants (e.g., allelic variants) and derivatives thereof. The sequence of a representative human BBAP cDNA is available to the public at the GenBank database under NM_138287.3 and NP_612144.1. Nucleic acid and polypeptide sequences of BBAP orthologs in organisms other than humans are well known and include, for example, mouse BBAP (NM_001013371.2 and NP_001013389.2), chimpanzee BBAP (XM_526285.2 and XP_526285.1), rat BBAP (XM_573295.2 and XP_573295.2), cow BBAP (XM_592997.4 and XP_592997.2), dog BBAP (XM_535762.2 and XP_535762.2), and chicken BBAP (XM_422114.2 and XP_422114.2). As further indicated in the Examples, BBAP orthologs have high sequence identity and retain common structural domains and functions well known in the art (see, Aguiar et al. (2000) Blood 96:4328-4334; Takeyama et al. (2003) J. Biol. Chem. 278:21930-21937; Monti et al. (2005) Blood 105:1851-1861; Juszczynski et al. (2006) Mol. Cell Biol. 26:5348-5359; and Aguiar et al. (2005) J. Biol. Chem. 280:33756-33765). Representative sequences of BBAP orthologs are presented below in Table 1. In addition, numerous annotations of BBAP sequences and structural features have previously been described in U.S. Pat. Nos. 7,112,420 and 7,632,660, each of which is incorporated herein in its entirety by this reference.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" is intended to include tissues, cells and biological fluids isolated from a subject, as well as tissues, cells and fluids present within a subject.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In some embodiments, media described herein can contain or comprise body fluids.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of lymphoma or its subtypes, including, but not limited to, lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, diffuse large B-cell lymphomas, MLL$^+$ pre B-cell ALL) based upon analysis of markers described herein.

The term "complex" refers to an association between at least two moieties (e.g. chemical or biochemical) that have an affinity for one another. "Protein complex" or "polypeptide complex" refers to a complex comprising at least one polypeptide. In one embodiment, a complex comprises a BAL1 polypeptide or fragment thereof along with a BBAP polypeptide or fragment thereof. In another embodiment, a complex comprises a BAL1 polypeptide and a BAL1-binding domain of a BBAP polypeptide. In still another embodiment, a complex comprises a BBAP polypeptide and a BBAP-binding domain of a BAL1 polypeptide. Embodiments of complexes described herein can encompass other molecules (e.g., polypeptides) that can bind to the complex, such as an antibody.

As used herein, the term "diagnostic marker" includes markers described herein which are useful in the diagnosis of cancer, e.g., over- or under-activity, emergence, expression, growth, remission, recurrence or resistance of tumors before, during or after therapy. The predictive functions of the marker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression (e.g., by ISH, Northern Blot, or qPCR), increased or decreased protein level (e.g., by IHC), or increased or decreased activity (determined by, for example, modulation of a pathway in which the marker is involved), e.g., in more than about 5%, 6%, 7%, 8%, 9%, 10%, 11%, 12%, 13%, 14%, 15%, 20%, 25%, or more of human cancers types or cancer samples; (2) its presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its presence or absence in clinical subset of subjects with cancer (e.g., those responding to a particular therapy or those developing resistance). Diagnostic markers also include "surrogate markers," e.g., markers which are indirect markers of cancer progression.

The term "DNA damage" refers to chemical and/or physical modification of the DNA in a cell, including, but not limited to, methylation, alkylation double-stranded breaks, cross-linking, thymidine dimers caused by ultraviolet light, and oxidative lesions formed by oxygen radical binding to DNA bases. DNA damage initiates a tightly regulated signaling cascade and the orderly recruitment of repair factors to damage sites as described further below. The chromatin substrate for DNA damage repair (DDR), DNA encircling nucleosomes comprised of core histone proteins, can be modulated in multiple ways—incorporation of histone variants, post-translational modification of select histones, repositioning of nucleosomes and generation of DNA repair foci (Polo and Jackson (2011) *Genes Dev.* 25:409-433). Cells utilize specific factors to detect and repair DNA single-strand breaks (SSB) and two complementary pathways, homologous recombination (HR) and non-homologous end-joining (NHEJ), to address double-strand breaks (DSB) (Polo and Jackson (2011) *Genes Dev.* 25:409-433). One of the earliest responses to single-strand and double-strand DNA breaks is the activation and recruitment of poly(ADP-ribose) polymerase protein (PARP) family members. Although the PARP family includes 16 proteins, thus far, only PARP1 and PARP2 have been linked to DNA damage responses (Ciccia and Elledge (2010) *Mol. Cell.* 40:179-204). Upon activation, PARP1 catalyzes the $NAD^+$-dependent addition of poly(ADP-ribose) (PAR) chains to target proteins including certain histones and PARP1 itself. PARP1 activation and associated PAR synthesis occur within seconds of DNA damage and persist for minutes (Polo and Jackson (2011) *Genes Dev.* 25:409-433). The rapid and short-lived PARylation at DNA damage sites is thought to promote a more relaxed chromatin structure which facilitates DNA repair (Krishnakumar and Kraus (2010) *Mol. Cell.* 39:8-24). DDR proteins assemble in a coordinated, sequential manner at sites of DNA breaks (Polo and Jackson (2011) *Genes Dev.* 25:409-433). The initial recruitment phase is rapid, transient and dependent upon PARylation at DNA damage sites (Polo and Jackson (2011) *Genes Dev.* 25:409-433). A second phase, which also begins within seconds but lasts for hours, includes the sequential phosphorylation and ubiquitylation of multiple DSB repair factors (Polo and Jackson (2011) *Genes Dev.* 25:409-433). Following the initial recruitment of the MRN (Mre11, RAD50 and Nbs1) complex, HR DSB repair involves ATM localization and phosphorylation of γH2AX and MDC1 (Polo and Jackson (2011) *Genes Dev.* 25:409-433). ATM-mediated phosphorylation of MDC1 promotes the recruitment of the RNF8 E3 ligase, which targets H2A histones (Polo and Jackson (2011) *Genes Dev.* 25:409-433). A second E3 ligase, RNF168, interacts with ubiquitylated H2A-type histones in a RNF8-dependent manner and amplifies the local concentration of ubiquitin conjugates (Doil et al. (2009) *Cell* 136:435-446 and Polo and Jackson (2011) *Genes Dev.* 25:409-433). Of note, RNF8/RNF168 also regulate the retention of the checkpoint mediators, 53BP1 and BRCA 1, at sites of DNA damage. The mechanisms of RNF8/RNF168-modulated recruitment of 53BP1 remain undefined, whereas BRCA 1 localizes to DNA breaks via RAP80, an adaptor protein with ubiquitin interacting motifs (UIM) (Doil et al. (2009) *Cell* 136:435-446). In some embodiments, "DNA damage repair" or "DDR" refers to one or more of the DNA damage repair processes described above. In other embodiments, "DNA repair" refers to a collection of mechanisms used to repair damage to DNA. A non-limiting list of exemplary DNA repair mechanisms includes non-homologous end joining (NHEJ), homologous recombination (HR), single-strand break repair, nucleotide excision repair (NER), base excision repair (BER), mismatch excision repair (MER), and other repair mechanisms using DNA polymerases, editing and processing nucleases and DNA repair helicases. Many genes and genetic elements in mammals (e.g., humans) are well known to those of skill in the art and are available in such compiled forms as Wood et al., Human DNA Repair Genes, Science, 291: 1284-1289 (February 2001) and Bulman et al., Locations of DNA Damage Response and Repair Genes in the Mouse and Correlation with Cancer Risk Modifiers, National Radiological Protection Board Report, October 2004 (ISBN 0-85951-544-3). In addition, a mouse DNA repair gene database is publicly available at the UK Health Protection Agency website. Exemplary proteins mediating NHEJ include, but are not limited to, Ligase4, XRCC4, H2AX, DNAPKcs (DNA-PK), Ku70, Ku80, Artemis, Cernunnos/XLF, MRE11, NBS1, and RAD50. Exemplary homologous recombination proteins include RAD51, RAD52, RAD54, XRCC3, RAD51C, BRCA1, BRCA2 (FANCD1), FANCA, FANCB, FANCC, FANCD2, FANCE, FANCF, FANCG, FANCJ (BRIP1/BACH1), FANCL, and FANCM. Exemplary proteins mediating BER include, but are not limited to, ung, smug1, mbd4, tdg, off1, myh, nth1, mpg, ape1, ape2, lig3, xrcc1, adprt, adprt12 and adprt13. Exemplary proteins mediating MER include, but are not limited to, msh2, msh3, msh4, msh5, msh6, pms1, pms3, mlh1, mlh3, pms213 and pms214. Exemplary DNA repair helicases include BLM and WRN.

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "marker" refers to any nucleic acid or protein sequence described herein useful for enhancing the efficacy of cancer therapies. In some embodiments, the markers of the present invention correspond to BAL1, BBAP, and/or BAL1-BBAP complexes described herein. Markers described herein include diagnostic, prognostic, and therapeutic markers.

The "normal" level of expression of a marker is the level of expression of the marker in cells of a subject, e.g., a human subject, not afflicted with a cancer, e.g., lung, ovarian, pancreatic, liver, breast, prostate, and colon carcinomas, as well as melanoma and multiple myeloma. An "overexpression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

An "overexpression" or "significantly higher level of expression or copy number" of a marker refers to an expression level or copy number in a test sample that is greater than the standard error of the assay employed to assess expression or copy number, and is preferably at least twice, and more preferably three, four, five or ten or more times the expression level or copy number of the marker in a control sample (e.g., sample from a healthy subject not afflicted with cancer) and preferably, the average expression level or copy number of the marker in several control samples.

The term "response to cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to BAL1, BBAP, and/or BAL1-BBAP complex measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom BAL1, BBAP, and/or BAL1-BBAP complex measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. BAL1, BBAP, and/or BAL1-BBAP complex measurement measurement threshold values that correlate to outcome of a cancer therapy can be determined using methods such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

An "RNA interfering agent" as used herein, is defined as any agent which interferes with or inhibits expression of a target gene, e.g., a marker of the invention, by RNA interference (RNAi). Such RNA interfering agents include, but are not limited to, nucleic acid molecules including RNA molecules which are homologous to the target gene, e.g., a marker of the invention, or a fragment thereof, short interfering RNA (siRNA), and small molecules which interfere with or inhibit expression of a target gene by RNA interference (RNAi). "RNA interference (RNAi)" is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent. "Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein). RNA interfering agents, e.g., siRNA molecules, may be administered to a subject having or at risk for having cancer, to inhibit expression of a marker gene of the invention, e.g., a marker gene which is overexpressed in cancer (such as the markers listed in Table 3) and thereby treat, prevent, or inhibit cancer in the subject.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anticancer agents or chemotherapy drugs can be greater than the sum of the separate effects of the anticancer agents or chemotherapy drugs alone.

As used herein, "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival"

(wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cancer) and preferably, the average expression level or copy number of the marker in several control samples.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
| --- | --- |
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

TABLE 1

```
SEQ ID NO: 1 Human BAL1 (isoform a) cDNA Sequence
     1 atggactttt ccatggtggc cggagcagca gcttacaatg aaaaatcagg taggattacc
    61 tcgctctcac tcttgtttca gaaagtcttt gctcagatct ttcctcagtg gagaaagggg
   121 aatacagaag aatgtctccc ctacaagtgc tcagagactg gtgctcttgg agaaaactat
   181 agttggcaaa ttcccattaa ccacaatgac ttcaaaattt taaaaaataa tgagcgtcag
   241 ctgtgtgaag tcctccagaa taagtttggc tgtatctcta ccctggtctc tccagttcag
   301 gaaggcaaca gcaaatctct gcaagtgttc agaaaaatgc tgactcctag gatagagtta
   361 tcagtctgga aagatgacct caccacacat gctgttgatg ctgtggtgaa tgcagccaat
   421 gaagatcttc tgcatggggg aggcctggcc ctggccctgg taaaagctgg tggatttgaa
   481 atccaagaag agagcaaaca gtttgttgcc agatatggta aagtgtcagc tggtgagata
   541 gctgtcacgg gagcagggag gcttccctgc aaacagatca tccatgctgt tgggcctcgg
   601 tggatggaat gggataaaca gggatgtact ggaaagctgc agagggccat tgtaagtatt
   661 ctgaattatg tcatctataa aaatactcac attaagacag tagcaattcc agccttgagc
   721 tctgggattt ttcagttccc tctgaatttg tgtacaaaga ctattgtaga gactatccgg
```

TABLE 1 -continued

```
 781 gttagtttgc aagggaagcc aatgatgagt aatttgaaag aaattcacct ggtgagcaat
 841 gaggaccta ctgttgctgc ctttaaagct gcttcagaat tcatcctagg gaagagtgag
 901 ctgggacaag aaaccacccc ttctttcaat gcaatggtcg tgaacaacct gaccctccag
 961 attgtccagg gccacattga atggcagacg gcagatgtaa ttgttaattc tgtaaaccca
1021 catgatatta cagttggacc tgtggcaaag tcaattctac aacaagcagg agttgaaatg
1081 aaatcggaat tcttgccac aaaggctaaa cagtttcaac ggtcccagtt ggtactggtc
1141 acaaaaggat ttaacttgtt ctgtaaatat atataccatg tactgtgca ttcagaattt
1201 cctaaacctc agatattaaa acatgcaatg aaggagtgtt tggaaaaatg cattgagcaa
1261 aatataactt ccatttcctt tcctgcctt gggactggaa acatgaaat aaagaaggaa
1321 acagcagcag agatttgtt tgatgaagtt ttaacatttg ccaaagacca tgtaaaacac
1381 cagttaactg taaaatttgt gatctttcca acagatttgg agatatataa ggctttcagt
1441 tctgaaatgg caaagaggtc caagatgctg agtttgaaca attacagtgt cccccagtca
1501 accagagagg agaaaagaga aaatgggctt gaagctagat ctcctgccat caatctgatg
1561 ggattcaacg tggaagagat gtatgaggcc cacgcatgga tccaaagaat cctgagtctc
1621 cagaaccacc acatcattga gaataatcat attctgtacc ttgggagaaa ggaacatgac
1681 attttgtctc agcttcagaa aacttcaagt gtctccatca cagaaattat cagcccagga
1741 aggacagagt tagagattga aggagcccgg gctgacctca ttgaggtggt tatgaacatt
1801 gaagatatgc tttgtaaagt acaggaggaa atgcaaggga aaaaggagcg aggcctttgg
1861 cgctcgttag acagtggac tattcagcaa caaaaaccc aagacgaaat gaagaaaat
1921 atcatatttc tgaaatgtcc tgtgcctcca actcaagagc ttctagatca aaagaaacag
1981 tttgaaaaat gtggtttgca ggttctaaag gtgagagaaga tagacaatga ggtccttatg
2041 gctgccttc aaagaaagaa gaaaatgatg gaagaaaaac tgcacaggca acctgtgagc
2101 cataggctgt tcagcaagt cccataccag ttctgcaatg tggtatgcag agttggcttt
2161 caaagaatgt actcgacacc ttgcgatcca aaatacggag ctggcatata cttcaccaag
2221 aacctcaaaa acctggcaga gaaggccaag aaaatctctg ctgcagataa gctgatctat
2281 gtgtttgagg ctgaagtact cacaggcttc ttctgccagg gacatccgtt aaatattgtt
2341 cccccaccac tgagtcctgg agctatagat ggtcatgaca gtgtggttga caatgtctcc
2401 agccctgaaa cctttgttat ttttagtggc atgcaggcta tacctcagta tttgtggaca
2461 tgcacccagg aatatgtaca gtcacaagat tactcatcag gaccaatgag acccttgca
2521 cagcatcctt ggaggggatt cgcaagtggc agccctgttg attaa
```

SEQ ID NO: 2 Human BAL1 (isoform a) Amino Acid Sequence
```
  1 mdfsmvagaa ayneksgrit slsllfqkvf aqifpqwrkg nteeclpykc setgalgeny
 61 swqipinhnd fkilknnerq lcevlqnkfg cistlvspvq egnskslqvf rkmltpriel
121 svvkddltth avdavvnaan edllhgggla lalvkaggfe iqeeskqfva rygkvsagei
181 avtgagrlpc kqiihavgpr wmewdkqgct gklqraivsi lnyviyknth iktvaipals
241 sgifqfplnl ctktivetir vslqgkpmms nlkeihlvsn edptvaafka asefilgkse
301 lgqettpsfn amvvnnltlq ivqghiewqt advivnsvnp hditvgpvak silqqagvem
361 kseflatkak qfqrsqlvlv tkgfnflcky iyhvlwhsef pkpqilkham keclekcieq
421 nitsisfpal gtgnmeikke taaeilfdev ltfakdhvkh qltvkfvifp tdleiykafs
481 semakrskml slnnysvpqs treekrengl earspainlm gfnveemyea hawigrilsl
541 qnhhiiennh ilylgrkehd ilsqlqktss vsiteiispg rteleiegar adlievvmni
601 edmlckvqee markkerglw rslgqwtiqq qktqdemken iiflkcpvpp tqelldqkkg
661 fekcglqvlk vekidnevlm aafqrkkkmm eeklhrqpvs hrlfqqvpyq fcnvvcrvgf
721 qrmystpcdp kygagiyftk nlknlaekak kisaadkliy vfeaevltgf fcqghplniv
781 ppplspgaid ghdsvvdnvs spetfvifsg mqaipqylwt ctqeyvqsqd yssgpmrpfa
841 qhpwrgfasg spvd
```

SEQ ID NO: 3 Human BAL1 (isoform b) cDNA Sequence
```
  1 atggactttt ccatggtggc cggagcagca gcttacaatg aaaaatcaga gactggtgct
 61 cttggagaaa actatagttg gcaaattccc attaaccaca atgacttcaa aatttttaaaa
121 aataatgagc gtcagctgtg tgaagtcctc cagaataagt ttggctgtat ctctaccctg
181 gtctctccag ttcaggaagg caacagcaaa tctctgcaag tgttcagaaa aatgctgact
241 cctaggatag agttatcagt ctggaaagat gacctcacca cacatgctgt tgatgctgtg
301 gtgaatgcag ccaatgaaga tcttctgcat gggggaggcc tggccctggc cctggtaaaa
361 gctggtggat tgaaaatcca agaagagagc aaacagtttg ttgccagata tggtaaagtg
421 tcagctggtg agatagctgt cacgggagca gggaggcttc cctgcaaaca gatcatccat
481 gctgttggc ctcggtggat ggaatgggat aaacaggat gtactggaaa gctgcagagg
541 gccattgtaa gtattctgaa ttatgtcatc tataaaaata ctcacattaa gacagtagca
601 attccagcct tgagctctgg gatttttcag ttccctctga atttgtgtac aaagactatt
661 gtagagacta tccgggttag tttgcaaggg aagccaatga tgagtaattt gaaagaaatt
721 cacctggtga gcaatgagga ccctactgtt gctgccttta agctgcttc agaattcatc
781 ctagggaaga gtgagctggg acaagaaacc accccttctt tcaatgcaat ggtcgtgaac
841 aacctgaccc tccagattgt ccagggccac attgaatggc agacggcaga tgtaattgtt
901 aattctgtaa acccacatga tattacagtt ggacctgtgg caaagtcaat tctacaacaa
961 gcaggagttg aaatgaaatc ggaatttctt gccacaaagg ctaaacagtt tcaacggtcc
1021 cagttggtac tggtcacaaa aggatttaac ttgttctgta aatatatata ccatgtactg
1081 tggcattcag aatttcctaa acctcagata ttaaaacatg caatgaagga gtgtttggaa
1141 aaatgcattg agcaaaatat aacttccatt tcctttcctg cccttgggac tggaaacatg
1201 gaaataaaga aggaaacagc agcagagatt tgtttgatg aagtttttaac atttgccaaa
1261 gaccatgtaa aacaccagtt aactgtaaaa tttgtgatct ttccaacaga tttgagata
1321 tataaggctt tcagttctga aatggcaaag aggtccaaga tgctgagttt gaacaattac
1381 agtgtccccc agtcaaccag agaggagaaa agagaaatgg gcttgaagc tagatctcct
1441 gccatcaatc tgatgggatt caacgtgaa gagatgtatg aggcccacgc atggatccaa
1501 agaatcctga gtctccagaa ccaccacatc attgaataa atcatattct gtaccttggg
1561 agaaaggaac atgacatttt tgtctcagctt cagaaaactt caagtgtctc catcacagaa
1621 attatcagcc caggaaggac agagttagag attgaaggag cccgggctga cctcattgag
1681 gtggttatga acattgaaga tatgctttgt aaagtacagg aggaaatggc aaggaaaaag
1741 gagcgaggcc tttggcgctc gttaggacag tggactattc agcaacaaaa acccaagac
1801 gaaatgaaag aaaaatcat atttctgaaa tgtcctgtgc ctccaactca agagcttcta
```

TABLE 1 -continued

```
1861 gatcaaaaga aacagtttga aaaatgtggt ttgcaggttc taaaggtgga gaagatagac
1921 aatgaggtcc ttatggctgc ctttcaaaga aagaagaaaa tgatggaaga aaaactgcac
1981 aggcaacctg tgagccatag gctgtttcag caagtcccat accagttctg caatgtggta
2041 tgcagagttg gctttcaaag aatgtactcg cacccttgcg atccaaaata cggagctggc
2101 atatacttca ccaagaacct caaaaacctg gcagagaagg ccaagaaaat ctctgctgca
2161 gataagctga tctatgtgtt tgaggctgaa gtactcacga gcttcttctg ccagggacat
2221 ccgttaaata ttgttccccc accactgagt cctggagcta tagatggtca tgacagtgtg
2281 gttgacaatg tctccagccc tgaaaccttt gttatttta gtggcatgca ggctatacct
2341 cagtatttgt ggacatgcac ccaggaatat gtacagtcag aagattactc atcaggacca
2401 atgagaccct ttgcacagca tccttggagg ggattcgcaa gtggcagccc tgttgattaa
```

SEQ ID NO: 4 Human BAL1 (isoform b) Amino Acid Sequence
```
  1 mdfsmvagaa aynekseetga lgenyswqip inhndfkilk nnerqlcevl qnkfgcistl
 61 vspvqegnsk slqvfrkmlt prielsvwkd dltthavdav vnaanedllh ggglalalvk
121 aggfeiqees kqfvarygkv sageiavtga grlpckqiih avgprwmewd kqgctgklqr
181 aivsilnyvi yknthiktva ipalssgifq fplnlctkti vetirvslqg kpmmsnlkei
241 hlvsnedptv aafkaasefi lgkselgqet tpsfnamvvn nltlqivqgh iewqtadviv
301 nsvnphditv gpvaksilqq agvemksefl atkakqfqrs qlvlvtkgfn lfckyiyhvl
361 whsefpkpqi lkhamkecle kcieqnitsi sfpalgtgnm eikketaaei lfdevltfak
421 dhvkhqltvk fvifptdlei ykafssemak rskmlslnny svpqstreek renglearsp
481 ainlmgfnve emyeahawiq rilslqnhhi iennhilylg rkehdilsql qktssysite
541 iispgrtele iegaradlie vvmniedmlc kvqeemarkk erglwrslgq wtiqqqktqd
601 emkeniiflk cpvpptqell dqkkqfekcg lqvlkvekid nevlmaafqr kkkmmeeklh
661 rqpvshrlfq qvpyqfcnvv crvgfqrmys tpcdpkygag iyftknlknl aekakkisaa
721 dkliyvfeae vltgffcqgh plnivppppls pgaidghdsv vdnvsspetf vifsgmqaip
781 qylwtctqey vqsqdyssgp mrpfaqhpwr gfasgspvd
```

SEQ ID NO: 5 Human BAL1 (isoform c) cDNA Sequence
```
   1 atggactttt ccatggtggc cggagcagca gcttacaatg aaaaatcaga gactggtgct
  61 cttggagaaa actatagttg gcaaattccc attaaccaca atgacttcaa aattttaaaa
 121 aataatgagc gtcagctgtg tgaagtcctc cagaataagt ttggctgtat ctctaccctg
 181 gtctctccag ttcaggaagg caacagcaaa tctctgcaag tgttcagaaa aatgctgact
 241 cctaggatag agttatcagt ctggaaagat gacctcacca cacatgctgt tgatgctgtg
 301 gtgaatgcag ccaatgaaga tcttctgcat gggggaggcc tggccctggc cctggtaaaa
 361 gctggtggat ttgaaatcca agaagagagc aaacagtttg ttgccagata tggtaaagtg
 421 tcagctggtg agatagctgt cacgggagca gggaggcttc cctgcaaaca gatcatccat
 481 gctgttgggc ctcggtggat ggaatgggat aaacagggat gtactggaaa gctgcagagg
 541 gccattgtaa gtattctgaa ttatgtcatc tataaaaata ctcacattaa gacagtagca
 601 attccagcct tgagctctgg gattttttcag ttccctctga atttgtgtac aaagactatt
 661 gtagagacta tccgggttag tttgcaaggg aagccaatga tgagtaattt gaaagaaatt
 721 cacctggtga gcaatgagga ccctactgtt gctgccttta agctgcttc agaattcatc
 781 ctagggaaga gtgagctggg acaagaaacc accccttctt tcaatgcaat ggtcgtgaac
 841 aacctgaccc tccagattgt ccagggccaa attgaatggc agacggcaga tgtaattgtt
 901 aattctgtaa acccacatga tattacagtt ggacctgtgg caaagtcaat tctacaacaa
 961 gcaggagttg aaatgaaatc ggaatttctt gccacaaagg ctaaacagtt tcaacggtcc
1021 cagttggtac tggtcacaaa aggatttaac ttgttctgta aatatatata ccatgtactg
1081 tggcattcag aatttcctaa acctcagata ttaaaacatg caatgaagga gtgtttggaa
1141 aaatgcattg agcaaaatat aacttccatt tcctttcctg cccttgggac tggaaacatg
1201 gaaataaaga aggaaacagc agcagagatt ttgtttgatg aagttttaac atttgccaaa
1261 gaccatgtaa aacaccagtt aactgtaaaa tttgtgatct ttccaacaga tttggagata
1321 tataaggctt tcagttctga aatggcaaag aggtccaaga tgctgagttt gaacaattac
1381 agtgtcccc agtcaaccag agaggagaaa agagaaatgg gcttgaagc tagatctcct
1441 gccatcaatc tgatgggatt caacgtgaa gagatgtatg aggcccacgc atggatccaa
1501 agaatcctga gtctccagaa ccaccacatc attgagaata atcatattct gtaccttggg
1561 agaaaggaac atgacatttt gtctcagctt cagaaaactt caagtgtctc catcacagaa
1621 attatcagcc aggaaggac agagttagag attgaaggag cccgggctga cctcattgag
1681 gtggttatga cattgaaga tatgctttgt aaagtacagg aggaaatggc aaggaaaaag
1741 gagcgaggcc tttggcgctc gttaggacag tggactattc agcaacaaaa aacccaagac
1801 gaaatgaaag aaaatatcat attctgtaaa tgtcctgtgc ctccaactca agagctctca
1861 gatcaaaaga aacagtttga aaaatgtggt ttgcaggttc taaaggtgga gaagatagac
1921 aatgaggtcc ttatggctgc ctttcaaaga aagaagaaaa tgatggaaga aaaactgcac
1981 aggcaacctg tgagccatag gctgtttcag caagtcccat accagttctg caatgtggta
2041 tgcagagttg gctttcaaag aatgtactcg cacccttgcg taggtgtca atgcctcatc
2101 attggggcta ctctgtggaa tttggtgagc tga
```

SEQ ID NO: 6 Human BAL1 (isoform c) Amino Acid Sequence
```
  1 mdfsmvagaa aynekseetga lgenyswqip inhndfkilk nnerqlcevl qnkfgcistl
 61 vspvqegnsk slqvfrkmlt prielsvwkd dltthavdav vnaanedllh ggglalalvk
121 aggfeiqees kqfvarygkv sageiavtga grlpckqiih avgprwmewd kqgctgklqr
181 aivsilnyvi yknthiktva ipalssgifq fplnlctkti vetirvslqg kpmmsnlkei
241 hlvsnedptv aafkaasefi lgkselgqet tpsfnamvvn nltlqivqgh iewqtadviv
301 nsvnphditv gpvaksilqq agvemksefl atkakqfqrs qlvlvtkgfn lfckyiyhvl
361 whsefpkpqi lkhamkecle kcieqnitsi sfpalgtgnm eikketaaei lfdevltfak
421 dhvkhqltvk fvifptdlei ykafssemak rskmlslnny svpqstreek renglearsp
481 ainlmgfnve emyeahawiq rilslqnhhi iennhilylg rkehdilsql qktssysite
541 iispgrtele iegaradlie vvmniedmlc kvqeemarkk erglwrslgq wtiqqqktqd
601 emkeniiflk cpvpptqell dqkkgfekcg lqvlkvekid nevlmaafqr kkkmmeeklh
661 rqpvshrlfq qvpyqfcnvv crvgfqrmys tpcgrcgcli igatlwnlvs
```

TABLE 1 -continued

SEQ ID NO: 7 Mouse BAL1 cDNA Sequence
```
   1 atggctatt acatggatac atgggcggca gctcccgccg aaagaccagc caacaattct
  61 cttgaagaac attatagatg gcaaattccc attaaacaca atgtcttcga aattttaaag
 121 agcaatgaga gtcagctatg tgaagtcctc caaaataagt ttggatgcat ctctaccctg
 181 agctgtccaa ctctagcagg gagcagctct cctgctcaga gagtcttcag aaggaccctg
 241 atccctggga tagagttatc tgtctggaag gatgacccta ccagacacgt tgttgatgct
 301 gtggtgaacg cagccaatga aaaccttttg catggaagtg gcctggccgg aagcttggtg
 361 aaaactggtg gctttgaaat ccaagaagag agcaaaagaa tcattgccaa cgttggtaaa
 421 atctcagttg gtgaatcgc tatcaccggt gcggggacga ttccttgcca tttgattatc
 481 catgcggttg gacctcggtg gacagttacg aacagccaga cagctatcga attactgaaa
 541 tttgccatta ggaacattct agattatgtc accaaatatg atctacgcat taagacagta
 601 gcaattccag ccctgagctc tggaattttc agttccctc tggatttgtg tacaagcata
 661 attttagaaa ctatccggtc ttatttccaa gacaagcaaa tgttcggtaa tttgagagag
 721 attcatctgg tgagcaatga ggaccccact gttgcgtcct taaatccgc ctcagaaagc
 781 atcctaggga gggacctgag ctcttggggg gtccagaaa ctgaccctgc ttccaccatg
 841 actcttcgca tcggccgggg cctgactctc cagattgtcc aaggctgtat tgaaatgcaa
 901 acaacagatg taattgttaa ttctggatac atgcaggatt ttaaatcagg acgagtggca
 961 cagtcgattc ttagacaagc aggggttgaa atggaaaagg aacttgacaa ggttaacctg
1021 tccacagatt atcaagaggt gtgggtcaca aaaggattta aattgtcctg tcagtatgtc
1081 ttccatgtgg catggcattc ccaaatcaac aaataccaga tattgaaaga tgcaatgaag
1141 tcctgtctag aaaaatgcct taaaccagat ataaattcca tttccttttcc tgctctcggg
1201 acaggattga tggatttgaa gaagagtaca gcagctcaga taatgtttga ggaagttttt
1261 gcatttgcta aagagcacaa ggaaaaaacg ctaactgtaa agattgtgat cttttccagta
1321 gatgtgagaa cgtacaagat tttttatgct gaaatgacaa aaaggtccaa cgagctgaat
1381 ctcagcggta atagtggtgc tttagccctg cagtggtccg gtggggagca aagaagaggc
1441 ggccttgaag ctggatctcc tgccatcaat ctcatgggtg taaaagtggg agagatgtgt
1501 gaggcccagg aatggattga aaggttgctg gtctccctgg accaccacat cattgagaat
1561 aatcatattc tctatcttgg gaaaaaagag cacgacgtgc tgtctgagct ccagaccagc
1621 acaagagtct ccatttcaga gactgtcagt ccaagaacgg ccactttgga gattaaaggt
1681 ccccaggctg acctcattga cgcagttatg aggattgaat tgtatgctgtg tgacgttcag
1741 gaagaagtgg caggaaaaag ggagaaaaat ctttggagct tgtcaggaca ggggaccaac
1801 cagcaagaaa aactggataa aatggaagaa tcgtacacat tcaacgata cccagcatca
1861 ttaactcagg aacttcagga ccgaaagaaa cagtttgaaa agtgtggctt gtgggttgtg
1921 caggtggagc agatagacaa taaggtgctg ctggctgcct tccaagagaa gaagaaaatg
1981 atggaagaga ggacgccaaa gggatctggg agccaaaggt tgtttcagca ggtcccacat
2041 cagttctgca atacggtgtg cagagtcggc ttccacagaa tgtattcgac atcctataac
2101 ccagtttatg gagccggcat atatttcacc aagagcctca aaaatctagc agacaaggtc
2161 aagaaaacct caagcacaga caagctaatc tatgtgtttg aggcagaagt actcacaggg
2221 tccttctgtc agggtaattc ctcaaatatc atccctccac cattgagtcc tggggcctta
2281 gatgtcaatg acagcgtagt tgacaatgtt tccagccctg aaaccattgt tgttttttaat
2341 ggcatgcagg ccatgcccct gtacttgtgg acttgcacac aggataggac attctcacag
2401 catccgatgt ggtcacaggg ctactcatca ggaccaggaa tggtctcttc gctgcagtcc
2461 tgggaatggg tcttaaatgg cagctctgtt tag
```

SEQ ID NO: 8 Mouse BAL1 Amino Acid Sequence
```
   1 mayymdtwaa apaerpanns leehyrwqip ikhnvfeilk snesqlcevl qnkfgcistl
  61 scptlagsss paqrvfrrtl ipgielsvwk ddltrhvvda vvnaanenll hgsglagslv
 121 ktggfeiqee skriianvgk isvggiaitg agrlpchlii havgprwtvt nsqtaiellk
 181 fairnildyv tkydlriktv aipalsssgif qfpldlctsi iletirlyfq dkqmfgnlre
 241 ihlvsnedpt vasfksases ilgrdlsswg gpetdpastm tlrigrgltl qivqgciemq
 301 ttdvivnsgy mqdfksgrva qsilrqagve mekeldkvnl stdyqevwvt kgfklscqyv
 361 fhvawhsqin kyqilkdamk sclekclkpd insisfpalg tglmdlkkst aaqimfeevf
 421 afakehkekt ltvkivifpv dvetykifya emtkrsneln lsgnsgalal qwssgeqrrg
 481 gleagspain lmgvkvgemc eagewierll vsldhhiien nhilylgkke hdvlselqts
 541 trvsisetvs prtatleikg pqadlidavm riecmlcdvq eevagkrekn lwslsgqgtn
 601 qqekldkmee sytfqrypas ltqelqdrkk qfekcglwvv qvegidnkvl laafqekkkm
 661 meertpkgsg sqrlfqqvph qfcntvcrvg fhrmystsyn pvygagiyft kslknladkv
 721 kktsstdkli yvfeaevltg sfcqgnssni ippplspgal dvndsvvdnv sspetivvfn
 781 gmqamplylw tctqdrtfsq hpmwsqgyss gpgmvsslqs wewvlngssv
```

SEQ ID NO: 9 Human BBAP cDNA Sequence
```
   1 atggcctccc acctgcgccc gccgtccccg ctcctcgtgc gggtgtacaa gtccggcccc
  61 cgagtacgaa ggaagctgga gagctacttc cagagctcta agtcctcggg cggcggggag
 121 tgcacggtca gcacccagga acacgaagcc ccgggcacct tccgggtgga gttcagtgaa
 181 agggcagcta aggagagagt gttgaaaaaa ggagagcacc aaatacttgt tgacgaaaaa
 241 cctgtgccca ttttcctggt acccactgaa aattcaataa agaagaacac gagacctcaa
 301 atttcttcac tgcacacaat caagcagaaa acaccgtcgt gtgatatgca tcaacatgaa
 361 ggacatattc ctaatgctgt ggattcctgt ctccaaaaga tcttttcttac tgtaacagct
 421 gacctgaact gtaaacctgtt ctccaaagag cagagggcat acataaccac actgtgccct
 481 agtatccagaa aaatgaagg tcacgatgga attgagaagg tgtgtggtga cttccaagac
 541 attgaaagaa tacatcaatt tttgatgag gagttcctgg aaagtgagca gaaacaacaa
 601 tttttccctt caatgacaga gaggaagcca ctcagtcagc aggagaggga cagctgcatt
 661 tctccttctg aaccagaaac caaggcagaa caaaaaagca actattttga agttccttg
 721 ccttacttg aatacttaa atatatcgt cctgataaaa tcaactcaat agagaaaaga
 781 tttggtgtaa acattgaat ccaggagagt tctccaataa tggtctgttt agatttcacc
 841 tcagtcgat caggtgacct gcaagcagct cgtgagtgtt ttgctagtga atttcagaag
 901 aacacagaac ctctgaagca agaatgtgtc tctttagcag acagtaagca ggcaaataaa
 961 ttcaaacagg aattgaatca ccagtttaca agctcctta taaggagaa aggaggcgaa
1021 ttaactctcc ttgggaccca agatgacatt tcagctgcca acaaaaaat ctctgaagct
1081 tttgtcaaga tacctgtgaa actatttgct gccaattaca tgatgaatgt aattgaggtt
```

TABLE 1 -continued

```
1141 gatagtgccc actataaact tttagaaact gaattactac aggagatatc agagatcgaa
1201 aaaaggtatg acatttgcag caaggtttct gagaaaggtc agaaaacctg cattctgttt
1261 gaatccaagg acaggcaggt agatctatct gtgcatgctt atgcaagttt catcgatgcc
1321 tttcaacatg cctcatgtca gttgatgaga gaagttcttt tactgaagtc tttgggcaag
1381 gagagaaagc acttacatca gaccaagttt gctgatgact ttagaaaaag acatccaaat
1441 gtacactttg tgctaaatca agagtcaatg actttgactg gtttgccaaa tcaccttgca
1501 aaggcgaagc agtatgttct aaaaggagga ggaatgtctt cattggctgg aaagaaattg
1561 aaagagggtc atgaaacacc gatggacatt gatagcgatg attccaaagc agcttctccg
1621 ccactcaagg gctctgtgag ttctgaggcc tcagaactgg acaagaagga aaagggcatc
1681 tgtgtcatct gtatgacac cattagtaac aaaaaagtgc taccaaagtg caagcatgaa
1741 ttctgcgccc cttgtatcaa caaagccatg tcatataagc caatctgtcc cacatgccag
1801 acttcctatg gtattcagaa aggaaatcag ccagagggaa gcatggtttt cactgtttca
1861 agagactcac ttccaggtta tgagtccttt ggcaccattg tgattactta ttctatgaaa
1921 gcaggcatac aaacagaaga cacccaaac ccaggaaaga gatacccctgg aatacagcga
1981 actgcatact tgcctgataa taggaagga aggaagtttt tgaaactgct ttatagggcc
2041 tttgaccaaa agctgatttt tacagtgggg tactctcgcg tattaggagt ctcagatgtc
2101 atcacttgga atgatattca ccacaaaaca tcccggtttg gaggaccaga aatgtatggc
2161 tatcctgatc cttcttacct gaaacgtgtc aaagaggagc tgaaagccaa aggaattgag
2221 taa
```

SEQ ID NO: 10 Human BBAP Amino Acid Sequence
```
  1 mashlrppsp llvrvyksgp rvrrklesyf qssksggge ctvstgehea pgtfrvefse
 61 raakervlkk gehqilvdek pvpiflvpte nsikkntrpq issltqsqae tpsgdmhqhe
121 ghipnavdsc lqkifltvta dlncnlfske qrayittlcp sirkmeghdg iekvcgdfqd
181 ierihqflse qfleseqkqq fspsmterkp lsqqerdsci spsepetkae qksnyfevpl
241 pyfeyfkyic pdkinsiekr fgvnieiqes spnmvcldft ssrsgdleaa resfasefqk
301 nteplkqecv sladskqank fkqelnhqft kllikekgge ltllgtqddi saakqkisea
361 fvkipvklfa anymmnviev dsahykllet ellqeiseie krydicskvs ekgqktcilf
421 eskdrqvdls vhayasfida fqhascqlmr evlllkslgk erkhlhqtkf addfrkrhpn
481 vhfvlnqesm tltglpnhla kakqyvlkgg gmsslagkkl keghetpmdi dsddskaasp
541 plkgsyssea seldkkekgi cvicmdtisn kkvlpckche fcapcinkam sykpicptcq
601 tsygiqkgnq pegsmvftvs rdslpgyesf gtivitysmk agiqteeehpn pgkrypgiqr
661 taylpdnkeg rkvlkllyra fdqkliftvg ysrvlgvsdv itwndihhkt srfggpemyg
721 ypdpsylkry keelkakgie
```

SEQ ID NO: 11 Mouse BBAP cDNA Sequence
```
   1 atggcttcca gtcccgaccc gccgtccccg ctactcgtac ggctgcggga gtccatcccc
  61 aaggcgcaca ggaagctcga gatatacttc cagagccggg cctcgggagg tgggagtgc
 121 tctgtccagc ccgtgggccc cagcgcccg gacacctacg aggtgaagtt cctaaaaaaa
 181 gcagataagg agaaagtgtt gaaaagagc gaacacgaga tgttggtcca taacaaacct
 241 gtgaccattg tcctggaaac tactaaaaag ccagtagagg acctgagacc cagactccca
 301 tccttgacac agccagtgga gacaccaagc tccagaccc cgtccttgac ggggtctctg
 361 gatgaagcac tttgtgatga catacatccc caggacgggg tcgtttctaa ctctgttgac
 421 tcagttgtcc aaaagatctt tcttgctgtg accgctgagc tgaactgtga cctgctctct
 481 aaagagcaga gagcatctat aaccactgtc tgccctcaca tcatcaaaag catggagggt
 541 agtgatggaa ttaagaaggt gtgtggcaac ttcaaagata ttgaaaagat acatcacttc
 601 ttgagtgagc agcttttgga acgggagcag aaacggaagg gaagcgagca gaaacggaag
 661 tgcgccccac agaaacacac acctcccgat gtggagcggg agcccctga tcagagcagt
 721 attcaagttc ctgtgcttct ccttgaatat ttcaagcatg ttaatccggg tagactagag
 781 ttcatagagt acaaatttgg tgtaaacatt gaaatccaag ctagttctcc caatatggtc
 841 actgtaggct tcacctccag cccatttggc aacgtagaag aagcaagtca gtccttttgtc
 901 agagactttc agaaatgctc gcagtctctg aagcaagatt gtatctcttt agaggagcac
 961 cagagagcaa aggaggtcag acaggagctg agtcgctgct tcccaaagct cttgataaag
1021 ggacagggaa gaacgctgac tcctcctcggc tctcctgctg acatttcagc cgccacagaa
1081 aaagtctccc aaggtcttgg cctgagacct gtgaaaataa ccgcatctgg gtacacgacg
1141 ggcatcgagg tcgattcaac acgctttaag cttctagagc ctgaactgct ccaggaaatc
1201 tcagagatcag agcagaagtt taacacccgt ggcaaagtcc aggaaaaagg ccaggaaaacc
1261 tgcattcttt ttgtccccaa ggataaagac ttagacctgt cagtgcagtc ctacacaggt
1321 tttactgatg ccttccagcg tgccacgtgg cagctgagga caagttct gtcgctgaaa
1381 ggggttgggca aggagagagc tcgcttacac aataccaagt tgccgacaa ctttaaaaaaa
1441 gagcacccga atgtgcactt tgtgacatct caggagtcag tgaccttgac tggcttgcca
1501 catcaccttg cgcaggcaat gcagtatgtc tccaaaagaa tgggactggc accgtcatct
1561 ggagagaaac tcgctatgga tcaggaaacc cccatggaga tcagcagtag tgaccccat
1621 ggagatcagc aggagaatgc agccttacct gctcccgag gcacctctag cagcctgca
1681 gcttcgaagg ggactgagga ctactgtgtc atctgcatgg ataccatcag caacaagcac
1741 gtgctcccca agtgcaagca tgaattctgc acctcgtgta tcagcaaagc catgcttatc
1801 aagcctgtct gtcctgtgtg tctgacttcc tacggcatcc agaaagggaa ccagccagag
1861 ggaaccatgt cttactccac tcaaaaaggg tcacttccag gttatgaagg ctgtggcacc
1921 attgtgatta ttatgaaat aaaagatggc atccaaacaa aagagcaccc aaacccagga
1981 aaggcttatc atgaacacg gcgaactgca tacttgcctg ataatactga gggaagaaag
2041 gttttggatc tgctccacga agcctttaag cacagactgc ttttcacaat aggatactct
2101 cgagcaacag gagtctcgga tgtcattaca tggaatgata ttcatcacaa aacatccagag
2161 tttggaggac cagcaaattt tggctaccct gatcctgatt acctgaaacg tgtcaaggag
2221 gagctgaaag caaaaggcat tgagtaa
```

SEQ ID NO: 12 Mouse BBAP Amino Acid Sequence
```
  1 masspdppsp llvrlresip kahrkleiyf qsrasgggec svqpvgpsap dtyevkflkk
 61 adkevlkks ehemlvhnkp vtivlettkk pvedlrprlp sltqpvetps srppsltgsl
121 dealcddihp qdglvsnsvd svvqkiflav taelncdlls keqrasittv cphiiksmeg
181 sdgikkvcgn fkdiekihhf lseqllereq krkgseqkrk capqkhtppd vereppdqss
```

TABLE 1 -continued

```
241 iqvpvllley fkhvnpgrle fieykfgvni eiqasspnmv tvgftsspfg nveeasqsfv
301 rdfqkcsqsl kqdcisleeh qrakevrqel srcfpkllik gqgrtltllg spadisaate
361 kvsqglglrp vkitasgytt gievdstrfk llepellqei seieqkfntr gkvqekgqkt
421 cilfvpkdkd ldlsvqsytg ftdafqratw qlrtevlslk glgkerarlh ntkfadnfkk
481 ehpnvhfvts qesvtltglp hhlaqamqyv skrmglapss geklamdqet pmeisssdph
541 gdqqenaalp aprgtssspa askgtedycv icmdtisnkh vlpkckhefc tsciskamli
601 kpvcpvclts ygiqkgnqpe gtmsystqkg slpgyegcgt ivinyeikdg iqtkehpnpg
661 kayhgtrrta ylpdntegrk vldllheafk hrltftigys ratgvsdvit wndihhktsk
721 fggpanfgyp dpdylkrvke elkakgie
```

Before the present invention is further described, it will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein are well known in the art and can be used in the embodiments of the invention.

It is further to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a BAL1-BBAP complex" includes a plurality of such complexes and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

I. Isolated Nucleic Acids

One aspect of the invention pertains to methods utilizing isolated nucleic acid molecules that encode BAL1 and/or BBAP or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BAL1 and/or BBAP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., alymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO: 1, 3, 5, 7, 9, and 11 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, 9, and 11 or a portion thereof (i.e., 100, 200, 300, 400, 450, 500, or more nucleotides), can be isolated using standard molecular biology techniques and the sequence information provided herein. For example, a human BAL1 and/or BBAP cDNA can be isolated from a human muscle cell line (from Stratagene, LaJolla, Calif., or Clontech, Palo Alto, Calif.) using all or portion of SEQ ID NOs: 1, 3, 5, 7, 9, or 11, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989). Moreover, a nucleic acid molecule encompassing all or a portion of SEQ ID NOs: 1, 3, 5, 7, 9 or 11 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, 9, or 11, or fragment thereof, can be isolated by the polymerase chain reaction using oligonucleotide primers designed based upon the sequence of SEQ ID NOs: 1, 3, 5, 7, 9, or 11, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, 9, or 11, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a BAL1 and/or BBAP nucleotide sequence can be prepared by standard synthetic techniques, i.e., using an automated DNA synthesizer.

Probes based on the BAL1 and/or BBAP nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a BAL1 and/or BBAP protein, such as by measuring a level of a BAL1 and/or BBAP-encoding nucleic acid in a sample of cells from a subject, i.e., detecting BAL1 and/or BBAP mRNA levels.

Nucleic acid molecules encoding other BAL1 and/or BBAP members and thus which have a nucleotide sequence which differs from the BAL1 and/or BBAP sequences of SEQ ID NOs: 1, 3, 5, 7, 9, or 11, or fragment thereof, are contemplated. Moreover, nucleic acid molecules encoding BAL1 and/or BBAP proteins from different species, and thus which have a nucleotide sequence which differs from the BAL1 and/or BBAP sequences of SEQ ID NOs: 1, 3 5, 7, 9, or 11 are also intended to be within the scope of the present invention. For example, rat or monkey BAL1 and/or BBAP cDNA can be identified based on the nucleotide sequence of a human and/or mouse BAL1 and/or BBAP. In one embodiment, the nucleic acid molecule(s) of the invention encodes a protein or portion thereof which includes an amino acid sequence which is sufficiently homologous to an amino acid sequence of SEQ ID NO: 2, 4, 6, 8, 10, or 12, or fragment thereof, such that the protein or portion thereof modulates (e.g., enhance), one or more of the following biological activities: a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR).

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, 10, or 12, or fragment thereof) amino acid residues to an amino acid sequence of SEQ ID NO: 2, 4, 6, 8, 10, or 12, or fragment thereof, such that the protein or portion thereof modulates (e.g., enhance) one or more of the following biological activities: a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR).

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO: 2, 4, 6, 8, 10, or 12, or a fragment thereof.

Portions of proteins encoded by the BAL1 and/or BBAP nucleic acid molecule of the invention are preferably biologically active portions of the BAL1 and/or BBAP protein. As used herein, the term "biologically active portion of BAL1 and/or BBAP" is intended to include a portion, e.g., a domain/motif, of BAL1 and/or BBAP that has one or more of the biological activities of the full-length BAL1 and/or BBAP protein.

Standard binding assays, e.g., immunoprecipitations and yeast two-hybrid assays, as described herein, or functional assays, e.g., RNAi or overexpression experiments, can be performed to determine the ability of a BAL1 and/or BBAP protein or a biologically active fragment thereof to maintain a biological activity of the full-length BAL1 and/or BBAP protein.

The invention further encompasses nucleic acid molecules that differ from the nucleotide sequence shown in SEQ ID NO: 1, 3, 5, 7, 9, or 11, or fragment thereof due to degeneracy of the genetic code and thus encode the same BAL1 and/or BBAP protein as that encoded by the nucleotide sequence shown in SEQ ID NO: 1, 3, 5, 7, 9, or 11, or fragment thereof. In another embodiment, an isolated nucleic acid molecule of the invention has a nucleotide sequence encoding a protein having an amino acid sequence shown in SEQ ID NO: 2, 4, 6, 8, 10, or 12, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO: 2, 4, 6, 8, 10, or 12, or fragment thereof, or a fragment thereof. In another embodiment, a nucleic acid encoding a BAL1 and/or BBAP polypeptide consists of nucleic acid sequence encoding a portion of a full-length BAL1 and/or BBAP fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of BAL1 and/or BBAP may exist within a population (e.g., a mammalian and/or human population). Such genetic polymorphism in the BAL1 and/or BBAP gene may exist among individuals within a population due to natural allelic variation. As used herein, the terms "gene" and "recombinant gene" refer to nucleic acid molecules comprising an open reading frame encoding a BAL1 and/or BBAP protein, preferably a mammalian, e.g., human, BAL1 and/or BBAP protein. Such natural allelic variations can typically result in 1-5% variance in the nucleotide sequence of the BAL1 and/or BBAP gene. Any and all such nucleotide variations and resulting amino acid polymorphisms in BAL1 and/or BBAP that are the result of natural allelic variation and that do not alter the functional activity of BAL1 and/or BBAP are intended to be within the scope of the invention. Moreover, nucleic acid molecules encoding BAL1 and/or BBAP proteins from other species, and thus which have a nucleotide sequence which differs from the human or mouse sequences of SEQ ID NO: 1, 3, 5, or 7, are intended to be within the scope of the invention. Nucleic acid molecules corresponding to natural allelic variants and homologues of the human or mouse BAL1 and/or BBAP cDNAs of the invention can be isolated based on their homology to the human or mouse BAL1 and/or BBAP nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the BAL1 and/or BBAP sequence that may exist in the population, the skilled artisan will further appreciate that changes can be introduced by mutation into the nucleotide sequence of SEQ ID NO: 1, 3, 5, 7, 9, or 11, or fragment thereof, thereby leading to changes in the amino acid sequence of the encoded BAL1 and/or BBAP protein, without altering the functional ability of the BAL1 and/or BBAP protein. For example, nucleotide substitutions leading to amino acid substitutions at "non-essential" amino acid residues can be made in the sequence of SEQ ID NO: 1, 3, 5, 7, 9, or 11, or fragment thereof. A "non-essential" amino acid residue is a residue that can be altered from the wild-type sequence of BAL1 and/or BBAP (e.g., the sequence of SEQ ID NO: 2, 4, 6, 8, 10, or 12, or fragment thereof) without altering the activity of BAL1 and/or BBAP, whereas an "essential" amino acid residue is required for BAL1 and/or BBAP activity. Other amino acid residues, however, (e.g., those that are not conserved or only semi-conserved between mouse and human) may not be essential for activity and thus are likely to be amenable to alteration without altering BAL1 and/or BBAP activity.

Accordingly, another aspect of the invention pertains to nucleic acid molecules encoding BAL1 and/or BBAP proteins that contain changes in amino acid residues that are not essential for BAL1 and/or BBAP activity. Such BAL1 and/or BBAP proteins differ in amino acid sequence from SEQ ID NO: 2, 4, 6, 8, 10, or 12, or fragment thereof, yet retain at least one of the BAL1 and/or BBAP activities described herein. In one embodiment, the isolated nucleic acid molecule comprises a nucleotide sequence encoding a protein, wherein the protein lacks one or more BAL1 and/or BBAP domains (e.g., BAL1-binding, BBAP-binding, BBAP dimerization, macro1, macro 2, PARP, and/or RING domains).

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a BAL1 and/or BBAP protein homologous to the protein of SEQ ID NO: 2, 4, 6, 8, 10, or 12, or fragment thereof, can be created by introducing one or more nucleotide substitutions, additions or deletions into the nucleotide sequence of SEQ ID NO: 1, 3, 5, 7, 9, or 11, or fragment thereof, or a homologous nucleotide sequence such that one or more amino acid substitutions, additions or deletions are introduced into the encoded protein. Mutations can be introduced into SEQ ID NO: 1, 3, 5, 7, 9, or 11, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), bet217-420 ranched side chains (e.g., threonine, valine, isoleucine) and aromatic side chains (e.g., tyrosine, phenylalanine, tryptophan, histidine). Thus, a predicted nonessential amino acid residue in BAL1 and/or BBAP is preferably replaced with another amino acid residue from the same side chain family. Alternatively, in another embodiment, mutations can be introduced randomly along all or part of a BAL1 and/or BBAP coding sequence, such as by saturation mutagenesis, and the resultant mutants can be screened for a BAL1 and/or BBAP activity described herein to identify mutants that retain BAL1 and/or BBAP activity. Following mutagenesis of SEQ ID NO: 1, 3, 5, 7, 9, or 11, or fragment thereof, the encoded protein can be expressed recombinantly (as described herein) and the activity of the protein can be determined using, for example, assays described herein.

BAL1 and/or BBAP levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, BAL1 and/or BBAP levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the BAL1 and/or BBAP mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding BAL1 and/or BBAP. Other suitable probes for use in the diagnostic assays of the invention are described herein. Hybridization of an mRNA with the probe indicates that BAL1 and/or BBAP is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the BAL1 and/or BBAP mRNA expression levels.

An alternative method for determining the BAL1 and/or BBAP mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the BAL1 and/or BBAP mRNA.

As an alternative to making determinations based on the absolute BAL1 and/or BBAP expression level, determinations may be based on the normalized BAL1 and/or BBAP expression level. Expression levels are normalized by correcting the absolute BAL1 and/or BBAP expression level by comparing its expression to the expression of a non-BAL1 and/or BBAP gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a BAL1 and/or BBAP protein can also be detected and/or quantified by detecting or quantifying the expressed polypeptide. The BAL1 and/or BBAP polypeptide can be detected and quantified by any of a number of means well known to those of skill in the art.

These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express BAL1 and/or BBAP.

In addition to the nucleic acid molecules encoding BAL1 and/or BBAP proteins described above, another aspect of the invention pertains to isolated nucleic acid molecules which are antisense thereto. An "antisense" nucleic acid comprises a nucleotide sequence which is complementary to a "sense" nucleic acid encoding a protein, i.e., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire BAL1 and/or BBAP coding strand, or to only a portion thereof. In one embodiment, an antisense nucleic acid molecule is antisense to a "coding region" of the coding strand of a nucleotide sequence encoding BAL1 and/or BBAP. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding BAL1 and/or BBAP. The term "noncoding region" refers to 5' and 3' sequences which flank the coding region that are not translated into amino acids (i.e., also referred to as 5' and 3' untranslated regions).

In some embodiments, BAL1 and/or BBAP expression can be reduced using nucleic acid compositions described herein. For example, an "RNA interfering agent," as used herein, is defined as any agent which interferes with or inhibits expression of a target gene, e.g., BAL1 and/or BBAP, by RNA interference (RNAi). Such RNA interfering agents include, but are not limited to, nucleic acid molecules including RNA molecules which are homologous to the target gene or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated be reference herein).

RNA interfering agents, e.g., siRNA molecules, may be administered to a subject having or at risk for a condition described herein mediated by BAL1 and/or BBAP, to inhibit expression of BAL1 and/or BBAP to thereby treat, prevent, or inhibit the condition in the subject.

II. Recombinant Expression Vectors and Host Cells

Another aspect of the invention pertains to the use of vectors, preferably expression vectors, containing a nucleic acid encoding BAL1 and/or BBAP (or a portion or complex thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a BAL1 and/or BBAP nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of BAL1 and/or BBAP in prokaryotic or eukaryotic cells. For example, BAL1 and/or BBAP can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the BAL1 and/or BBAP is cloned into a pGEX expression vector to create a vector encoding a fusion protein comprising, from the N-terminus to the C-terminus, and/or GST-thrombin cleavage site-BAL1 and/or BBAP. The fusion protein can be purified by affinity chromatography using glutathione-agarose resin. Recombinant BAL1 and/or BBAP unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the BAL1 and/or BBAP expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, BAL1 and/or BBAP can be expressed in insect cells using baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to BAL1 and/or BBAP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, BAL1 and/or BBAP protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. A BAL1 and/or BBAP polypeptide or fragment thereof, may be secreted and isolated from a mixture of cells and medium containing the polypeptide. Alternatively, a BAL1 and/or BBAP polypeptide or fragment thereof, may be retained cytoplasmically and the cells harvested, lysed and the protein or protein complex isolated. A BAL1 and/or BBAP polypeptide or fragment thereof, may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of BAL1 and/or BBAP or a fragment thereof. In other embodiments, heterologous tags can be used for purification purposes (e.g., epitope tags and FC fusion tags), according to standards methods known in the art.

Thus, a nucleotide sequence encoding all or a selected portion of a BAL1 and/or BBAP polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant BAL1 and/or BBAP polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the BAL1 and/or BBAP polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full-length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding BAL1 and/or BBAP or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) BAL1 and/or BBAP protein. Accordingly, the invention further provides methods for producing BAL1 and/or BBAP protein using the host cells of the invention. In one embodiment, the method comprises culturing the host cell of invention (into which a recombinant expression vector encoding BAL1 and/or BBAP has been introduced) in a suitable medium until BAL1 and/or BBAP is produced. In another embodiment, the method further comprises isolating BAL1 and/or BBAP from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which BAL1 and/or BBAP encoding sequences, or fragments thereof, have been introduced. Such host cells can then be used to create non-human transgenic animals in which exogenous BAL1 and/or BBAP sequences have been introduced into their genome or homologous recombinant animals in which endogenous BAL1 and/or BBAP sequences have been altered. Such animals are useful for studying the function and/or activity of BAL1 and/or BBAP, or fragments thereof, and for identifying and/or evaluating modulators of BAL1 and/or BBAP activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous BAL1 and/or BBAP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding BAL1 and/or BBAP, or a fragment thereof, into the male pronuclei of a fertilized oocyte, e.g., by microinjection, retroviral infection, and allowing the oocyte to develop in a pseudopregnant female foster animal. A human BAL1 and/or BBAP cDNA sequence can be introduced as a transgene into the genome of a nonhuman animal. Alternatively, a nonhuman homologue of the human BAL1 and/or BBAP gene can be used as a transgene. Intronic sequences and polyadenylation signals can also be included in the transgene to increase the efficiency of expression of the transgene. A tissue-specific regulatory sequence(s) can be operably linked to the BAL1 and/or BBAP transgene to direct expression of BAL1 and/or BBAP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the BAL1 and/or BBAP transgene in its genome and/or expression of BAL1 and/or BBAP mRNA in tissues or cells of the animals. A transgenic founder animal can then be used to breed additional animals carrying the transgene. Moreover, transgenic animals carrying a transgene encoding BAL1 and/or BBAP can further be bred to other transgenic animals carrying other transgenes.

To create a homologous recombinant animal, a vector is prepared which contains at least a portion of a BAL1 and/or BBAP gene into which a deletion, addition or substitution has been introduced to thereby alter, e.g., functionally disrupt, the BAL1 and/or BBAP gene. The BAL1 and/or BBAP gene can be a human gene, but more preferably, is a nonhuman homologue of a human BAL1 and/or BBAP gene. For example, a mouse BAL1 and/or BBAP gene can be used to construct a homologous recombination vector suitable for altering an endogenous BAL1 and/or BBAP gene, respectively, in the mouse genome. In a preferred embodiment, the vector is designed such that, upon homologous recombination, the endogenous BAL1 and/or BBAP gene is functionally disrupted in some manner (e.g., no longer encodes a functional protein, no longer encodes one or more functional domain(s), etc.; also referred to as a "knock out" vector). Alternatively, the vector can be designed such that, upon homologous recombination, the endogenous BAL1 and/or BBAP gene is mutated or otherwise altered but still encodes functional protein (e.g., the upstream regulatory region can be altered to thereby alter the expression of the endogenous BAL1 and/or BBAP protein). In the homologous recombination vector, the altered portion of the BAL1 and/or BBAP gene is flanked at its 5' and 3' ends by additional nucleic acid of the BAL1 and/or BBAP gene to allow for homologous recombination to occur between the exogenous BAL1 and/or BBAP gene carried by the vector and an endogenous BAL1 and/or BBAP gene in an embryonic stem cell. The additional flanking BAL1 and/or BBAP nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced BAL1 and/or BBAP gene has homologously recombined with the endogenous BAL1 and/or BBAP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated BAL1 and/or BBAP Polypeptides and Anti-BAL1 and/or BBAP Antibodies The present invention provides soluble, purified and/or isolated forms of BAL1 and/or BBAP, or fragments thereof. In addition, it is to be understood that any and all attributes of the BAL1 and BBAP polypeptides described herein, such as percentage identities, polypeptide lengths, polypeptide fragments, biological activities, antibodies, etc. can be combined in any order or combination with respect to BAL1, BBAP, and/or BAL1-BBAP complexes.

In one aspect, a BAL1 and/or BBAP polypeptide may comprise a full-length BAL1 and/or BBAP amino acid sequence or a full-length BAL1 and/or BBAP amino acid sequence with 1 to about 20 conservative amino acid substitutions Amino acid sequence of any BAL1 and/or BBAP polypeptide described herein can also be at least 50, 55, 60, 65, 70, 75, 80, 85, 90, 91, 92, 93, 94, 95, 96, 97, 98, 99, or 99.5% identical to a BAL1 and/or BBAP polypeptide sequence of interest, described herein, well known in the art, or a fragment thereof. In addition, any BAL1 and/or BBAP polypeptide, or fragment thereof, described herein has modulates (e.g., enhance) one or more of the following biological activities: a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR). In another aspect, the present invention contemplates a composition comprising an isolated BAL1 and/or BBAP polypeptide and less than about 25%, or alternatively 15%, or alternatively 5%, contaminating biological macromolecules or polypeptides.

The present invention further provides compositions related to producing, detecting, or characterizing a BAL1 and/or BBAP polypeptide, or fragment thereof, such as nucleic acids, vectors, host cells, and the like. Such compositions may serve as compounds that modulate a BAL1 and/or BBAP polypeptide's expression and/or activity, such as antisense nucleic acids.

In certain embodiments, a BAL1 and/or BBAP polypeptide of the invention may be a fusion protein containing a domain which increases its solubility and bioavailability and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a BAL1 and/or BBAP polypeptide of the invention may comprise one or more heterologous fusions. Polypeptides may contain multiple copies of the same fusion domain or may contain fusions to two or more different domains. The fusions may occur in within the polypeptide as an in-frame insertion, at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, BAL1 and/or BBAP polypeptides, or fragments thereof, are fused to an antibody fragment (e.g., Fc polypeptides). Techniques for preparing these fusion proteins are known, and are described, for example, in WO 99/31241 and in Cosman et. al., 2001 Immunity 14:123 133. Fusion to an Fc polypeptide offers the additional advantage of facilitating purification by affinity chromatography over Protein A or Protein G columns.

In still another embodiment, a BAL1 and/or BBAP polypeptide may be labeled with a fluorescent label to facilitate their detection, purification, or structural characterization. In an exemplary embodiment, a BAL1 and/or BBAP polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated BAL1 and/or BBAP proteins, and biologically active portions thereof, as well as peptide fragments suitable for use as immunogens to raise anti-BAL1 and/or BBAP antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of BAL1 and/or BBAP protein in which the protein is separated from cellular components of the cells in which it is naturally or recombinantly produced. In one embodiment, the language "substantially free of cellular material" includes preparations of BAL1 and/or BBAP protein having less than about 30% (by dry weight) of non-BAL1 and/or BBAP protein (also referred to herein as a "contaminating protein"), more preferably less than about 20% of non-BAL1 and/or BBAP protein, still more preferably less than about 10% of non-BAL1 and/or BBAP protein, and most preferably less than about 5% non-BAL1 and/or BBAP protein. When the BAL1 and/or BBAP protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of BAL1 and/or BBAP protein in which the protein is separated from chemical precursors or other chemicals which are involved in the synthesis of the protein. In one embodiment, the language "substantially free of chemical precursors or other chemicals" includes preparations of BAL1 and/or BBAP protein having less than about 30% (by dry weight) of chemical precursors of non-BAL1 and/or BBAP chemicals, more preferably less than about 20% chemical precursors of non-BAL1 and/or BBAP chemicals, still more preferably less than about 10% chemical precursors of non-BAL1 and/or BBAP chemicals, and most preferably less than about 5% chemical precursors of non-BAL1 and/or BBAP chemicals. In preferred embodiments, isolated proteins or biologically active portions thereof lack contaminating proteins from the same animal from which the BAL1 and/or BBAP protein is derived. Typically, such proteins are produced by recombinant expression of, for example, a human BAL1 and/or BBAP protein in a nonhuman cell.

In preferred embodiments, the protein or portion thereof comprises an amino acid sequence which is sufficiently homologous to an amino acid sequence of SEQ ID NO: 2, 4, 6, 8, 10, or 12, or fragment thereof, such that the protein or portion thereof maintains one or more of the following biological activities or, in complex, modulates (e.g., enhance) one or more of the following biological activities: a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR). The portion of the protein is preferably a biologically active portion as described herein. In another preferred embodiment, the BAL1 and/or BBAP protein has an amino acid sequence shown in SEQ ID NO: 2, 4, 6, 8, 10, or 12, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 2, 4, 6, 8, 10, or 12, or fragment thereof. In yet another preferred embodiment, the BAL1 and/or BBAP protein has an amino acid sequence which is encoded by a nucleotide sequence which hybridizes, e.g., hybridizes under stringent conditions, to the nucleotide sequence of SEQ ID NO:1, 3, 5, 7, 9, or 11, or fragment thereof, or a nucleotide sequence which is at least about 50%, preferably at least about 60%, more preferably at least about 70%, yet more preferably at least about 80%, still more preferably at least about 90%, and most preferably at least about 95%, 96%, 97%, 98%, 99% or more homologous to the nucleotide sequence shown in SEQ ID NO: 1, 3, 5, 7, 9, or 11, or fragment thereof. The preferred BAL1 and/or BBAP proteins of the present invention also preferably possess at least one of the BAL1 and/or BBAP biological activities, or activities associated with the complex, described herein. For example, a preferred BAL1 and/or BBAP protein of the present invention includes an amino acid sequence encoded by a nucleotide sequence which hybridizes, e.g., hybridizes under stringent conditions, to the nucleotide sequence of SEQ ID NO:1, 3, 5, 7, 9, or 11, or fragment thereof and which can maintain one or more of the following biological activities or, in complex, modulates (e.g., enhance) one or more of the following biological activities: a) binding to a BAL1 polypeptide or fragment thereof; b) binding to a BBAP polypeptide or fragment thereof; c) forming a BAL1-BBAP complex; d) inhibiting localization and/or binding of BAL1 and/or BBAP to DNA damage sites; e) inhibiting binding of BAL1 to poly(ADP-ribose) (PAR) chains; f) inhibiting BBAP monoubiquitylation of histones; g) inhibiting BBAP-mediated methylation of histones; h) inhibiting localization and/or binding to DNA damage sites of at least one polypeptide selected from the group consisting of 53 BP1, RAP80, BRCA1, ATM, γH2AX, and MDC1; and i) inhibiting DNA damage responses (DDR).

Biologically active portions of the BAL1 and/or BBAP protein include peptides comprising amino acid sequences derived from the amino acid sequence of the BAL1 and/or BBAP protein, e.g., the amino acid sequence shown in SEQ ID NO: 2, 4, 6, 8, 10, or 12, or fragment thereof, or the amino acid sequence of a protein homologous to the BAL1 and/or BBAP protein, which include fewer amino acids than the full length BAL1 and/or BBAP protein or the full length protein which is homologous to the BAL1 and/or BBAP protein, and exhibit at least one activity of the BAL1 and/or BBAP protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., BAL1-binding, BBAP-binding, BBAP dimerization, macro1, macro 2, PARP, and/or RING domains. In a preferred embodiment, the biologically active portion of the protein which includes one or more the domains/motifs described herein can modulate DDR, especially in cancer cells. Moreover, other biologically active portions, in which other regions of the protein are deleted, can be prepared by recombinant techniques and evaluated for one or more of the activities described herein. Preferably, the biologically active portions of the BAL1 and/or BBAP protein include one or more selected domains/motifs or portions thereof having biological activity. In an exemplary embodiment, a BAL1 and/or BBAP fragment comprises and/or consists of about amino acids 30-140, 30-140, 73-140, 73-150, 1-140, 1-150, or any range in between residues 1 and 150 of SEQ ID NO:2. In another embodiment, a BAL1 and/or BBAP fragment consists of a portion of a full-length BAL1 and/or BBAP fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

BAL1 and/or BBAP proteins can be produced by recombinant DNA techniques. For example, a nucleic acid molecule encoding the protein is cloned into an expression vector (as described above), the expression vector is introduced into a host cell (as described above) and the BAL1 and/or BBAP protein is expressed in the host cell. The BAL1 and/or BBAP protein can then be isolated from the cells by an appropriate purification scheme using standard protein purification techniques. Alternative to recombinant expression, a BAL1 and/or BBAP protein, polypeptide, or peptide can be synthesized chemically using standard peptide synthesis techniques. Moreover, native BAL1 and/or BBAP protein can be isolated from cells (e.g., lymphoma cells), for example using an anti-BAL1 and/or BBAP antibody (described further below).

The invention also provides BAL1 and/or BBAP chimeric or fusion proteins. As used herein, a BAL1 and/or BBAP "chimeric protein" or "fusion protein" comprises a BAL1 and/or BBAP polypeptide operatively linked to a non-BAL1 and/or BBAP polypeptide. A "BAL1 and/or BBAP polypeptide" refers to a polypeptide having an amino acid sequence corresponding to BAL1 and/or BBAP, whereas a "non-BAL1 and/or BBAP polypeptide" refers to a polypeptide having an amino acid sequence corresponding to a protein which is not substantially homologous to the BAL1 and/or BBAP protein, respectively, e.g., a protein which is different from the BAL1 and/or BBAP protein and which is derived from the same or a different organism. Within the fusion protein, the term "operatively linked" is intended to indicate that the BAL1 and/or BBAP polypeptide and the non-BAL1 and/or BBAP polypeptide are fused in-frame to each other. The non-BAL1 and/or BBAP polypeptide can be fused to the N-terminus or C-terminus of the BAL1 and/or BBAP polypeptide, respectively. For example, in one embodiment the fusion protein is a BAL1 and/or BBAP-GST and/or BAL1 and/or BBAP-Fc fusion protein in which the BAL1 and/or BBAP sequences, respectively, are fused to the N-terminus of the GST or Fc sequences. Such fusion proteins can facilitate the purification, expression, and/or bioavailability of recombinant BAL1 and/or BBAP. In another embodiment, the fusion protein is a BAL1 and/or BBAP protein containing a heterologous signal sequence at its C-terminus. In certain host cells (e.g., mammalian host cells), expression and/or secretion of BAL1 and/or BBAP can be increased through use of a heterologous signal sequence.

Preferably, a BAL1 and/or BBAP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A BAL1 and/or BBAP-encoding nucleic acid can be cloned into such an expression vector such that the fusion moiety is linked in-frame to the BAL1 and/or BBAP protein.

The present invention also pertains to homologues of the BAL1 and/or BBAP proteins which function as either a BAL1 and/or BBAP agonist (mimetic) or a BAL1 and/or BBAP antagonist. In a preferred embodiment, the BAL1 and/or BBAP agonists and antagonists stimulate or inhibit, respectively, a subset of the biological activities of the naturally occurring form of the BAL1 and/or BBAP protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the BAL1 and/or BBAP protein. For example, BAL1 and/or BBAP protein fragments can be used to restrict localization of the BAL1-BBAP complex from the nucleus, thereby inhibiting DDR.

Homologues of the BAL1 and/or BBAP protein can be generated by mutagenesis, e.g., discrete point mutation or truncation of the BAL1 and/or BBAP protein. As used herein, the term "homologue" refers to a variant form of the BAL1 and/or BBAP protein which acts as an agonist or antagonist of the activity of the BAL1 and/or BBAP protein. An agonist of the BAL1 and/or BBAP protein can retain substantially the same, or a subset, of the biological activities of the BAL1 and/or BBAP protein. An antagonist of the BAL1 and/or BBAP protein can inhibit one or more of the activities of the naturally occurring form of the BAL1 and/or BBAP protein, by, for example, competitively binding to a downstream or upstream member of the BAL1 and/or BBAP cascade which includes the BAL1 and/or BBAP protein.

In an alternative embodiment, homologues of the BAL1 and/or BBAP protein can be identified by screening combinatorial libraries of mutants, e.g., truncation mutants, of the BAL1 and/or BBAP protein for BAL1 and/or BBAP protein agonist or antagonist activity. In one embodiment, a variegated library of BAL1 and/or BBAP variants is generated by combinatorial mutagenesis at the nucleic acid level and is encoded by a variegated gene library. A variegated library of BAL1 and/or BBAP variants can be produced by, for example, enzymatically ligating a mixture of synthetic oligonucleotides into gene sequences such that a degenerate set of potential BAL1 and/or BBAP sequences is expressible as individual polypeptides, or alternatively, as a set of larger fusion proteins (e.g., for phage display) containing the set of BAL1 and/or BBAP sequences therein. There are a variety of methods which can be used to produce libraries of potential BAL1 and/or BBAP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential BAL1 and/or BBAP sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of the BAL1 and/or BBAP protein coding can be used to generate a variegated population of BAL1 and/or BBAP fragments for screening and subsequent selection of homologues of a BAL1 and/or BBAP protein. In one embodiment, a library of coding sequence fragments can be generated by treating a double stranded PCR fragment of a BAL1 and/or BBAP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the BAL1 and/or BBAP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of BAL1 and/or BBAP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify BAL1 and/or BBAP homologues (Arkin and Youvan (1992) Proc. Natl. Acad. Sci. USA 89:7811-7815; Delagrave et al. (1993) Protein Engineering 6(3):327-331).

In another aspect, an isolated BAL1 and/or BBAP protein, or a a fragment thereof, can be used as an immunogen to generate antibodies that bind BAL1 and/or BBAP, or the complex thereof, using standard techniques for polyclonal and monoclonal antibody preparation. The full-length BAL1 and/or BBAP protein can be used or, alternatively, antigenic peptide fragments of BAL1 and/or BBAP, or peptides in complex, can be used as immunogens. A BAL1 and/or BBAP immunogen typically is used to prepare antibodies by immunizing a suitable subject, (e.g., rabbit, goat, mouse or other mammal) with the immunogen. An appropriate immunogenic preparation can contain, for example, recombinantly expressed BAL1 and/or BBAP protein or a chemically synthesized BAL1 and/or BBAP peptide. The preparation can further include an adjuvant, such as Freund's complete or incomplete adjuvant, or similar immunostimulatory agent Immunization of a suitable subject with an immunogenic BAL1 and/or BBAP preparation induces a polyclonal anti-BAL1 and/or BBAP antibody response.

Accordingly, another aspect of the invention pertains to the use of anti-BAL1 and/or BBAP antibodies. The term "antibody" as used herein refers to immunoglobulin molecules and immunologically active portions of immunoglobulin molecules, i.e., molecules that contain an antigen binding site which specifically binds (immunoreacts with) an antigen, such as BAL1 and/or BBAP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind BAL1 and/or BBAP. The term "monoclonal antibody" or "monoclonal antibody composition", as used herein, refers to a population of antibody molecules that contain only one species of an antigen binding site capable of immunoreacting with a particular epitope of BAL1 and/or BBAP. A monoclonal antibody composition thus typically displays a single binding affinity for a particular BAL1 and/or BBAP protein with which it immunoreacts.

Polyclonal anti-BAL1 and/or BBAP antibodies can be prepared as described above by immunizing a suitable subject with a BAL1 and/or BBAP immunogen, or fragment thereof. The anti-BAL1 and/or BBAP antibody titer in the immunized subject can be monitored over time by standard techniques, such as with an enzyme linked immunosorbent assay (ELISA) using immobilized BAL1 and/or BBAP. If desired, the antibody molecules directed against BAL1 and/or BBAP can be isolated from the mammal (e.g., from the blood) and further purified by well known techniques, such as protein A chromatography to obtain the IgG fraction. At an appropriate time after immunization, i.e., when the anti-BAL1 and/or BBAP antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a BAL1 and/or BBAP immunogen as described above, and the culture supernatants of the resulting hybridoma cells are screened to identify a hybridoma producing a monoclonal antibody that binds BAL1 and/or BBAP.

Any of the many well-known protocols used for fusing lymphocytes and immortalized cell lines can be applied for the purpose of generating an anti-BAL1 and/or BBAP monoclonal antibody (see, i.e., G. Galfre et al. (1977) *Nature* 266:550-52; Gefter et al. *Somatic Cell Genet.*, cited supra; Lerner, Yale J. Biol. Med., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind BAL1 and/or BBAP, i.e., using a standard ELISA assay.

As an alternative to preparing monoclonal antibody-secreting hybridomas, a monoclonal anti-BAL1 and/or BBAP antibody can be identified and isolated by screening a recombinant combinatorial immunoglobulin library (e.g., an antibody phage display library) with BAL1 and/or BBAP to thereby isolate immunoglobulin library members that bind BAL1 and/or BBAP. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. Nature (1990) 348:552-554.

Additionally, recombinant anti-BAL1 and/or BBAP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314: 446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-BAL1 and/or BBAP antibody (e.g., monoclonal antibody) can be used to isolate BAL1 and/or BBAP by standard techniques, such as affinity chromatography or immunoprecipitation. An anti-BAL1 and/or BBAP antibody can facilitate the purification of natural BAL1 and/or BBAP from cells and of recombinantly produced BAL1 and/or BBAP expressed in host cells. Moreover, an anti-BAL1 and/or BBAP antibody can be used to detect BAL1 and/or BBAP protein (e.g., in a cellular lysate or cell supernatant) in order to evaluate the abundance and pattern of expression of the BAL1 and/or BBAP protein. In some embodiments, for example, such antibodies can be used in quantitative immunohistochemical assays to determine or predict the efficacy of a cancer therapy. Thus, anti-BAL1 and/or BBAP antibodies can be used to monitor protein levels in a cell or tissue, e.g., cancer cells or tissue, as part of a clinical testing procedure, e.g., in order to monitor the efficacy of a cancer therapy. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In vivo techniques for detection of BAL1 and/or BBAP protein include introducing into a subject a labeled antibody directed against the protein. For example, the antibody can be labeled with a radioactive marker whose presence and location in a subject can be detected by standard imaging techniques.

IV. Identification of Compounds that Modulate BAL1 and/or BBAP

The BAL1 and/or BBAP nucleic acid and polypeptide molecules described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In one aspect, modulators, inhibitors, or antagonists against the polypeptides of the invention, biological complexes containing them, or orthologues thereof, may be used to treat any disease or other treatable condition of a patient (including humans and animals), including, for example, cancer.

Modulators of BAL1 and/or BBAP nucleic acid and polypeptide molecules, may be identified and developed as set forth below using techniques and methods known to those of skill in the art. The modulators of the invention may be employed, for instance, to inhibit and treat BAL1 and/or BBAP-mediated diseases or disorders. The modulators of the invention may elicit a change in one or more of the following activities: (a) a change in the level and/or rate of formation of a BAL1-BBAP complex, (b) a change in the activity of a BAL1 and/or BBAP nucleic acid and/or polypeptide, (c) a change in the stability of a BAL1 and/or BBAP nucleic acid and/or polypeptide, (d) a change in the conformation of a BAL1 and/or BBAP nucleic acid and/or polypeptide, or (e) a change in the activity of at least one polypeptide contained in a BAL1-BBAP complex. A number of methods for identifying a molecule which modulates a BAL1 and/or BBAP nucleic acid and/or polypeptide are known in the art. For example, in one such method, a BAL1 and/or BBAP nucleic acid and/or polypeptide, is contacted with a test compound, and the activity of the BAL1 and/or BBAP nucleic acid and/or polypeptide is determined in the presence of the test compound, wherein a change in the activity of the BAL1 and/or BBAP nucleic acid and/or polypeptide in the presence of the compound as compared to the activity in the absence of the compound (or in the presence of a control compound) indicates that the test compound modulates the activity of the BAL1 and/or BBAP nucleic acid and/or polypeptide.

Compounds to be tested for their ability to act as modulators of BAL1 and/or BBAP nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of a BAL1 and/or BBAP polypeptide (e.g., a dominant negative form that binds to, but does not activate, BAL1 and/or BBAP).

A variety of assay formats will suffice and, in light of the present disclosure, those not expressly described herein may nevertheless be comprehended by one of ordinary skill in the art based on the teachings herein. Assay formats for analyzing BAL1-BBAP complex formation and/or activity of a BAL1 and/or BBAP nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate a BAL1 and/or BBAP, for example, by enhancing the formation of a BAL1 and/or BBAP, by enhancing the binding of a BAL1 and/or BBAP to a substrate, and/or by enhancing the binding of a BAL1 and/or BBAP polypeptide to a substrate. Another example of an assay useful for identifying a modulator of a BAL1 and/or BBAP is a competitive assay that combines one or more BAL1 and/or BBAP polypeptides with a potential modulator, such as, for example, polypeptides, nucleic acids, natural substrates or ligands, or substrate or ligand mimetics, under appropriate conditions for a competitive inhibition assay. BAL1 and/or BBAP polypeptides can be labeled, such as by radioactivity or a colorimetric compound, such that BAL1 and/or BBAP complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting BAL1 and/or BBAPes polypeptides or complexes, as described above.

Complex formation between a BAL1 and/or BBAP polypeptide, or fragment thereof, and a binding partner (e.g., BAL1 and/or BBAP) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying BAL1-BBAP complexes described above may be incorporated into the detection methods.

In certain embodiments, it may be desirable to immobilize a BAL1 and/or BBAP polypeptide to facilitate separation of BAL1-BBAP complexes from uncomplexed forms of one or both of the proteins, as well as to accommodate automation of the assay. Binding of a BAL1 and/or BBAP polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of BAL1 and/or BBAP polypeptides found in the bead fraction quantified from the gel using standard electrophoretic techniques such as described in the appended examples.

Other techniques for immobilizing proteins on matrices are also available for use in the subject assay. For instance, a BAL1 and/or BBAP polypeptide may be immobilized utilizing conjugation of biotin and streptavidin. For instance, biotinylated polypeptide molecules may be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the BAL1 and/or BBAP polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of BAL1 and/or BBAP polypeptide trapped in the BAL1-BBAP complex may be assessed with a chromogenic substrate of the enzyme, e.g. 3,3'-diaminobenzadine terahydrochloride or 4-chloro-1-napthol. Likewise, a fusion protein comprising the BAL1 and/or BBAP polypeptide and glutathione-S-transferase may be provided, and BAL1-BBAP complex formation quantified by detecting the GST activity using 1-chloro-2,4-dinitrobenzene (Habig et al (1974) J Biol Chem 249:7130).

Antibodies against the BAL1 and/or BBAP polypeptide can be used for immunodetection purposes. Alternatively, the BAL1 and/or BBAP polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, a BAL1 and/or BBAP polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a DNA binding domain of a transcriptional activator may be fused in frame to the coding sequence for a "bait" protein, e.g., a BAL1 and/or BBAP polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a DNA binding domain that recognizes the responsive element on the reporter gene in the host cell, and (b) a bait protein (e.g., a BAL1 and/or BBAP polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA binding domain of the first hybrid protein and the transcriptional activation domain of the second hybrid protein may be derived from transcriptional activators having separable DNA binding and transcriptional activation domains. For instance, these separate DNA binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA binding domains may be used in the subject constructs; such as domains of ACE1, λcI, lac repressor, jun or fos. In another embodiment, the DNA binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the BAL1 and/or BBAP, or complex polypeptide, of interest may be generated in whole cells, taking advantage of cell culture techniques to support the subject assay. For example, the BAL1 and/or BBAP, or complex polypeptide, may be constituted in a prokaryotic or eukaryotic cell culture system. Advantages to generating the BAL1 and/or BBAP, or complex polypeptide, in an intact cell includes the ability to screen for modulators of the level and/or activity of the BAL1 and/or BBAP, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The BAL1 and/or BBAP nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of BAL1 and/or BBAP may be detected in a cell-free assay generated by constitution of a functional BAL1 and/or BBAP in a cell lysate. In an alternate format, the assay can be derived as a reconstituted protein mixture which, as described below, offers a number of benefits over lysate-based assays.

The activity of a BAL1 and/or BBAP or a BAL1 and/or BBAP polypeptide may be identified and/or assayed using a variety of methods well known to the skilled artisan. For example, the activity of a BAL1 and/or BBAP nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a BAL1 and/or BBAP nucleic acid and/or polypeptide may be assessed by monitoring changes in the phenotype of a targeted cell. For example, the detection means can include a reporter gene construct which includes a transcriptional regulatory element that is dependent in some form on the level and/or activity of a BAL1 and/or BBAP nucleic acid and/or polypeptide. The BAL1 and/or BBAP nucleic acid and/or polypeptide may be provided as a fusion protein with a domain that binds to a DNA element of a reporter gene construct. The added domain of the fusion protein can be one which, through its DNA binding ability, increases or decreases transcription of the reporter gene. Whichever the case may be, its presence in the fusion protein renders it responsive to a BAL1 and/or BBAP nucleic acid and/or polypeptide. Accordingly, the level of expression of the reporter gene will vary with the level of expression of a BAL1 and/or BBAP nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a BAL1 and/or BBAP nucleic acid and/or polypeptide present in the cell. Such embodiments of the subject assay are particularly amenable to high through-put analysis in that proliferation of the cell can provide a simple measure of inhibition of the BAL1 and/or BBAP nucleic acid and/or polypeptide.

V. Methods of the Invention

The methods of the invention relate to the modulation of the expression and/or activity of BAL1 and/or BBAP sufficient to inhibit proliferation of hyperproliferative cells and to treat cancer. In some embodiments, this can occur in vivo (e.g., within a subject). In other embodiments, this can occur in vitro (e.g., within a medium such as a cell culture medium, body fluid sample, tissue sample, etc. containing hyperproliferative cells). In still other embodiments, medicaments comprising agents useful for such inhibition are contemplated.

The term "sufficient to inhibit" is intended to encompass any decrease in expression and/or activity of BAL1 and/or BBAP that promotes, activates, stimulates, enhances, or results in inhibition of proliferation of hyperproliferative cells and/or treatment of cancer.

In one aspect, a method of treating cancer by enhancing the efficacy of cancer therapies in a subject, comprising administering to the subject an effective amount of (a) an agent that inhibits one or more functions of BAL1, BBAP, or a BAL1-BBAP complex and (b) the cancer therapy is provided. In one embodiment, the agent is a recombinant BAL1 and/or BBAP protein, or fragment thereof, or nucleic acid molecule encoding such a polypeptide. In another embodiment, the agent is an anti-sense nucleic acid molecule having a sequence complementary to BAL1 and/or BBAP (e.g., an RNAi, siRNA, or other RNA inhibiting nucleic acid molecule). In still other embodiments, the agent is a small molecule which inhibits activity of the marker; an aptamer which inhibits expression or activity of the marker. In yet other embodiments, the agent is a polypeptide described herein (e.g., a dominant negative BAL1 and/or BBAP polypeptide).

The term "administering" is intended to include routes of administration which allow the agent to perform its intended function of modulating (e.g., increasing or decreasing) expression and/or activity of BAL1 and/or BBAP. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of an agent that induces expression and/or activity of BAL1 and/or BBAP is that amount necessary or sufficient to modulate (e.g., increase or decrease) expression and/or activity of BAL1 and/or BBAP in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular respiration uncoupling agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular respiration agent to treat a cancer can be monitored by comparing two or more samples obtained from a subject undergoing cancer therapy. For example, the efficacy of cancer therapies which damage DNA, as well as agents that take advantage of DNA repair defects but do not damage DNA themselves, such as poly ADP ribose polymerase (PARP) inhibitors, as well as chemotherapy or radiation therapy, is predicted according to the methods described herein.

In one embodiment, the efficacy of chemotherapies is predicted. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. No. Re. 36,397); and NU1025 (Bowman et al.). The foregoing examples of chemotherapeutic agents are illustrative, and are not intended to be limiting.

In another embodiment, the methods described herein are useful for predicting the efficacy of radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Cancer therapies which damage DNA to a lesser extent than chemotherapy or radiation therapy may be determined to have enhanced efficacy using the methods of the invention for determining the phenotype of a cancer. Examples of such therapies include immunotherapy, hormone therapy, and gene therapy. In addition, other such therapies are known in the art, including hyperthermic therapy and photodynamic therapy (see National Cancer Institute home page at nci.nih.gov). Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be used in such therapies.

Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In one embodiment, cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

Hyperthermia, a procedure in which body tissue is exposed to high temperatures (up to 106° F.), is under investigation to assess its effectiveness in the treatment of cancer. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness.

Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

Photodynamic therapy (also called PDT, photoradiation therapy, phototherapy, or photochemotherapy) is a treatment for some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

Laser therapy involves the use of high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide (CO2) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the CO2 laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. CO2 and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with cancer therapies may vary according to the particular cancer agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

In general, it is preferable to obtain a first sample from the subject prior to begining therapy and one or more samples during treatment. In such a use, a baseline of expression of cells from subjects with cancer or cell hyperproliferative disorders prior to therapy is determined and then changes in the baseline state of expression of cells from subjects with cancer or cell hyperproliferative disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with cancer or cell hyperproliferative disorders is increasing or decreasing.

Another aspect of the present invention relates to a method of predicting the efficacy of a cancer therapy in a subject, comprising obtaining a biological sample from the subject, and comparing the amount, structure, subcellular localization, and/or activity of at least one marker selected from the group consisting of BAL1, BBAP, and/or BAL1-BBAP complex in a subject sample and the amount, structure, subcellular localization, and/or activity of the at least one marker in a control, wherein a significant difference in the amount, structure, subcellular localization, and/or activity of the at least one marker in the sample and the amount, structure, subcellular localization, and/or activity in the control is predictive of the outcome of treatment of the subject with the cancer therapy. Methods described herein can use one or more of various control samples, subjects, etc. For example, the control can be selected from the group consisting of a non-cancerous cell sample from the subject or member of the same species to which the subject belongs; anon-cancerous tissue that is the same tissue type as the cancerous tissue of the subject; and a non-cancerous tissue that is not the same tissue type as the cancerous tissue of the subject.

In yet another aspect, a method for assessing the efficacy of an agent that modulates the expression and/or activity of BAL1, BBAP, or a BAL-BBAP complex for enhancing the efficacy of a cancer therapy in a subject comprising detecting in a subject sample at a first point in time, the expression and/or activity of BAL1, BBAP, or a BAL-BBAP complex; repeating the previous step during at least one subsequent point in time after administration of the agent; and comparing the expression and/or activity detected in the comparison, wherein a significantly higher expression and/or activity of BAL1, BBAP, or a BAL-BBAP complex expression and/or activity in the first subject sample relative to at least one subsequent subject sample, indicates that the agent enhances the efficacy of the cancer therapy in the subject and/or wherein a significantly decreased amount of an activity selected from the group consisting of a) increased binding to a BAL1 polypeptide or fragment thereof; b) increased binding of a BBAP polypeptide or fragment thereof; c) increased formation of a BAL1-BBAP complex; d) inhibition of localization and/or binding of BAL1 and/or BBAP to DNA damage sites; e) inhibition of binding of BAL1 to poly(ADP-ribose) (PAR) chains; f) inhibition of BBAP monoubiquitylation of histones; g) inhibition of BBAP-mediated methylation of histones; h) inhibition of localization and/or binding to DNA damage sites of at least one polypeptide selected from the group consisting of 53 BP1, RAP80, BRCA1, ATM, γH2AX, and MDC1; and i) inhibition DNA damage responses (DDR); in the first subject sample relative to at least one subsequent subject sample, indicates that the test agent enhances the efficacy of the cancer therapy in the subject.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant BAL1 and/or BBAP polypeptides, and fragments thereof, can be administered to subjects. In some embodiments, fusion proteins can be constructed and administered which have enhanced biological properties (e.g., covalently bound BAL1-BBAP complexes discussed above). In addition, the BAL1 and/or BBAP polypeptides, and fragment thereof, can be modified according to well known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) BAL1 and/or BBAP expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) BAL1 and/or BBAP expression and/or activity, or expression and/or activity of the complex, or composition comprising an agent that modulates (e.g., enhances) BAL1 and/or BBAP expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch;

(3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) BAL1 and/or BBAP expression and/or activity, or expression and/or activity of the complex encompassed by the invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) BAL1 and/or BBAP expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) BAL1 and/or BBAP expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preserving agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) BAL1 and/or BBAP expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) BAL1 and/or BBAP expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) BAL1 and/or BBAP expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in polymer matrix/gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) BAL1 and/or BBAP expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Materials and Methods for Examples 2-9

A. Protein Depletion by siRNA

All siRNA oligonucleotides targeting DNA damage response factors (Table 2) were synthesized by Integrated DNA Technologies (Coralville, Iowa). Thereafter, the siRNAs and the control non-targeting siRNA (10 μM) were transfected into Hela cells using X-tremeGENE siRNA transfection reagent (Roche, Basel, Switzerland) according to the manufacturer's instructions. Cells were cultured for 48 hr., lysed and subjected to Nu-PAGE and Western blotting as described in Yan et al. (2009) Mol. Cell. 36:110-120. The efficiency of respective protein knockdown was assessed by immunoblotting with the following individual antibodies: BAL1 (Takeyama et al. (2003) J. Biol. Chem. 278:21930-21937); rabbit polyclonal antibody (Abeam Cambridge, Mass., #ab53796); PARP1 (mouse monoclonal antibody, BD Biosciences, Franklin Lakes, N.J., #51-6639GR); BBAP (mouse monoclonal antibody, Takeyama et al. (2003) J. Biol. Chem. 278:21930-21937 and Yan et al. (2009) Mol. Cell. 36:110-120); ATM (mouse monoclonal antibody, Santa Cruz Biotechnology, Santa Cruz, Calif. #23922); and MDC1 (rabbit polyclonal antibody, Bethyl Labs, Montgomery, Tex., #A300-051A).

TABLE 2

(siRNA sequences are disclosed as SEQ ID NOs: 13-26, respectively, in order of appearance)

| Gene* | RNA sequences | Location (bp) | 3' DNA overhanging |
|---|---|---|---|
| BAL1 siRNA#1 | 5'_GCCCACGCAUGGAUCCAAAGAAU_3'<br>5'_GGAUUCUUUGGAUCCAUGCGUGGGCCU_3' | 1915-1937<br>1939-1913 | CC |
| BAL1 siRNA#2 | 5'_CCCAUACCAGUUCUGCAAUGUGG_3'<br>5'_UACCACAUUGCAGAACUGGUAUGGGAC_3' | 2448-2470<br>2472-2446 | TA |
| BAL1 siRNA#3** | 5'_GGAAGUAGCUCUCCAGCUUCCUU_3'<br>5'_CGAAGGAAGCUGGAGAGCUACUUCCAG_3' | 160-184<br>186-158 | CG |
| PARP1 siRNA | 5'_CCAAAGGAAGGAACGCUAACAAU_3'<br>5'_AAAUUGUUAGCGUUCCUUCCUUUGGUC_3' | 3758-3780<br>3782-3756 | TT |

TABLE 2 -continued (siRNA sequences are disclosed as SEQ ID NOs: 13-26, respectively, in order of appearance)

| Gene* | RNA sequences | Location (bp) | 3' DNA overhanging |
|---|---|---|---|
| ATM siRNA | 5'_AGCUAUCAGAGAAGCUAAUAAAU_3'<br>5'_UAAUUUAUUAGCUUCUCUGAUAGCUUC_3' | 12710-12732<br>12734-12708 | TA |
| MDC1 siRNA | 5'_CCACUAGGAGAAAGACAAAUAGG_3'<br>5'_GACCUAUUUGUCUUUCUCCUAGUGGCC_3' | 5350-5372<br>5374-5348 | TC |
| RNF8 siRNA | 5'_CCCUUGUACAUAUAUCUUUAGAG_3'<br>5'_CUCUCUAAAGAUAUAUGUACAAGGGUG_3' | 3662-3584<br>3686-3660 | AG |

*NCBI reference access number: BAL1, NM_031458.2; PARP1, NM_001618.3; ATM, N000051.3; MDC1, NM_014641.2; RNF8, NM_003958
**5'-UTR specific BAL1 siRNA B. Generation of BAL1, BBAP and PARP1 Constructs The specific oligonucleotides used to generate GFP-tagged BAL1, BBAP and PARP1 constructs are listed in Table 3. Human PARP1 cDNA was purchased from OriGene Technologies (#SC119157, Rockville, Md.). cDNAs for human BAL1, BBAP (NCBI Reference Sequence: NM_031458.2.) (Aguiar et al. (2000) Blood 96:4328-4334 and Takeyama et al. (2003) J. Biol. Chem. 278:21930-21937) and PARP1 were inserted by PCR into pcDNA3.1/NT-GFPTOPO (Invitrogen, Carlsbad, Calif.) to generate the respective N-terminal tagged proteins, GFP-BAL1, GFP-BBAP, GFP-PARP1. The BAL1 cDNA was also cloned into pcDNA3.1-CT-GFP-TOPO (Invitrogen) to generate the C-terminal GFP-tagged protein (BAL1-GFP) (Supplemental Information). The GFP-tagged BAL1 domain constructs, Macros-BBD and Macro 1 (FIG. 2F), were generated by introducing a stop codon (nt2454, C-A; nt1202, C-T) into the GFP-BAL1 plasmid with appropriate DNA oligonucleotides and the QuikChange Site-Directed Mutagenesis Kit (Agilent Technologies, Santa Clara, Calif.). Macro2-BBD and Macro2Δ were generated with appropriate PCR products cloned into pcDNA3.1/NT-GFP-TOPO; Macro2 was constructed by introducing a stop codon (nt1913, C-A) into Macro2-BBD. D126A and 1E326, 327AA (IE-AA) were produced with appropriate oligonucleotides (nt704, A-C; nt1303, nt1304, nt1307, AT, A-GC, C) and site-directed mutagenesis. The double mutation BAL1 construct (DM) was generated by introducing the IE326,327AA mutation into the D126A construct.

TABLE 3

(Oligo and primer sequences are disclosed as SEQ ID NOs: 27-46, respectively, in order of appearance)

| Vector name | Pair of Oligos or primers | Location* (bp) | Wild type (bp) |
|---|---|---|---|
| GFP-BAL1 | 5'_atggacttttccatggtggccggag_3'<br>5'_ttaatcaacagggctgccacttg_3' | 104-128<br>2563-2541 | |
| Macros-BBD | 5'_gtttcagcaagtcccataAcagttctgcaatgtggt_3'<br>5'_accacattgcagaactgTtatgggacttgctgaaac_3' | 2336-2471<br>2471-2336 | C nt2454<br>G |
| Macro1 | 5'_gggaagagtgagctgggacaaTaaaccaccccttctttc_3'<br>5'_gaaagaaggggtggtttattgtcccagctcactcttccc_3' | 1216-1255<br>1255-1216 | B nt1202<br>G |
| Marco2-BBD | 5'_ctagggaagagtgagctgggacaagaaacc_3'<br>5'_accacattgcagaactgttatgggacttgctgaaac_3' | 1213-1242<br>2471-2336 | G nt2454 |
| Marco2 | 5'_ctagggaagagtgagctgggacaagaaacc_3'<br>5'_ggatccatgcgtgggcctAttacatctcttccacgttg_3' | 1213-1242<br>1930-1893 | C nt1913 |
| Macro2Δ | 5'_tggcagacggcagatgtaattgtt_3'<br>5'_ggatccatgcgtgggcctAttacatctcttccacgttg_3' | 1309-1332<br>1930-1893 | C nt1913 |
| D126A | 5'_cagtctggaaagatgCcctcaccacacatgctg_3'<br>5'_cagcatgtgtggtgaggGcatctttccagactg_3' | 689-721<br>721-689 | A nt704<br>T |
| IE326, 327AA | 5'_gtccagggccacGCtgCatggcagacggcagatg_3'<br>5'_catctgccgtctgccatGcaGCgtggccctggac_3' | 1291-1324<br>1324-1291 | AT nt1303,<br>nt1304<br>A nt1307<br>T, TA |
| GFP-BBAP | 5'_atggcctcccacctgcgccgccgtc_3'<br>5'_ttactcaattcctttggctttcagctc_3' | 90-115<br>2312-2285 | |

TABLE 3 -continued (Oligo and primer sequences are disclosed as SEQ ID NOs: 27-46, respectively, in order of appearance)

| Vector name | Pair of Oligos or primers | Location* (bp) | Wild type (bp) |
|---|---|---|---|
| GFP-PARP1 | 5'_atggcggagtcttcggataagctc_3'<br>5'_ttaccacagggaggtcttaaaattg_3' | 172-295<br>3216-3192 | |

Mutated bases in the olignucleotides are capitalized and their positions indicated (right column).
*NCBI reference access number: BAL1, NM_031458.2; BBAP, NM_138287.3; PARP1, NM_001618.3.

C. Cell Culture and In Vivo Expression of GFP-Tagged Proteins

Hela and 293T human embryonic kidney cells (ATCC) were grown in DMEM containing 10% fetal bovine serum (Invitrogen). Hela or 293 cells were transiently transfected with the indicated expression plasmids (GFP-tagged BAL1, BAL1 domains, BBAP or PARP1) for 24 hrs prior to further analysis.

In additional experiments, 5'-UTR specific (Table 3) BAL1- or control siRNA-treated Hela cells were transfected with GFP vector, GFP-BAL1 or GFP-BAL1-DM constructs; 24 hours later, these cells were cultured in the presence or absence of Dox (50 ng/ml) for an additional 24 hrs and viability was analyzed thereafter with anti-Annexin V and PI.

D. Laser Microirradiation

Cells were initially seeded on coverslips and sensitized with 10 µM 5-bromo-2' deoxyuridine (BrdU, Roche) in phenol red-free medium (Invitrogen) for 24 h at 37° C. In selected experiments, the PARP inhibitor PJ34 (51JM) (Sigma, St. Louis, Mo.) was added to the culture medium for 1 hr prior to laser microirradiation. Laser microirradiation was carried out on a Zeiss LSM51 0 NLO confocal microscope (Carl Zeiss MicroImaging, LLC, Thornwood, N.Y.) equipped with a Coherent Chameleon pulse laser focused through a 40×LD C-Apochromat NA 0.9 water immersion objective to yield a spot size of 0.5-1 µm. Cells were exposed to the Ti-Sapphire pulse laser (740 nm) for ~200 ms (fast scanning mode) at 30% laser power for 5-10 iterations. These settings generated a detectable damage response restricted to the laser path without noticeable cytotoxicity to the cells.

To ensure that cells with GFP-tagged proteins were assayed, cells with moderate levels of GFP were systematically chosen using identical Argon laser (488 nm) settings. The association and dissociation kinetics of GFP-tagged proteins at sites of laser microirradiation were monitored on the same microscope by measuring GFP fluorescence over time in the damaged region using the 488 nm argon laser. The images were detected and stored using Carl Zeiss AIM software (Carl Zeiss MicroImaging). Variations in fluorescence intensity (I) were plotted as a function of time (t) using the Zeiss AIM software. Data were normalized against the fluorescence intensity at the right time before microirradiation (10). The deviations in GFP at each time point and condition were determined by averaging values from >10 cells from a representative experiment.

E. Analysis of DNA Damage Sites of Laser Microirradiation by Confocal Microscopy Hela cells were grown on coverslips and subjected to laser microirradiation as described above. Indirect immunofluorescence was performed as previously described in Yan et al. (2009) Mol. Cell. 36:110-120 with minor modifications. Primary antibodies included BAL1 (Abcam, ab53796); PARP1 (rabbit monoclonal antibody, #9532, Cell Signaling Technology, Danvers, Mass. or mouse monoclonal antibody, BD Biosciences, #51-6639); anti-PAR (Trevigen, Gaithersburg, Md., #4335); γH2AX (Millipore, Billerica, Mass., #05-636); BBAP (mouse monoclonal antibody, Yan et al. (2009) Mol. Cell. 36:110-120) or rabbit polyclonal antibody, Bethyl, #A300-833A); FK2 (multi-ubiquitin monoclonal antibody, Enzo Life Sciences International, Plymouth Meeting, Pa., #SPA-205); ATM (mouse monoclonal antibody, Santa Cruz Biotechnology, #23922); MDC1 (rabbit polyclonal antibody, Bethyl, #A300-051A); RAP80 (rabbit polyclonal antibody, Bethyl, #A300-763A); BRCA1 (Millipore, #07-434); 53BP1 (Santa Cruz Biotechnology, #22760); ATM-P-1981 (Millipore, clone 10H11.E12); and RNF8 (rabbit polyclonal antibody, Abcam, #ab4183). After multiple PBS washes, coverslips were incubated with FITC or Cy5-conjugated secondary antibody raised against mouse or rabbit (Alexa Fluor, Molecular Probes, Invitrogen) for 45 min and stained with PBS containing DAPI (counterstain for DNA). Slides were mounted in Vectashield mounting medium (Vector Labs, Burlingame, Calif.) after additional PBS washes. Confocal images were acquired on LSM-510 (Carl Zeiss Microimaging) mounted on Zeiss-Axiovert 100M equipped with Plan-Neofluar 403/1.3 oil immersion objective as previously reported in Yan et al. (2009) Mol. Cell. 36:110-120. All images for a given condition and immunostain over time were obtained with the same image acquisition settings.

F. Low-Dose Irradiation and Foci Formation

Gamma irradiation was performed as previously described in Yan et al. (2009) Mol. Cell 36:110-120 with minor modifications. In brief, Hela cells grown on coverslips were treated with low-dose irradiation (100 cGY) and analyzed at serial timepoints for repair foci by immunostaining with the following antibodies: anti-BAL1 (Abcam, ab53796); anti-PAR (Trevigen, Gaithersburg, Md., #4335); anti-53BP1 (Santa Cruz Biotechnology, #22760); and anti-γH2AX (Millipore, Billerica, Mass., #05-636).

53BP1 and γH2AX repair foci were identified and counted with an Image J macro program. In brief, DAPI staining was utilized to create a nuclear mask. The numbers and intensity of repair foci within the nuclear mask were captured by applying a 3µ rolling ball background reduction and maximum entropy threshold algorithm to both Cy5 (γH2AX) and FITC (53BP1) channels.

G. Co-Immunoprecipitation Assays

Hela cells were incubated with PJ-34 or medium alone for 1 hour, treated with 50 ng/ml of doxorubicin for 10 min or left untreated; subsequently, cells were harvested and lysed in Triton buffer (TBS, 1% Triton X-100 with protein inhibitors). Thereafter, cell lysates were incubated with anti-PARP1 (rabbit) antibody, anti-BAL1 (rabbit) antibody or control rabbit IgG overnight at 4° C. Protein A Sepharose beads were subsequently added to bind the IgG. After multiple washes in Triton buffer, antibody-associated proteins were released by boiling in protein sample buffer, resolved by Nu-PAGE and immunoblotted with anti-PARP1 (mouse), anti-PAR, or anti-BBAP (mouse) followed by donkey antimouse HRP or anti-SAL 1 antibody followed by protein A labeled HRP. In input samples, anti-actin antibody was used as a loading control.

H. Analysis of Cellular Proliferation and Apoptosis Following BAL1 Depletion and Dox Treatment Hela cells, which have high levels of endogenous BAL1, were first transfected with control scrambled or BAL1 siRNAs. Thereafter, siRNA-transfected or parental cells were seeded into 96-well plates at 1×10$^4$ cells/well, left untreated or treated with doxorubicin, 50 ng/ml, 200 ng/ml or 400 ng/ml for 1-96 hrs and subsequently evaluated by MTS assay (CellTiter96® Aqueous Non-Radioactive Assay, Promega Corporation, Madison, Wis.). Assays were read at an absorbance of 490 nm using a SpectraMax 190 microplate reader (Molecular Devices, Sunnyvale, Calif.). All assays were performed in triplicate.

In additional studies, parental or BAL1- or control siRNA-treated Hela cells were cultured in the presence or absence of Dox (50 or 200 ng/ml) for 24 hrs. Thereafter, the cells were detached with trypsin, washed with PBS and incubated with anti-Annexin V antibody and PI in 100 µl of binding buffer (10 mM Hepes/NaOH, pH7.4, 140 mM NaCl, 2.5 mM CaCl) for 15 minutes in the dark. Following the addition of 400 µl more binding buffer, the samples were analyzed by flow cytometry (Cytomics FC500, Beckman Coulter, Fullerton, Calif.).

I. Comet Assay

DNA damage was evaluated using the alkaline comet assay according to the manufacturer's instructions (Trevigen). PJ-34-treated and siRNA-transfected cells were IR-treated at dosage of 2 Gys and recovered in normal medium for indicated timepoints before processing. Harvested cells (3×10$^3$) were mixed with 0.8% low melting agarose and layered onto agarose-coated slides. Slides were then submerged into lysis buffer [2.5 M NaCl, 100 mM EDTA, 10 mM Tris (pH 10.0) and 1% Triton X-100] overnight at 4° C. After lysis, slides were incubated for 30 min in electrophoresis buffer (200 mM NaOH and 1 mM EDTA, pH>13). After electrophoresis (25 mins, 21 V, 300 mA), slides were washed with 2× water and 70% ethanol and then air-dried. Slides were stained with 2 µg/ml SYBR Green. Average Comet Tail Moment was scored (50-100 cells/slide) from the confocal images documented on LSM-510 (Carl Zeiss Microimaging) as previously reported in Yan et al. (2009) *Mol. Cell.* 36:110-120. Tail moment (=% DNA in tail*tail Length) was generated by using software TriTek CometScore™

J. Vector Construction, Protein Purification, and Analysis

Oligonucleotides and primers used to generate recombinant GST-tagged BAL1 and FLAG-tagged PARP1 proteins are included in Tables 3 and 4. Using pFLAG-CMV2-BAL1 as template (Takeyama et al. (2003) *J. Biol. Chem.* 278: 21930-21937), BAL1 was PCR-amplified with primers containing Sal I and Not I restriction sites (Table 4). The Sal I- and Not I-digested BAL1 PCR product was then ligated into the vector, pGEX-4T-2 (GE Healthcare Bio-Sciences Corp., Piscataway, N.J.), to generate pGEX-BAL1. Using pGEX-BAL1 as template, the double mutation BAL1 construct (DM) was generated by introducing the IE326,327AA (IE-AA) and D126A mutations into the pGEX-BAL1 vector with the indicated oligonucleotides (Table 3) and the QuikChange Site Directed Mutagenesis Kit (Agilent Technologies). The pGEX-BAL1 recombinant proteins were generated and purified as previously described in Aguiar et al. (2005) *J. Biol. Chem.* 280:33756-33765. Purified BAL1 and PARP1 recombinant proteins were subjected to NuPAGE and analyzed by Coomassie Blue staining Human PARP1 cDNA was purchased from OriGene Technologies (#SC119157).

Using the PARP1 cDNA as a template, FLAG-tagged PARP1 was PCR-amplified with the indicated primers in Table 4. The resulting PCR product was ligated into pET101 following the manufacturer's instructions (Invitrogen). FLAG-tagged PARP1 was purified using the FLAG immunoprecipitation kit according to the manufacturer's instructions (Sigma). Purified PARP1 recombinant proteins were size-fractionated and analyzed by Coomassie Blue staining

TABLE 4

(Oligo and primer sequences are disclosed as SEQ ID NOs: 47-52, respectively, in order of appearance)

| Vector name | Pair of Oligos or primers | Location (bp) |
|---|---|---|
| BBAP-his6 | 5'_caccatggcctcccacctgcgcccgcc gtc_3' | 90-115 |
|  | 5'_ctcaattcctttggctttcagctc_3' | 2312-2285 |
| GST-BAL1* | 5'_acccgGTCGACatggacttttccatgg tggccggag_3' | 104-128 |
|  | 5'_caccGCGGCCGCttaatcaacagggct gccacttg_3' | 2563-2541 |
| FLAG-PARP1** | 5'_caccATGGACTACAAGGATGAC GATGACAAGatggcggagtcttcggataag ctc_3' | 172-295 |
|  | 5'_ttaccacagggaggtcttaaaattg_3' | 3216-3192 |

*The RE sites are capitalized.
**The DNA sequence encoding FLAG tag is capitalized.

K. In Vitro PARP Activity Assay

In vitro poly(ADP-ribose) activity assays were carried out as previously described in Aguiar et al. (2005) *J. Biol. Chem.* 280:33756-33765 with minor modifications. Reactions including ~200 ng of FLAG-tagged PARP1 and 0, 0.5 or 1 mM of NAD+ (Roche Applied Science, Indianapolis, Ind.) substrate were incubated at 25° C. for 30 min in assay buffer (0.1 ml) containing 50 mM Tris-HCl, pH 8.0, 4 mM MgCl$_2$, 0.2 mM dithiothreitol, and 200 ng of activated DNA (Sigma). In certain assays, the PARP inhibitor, PJ-34 (Sigma), was included at 1 mM final concentration. Reactions were stopped by the addition of 20% trichloroacetic acid. Precipitated proteins were rinsed once in 5% trichloroacetic acid, suspended in SDS loading buffer, and fractionated by NuPAGE (Invitrogen). After size fractionation, the proteins were subjected to immunoblotting with anti-PARP1 antibody (mouse monoclonal antibody, BD Biosciences, #51-6639); and anti-PAR (Trevigen, #4335).

L. GST Pulldown

GST-BAL1 or -BAL1 mutant protein (1 µg) was immobilized on glutathione-Sepharose 48 beads and incubated with PARP assay samples (as described above) with or without NAD$^+$ in 1 ml of TBST buffer (20 mM Tris [pH 7.0], 200 mM NaCl, 1% NP-40, 1 mM dithiothreitol [DTT], and 0.5 mM EDTA) for 5 min at 4° C. on a rotating wheel. After 5 washes with TBST buffer, the samples were size-fractionated and immunoblotted with anti-PARP1 (BD Biosciences) and anti-PAR (Trevigen) antibodies.

M. In Vitro Ubiquitylation Assay

For vector construction, the previously described human BBAP cDNA (Ahel et al. (2009) *Science* 325:1240-1243)

was utilized. Using the BBAP cDNA as a template, BBAP was PCR-amplified with the indicated primers in Table 4. The resulting PCR product was ligated into pET101 following the manufacturer's instructions (Invitrogen). His6-tagged BBAP was purified using the Ni-NTA Spin Kit (Qiagen) according to the manufacturer's instructions. Purified BBAP-his6 recombinant protein was size-fractionated, analyzed by Coomassie Blue staining and utilized in the in vitro ubiquitylation assay which was performed as previously described in Ahel et al. (2009) *Science* 325:1240-1243. Using recombinant pET-BBAP-his6 wild type with minor modifications to the method, wild type ubiquitin, lysine 48 (K48)-only ubiquitin and lysine 63 (K63)-only ubiquitin were purchased from Boston Biochem (Cambridge, Mass. 02139). For immunoblotting of specific ubiquitin-chain, anti-ubiquitin-K48 rabbit monoclonal antibody (05-1307) and anti-ubiquitin-K63 rabbit monoclonal antibody (05-1308) were purchased from Millipore.

Example 2

BAL1 and BBAP Recruit to Laser Microirradiation Sites

Although BBAP protects cells exposed to DNA damaging agents (Yan et al. (2009) *Mol. Cell.* 36:110-120), neither BBAP nor its partner protein, BAL1, have been directly associated with a DDR and the function of BAL1 remains undefined. For these reasons, N-terminal GFP-tagged BAL1 and BBAP were expressed in Hela cells and their recruitment to sites of DNA damage induced by laser microirradiation was evaluated. Both GFP-tagged BAL1 and BBAP localized to the laser-induced DNA breaks in less than 1 min with maximum recruitment for ~10 min and subsequent release thereafter (FIGS. 1A-1B). Similar results were obtained when Hela cells were laser microirradiated and immunostained for endogenous BAL1 (FIG. 1C). The macro domain-containing protein rapidly localized to DNA damage sites with peak BAL1 recruitment within several minutes and dispersal within the nuclear compartment in less than 60 min (FIG. 1C). Endogenous BBAP was recruited to sites of laser-induced DNA breaks with similar kinetics (FIG. 1D).

In additional studies, Hela cells were subjected to an alternative source of DNA damage—low-dose irradiation (100 cGy)—and immunostained for BAL1 (FIG. 1E). BAL1 foci were detectable in less than 1 min, were most prominent at 4 min, and decreased in numbers and intensity by 30 min (FIG. 1E). Taken together, these data directly implicate the macro domain-containing BAL1 protein and its partner E3 ligase, BBAP, in the early stages of a DDR.

Example 3

BAL1 Macro Domain 2 is Required for Recruitment to DNA Damage Sites

Figure 2:
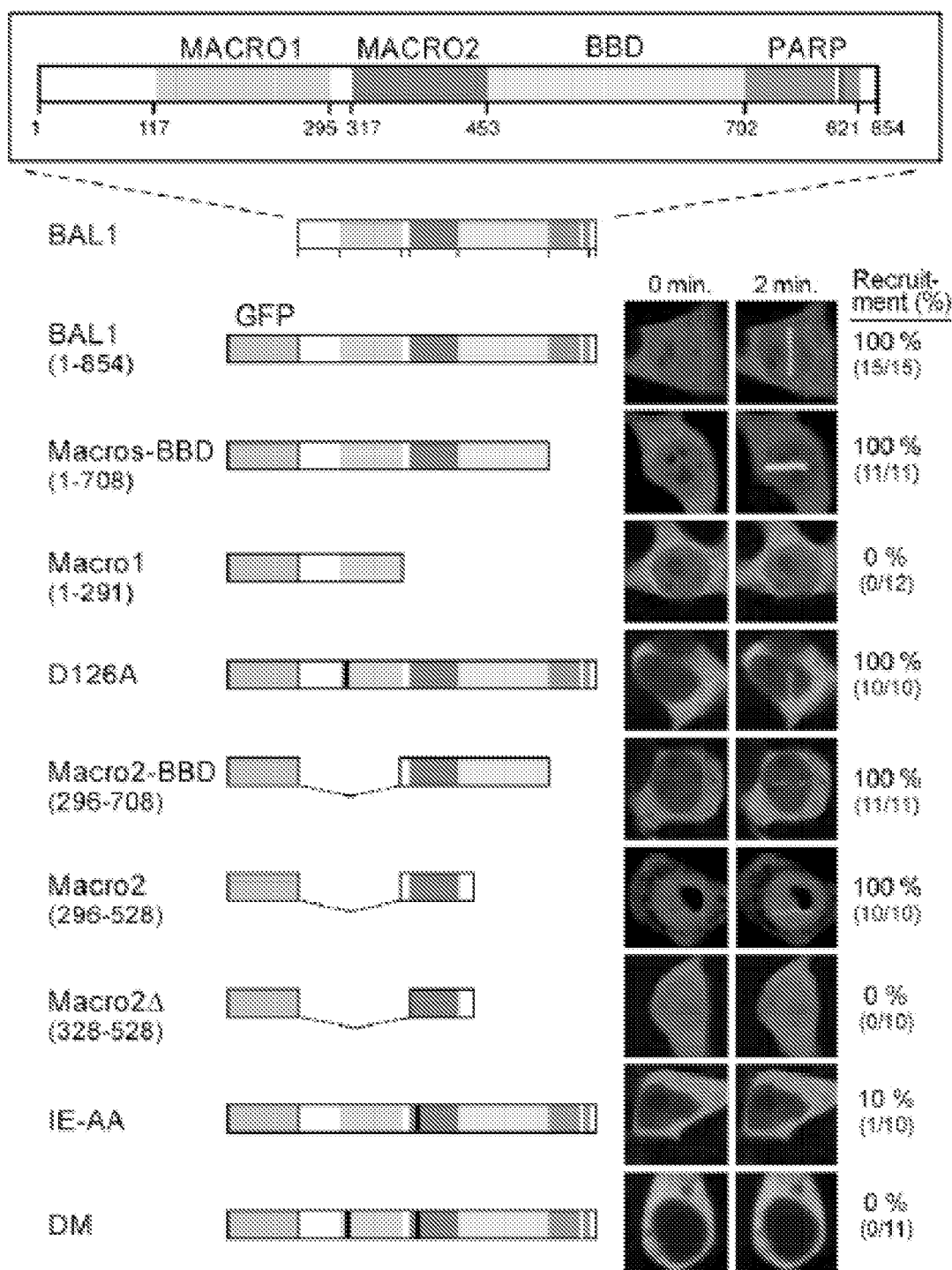
FIG. 2 shows that the BAL1 macro domain 2 is required for recruitment to DNA damage sites. BAL1 protein functional domains, including macro domains 1 and 2), BBAP binding domain (BBD) and the region with partial sequence homology to PARP catalytic domain, are shown in relative order (domain sizes and amino acids positions below). GFP-tagged BAL1 constructs are labeled and represented. Mutations in macro domain 1 (D126A) and macro domain 2 (IE 326, 327 AA [IE-AA]) are also shown in dark black. Representative images of GFP-BAL1 (293T cell) transfectants at baseline and 2 min following laser microirradiation are shown to the right. The percentage of cells with GFP-BAL1 recruitment to laser-induced DNA breaks are shown to the far right.

To assess the role of the BAL1 tandem macro domains in localization to DNA damage sites, we generated a series of GFP-tagged BAL1 constructs that encoded both macro domains (Macro 1 and 2), the respective single macro domains or mutated versions lacking critical residues in one or both macro regions (FIG. 2). The individual GFP-tagged BAL1 constructs were transfected into 293T cells which were subsequently subjected to laser microirradiation and analyzed by confocal microscopy (FIG. 2).

GFP-tagged BAL1 proteins containing both macro domains (BAL1 [1-854], Macros-BBD [1-708]), the complete macro domain 2 (Macro 2-BBD [296-708] or Macro 2 [296-528]) efficiently localized to sites of laser-induced DNA breaks (FIG. 2). In contrast, GFP-tagged BAL1 proteins including a truncated macro domain 2 (Macro 24 [328-528]) or macro domain 1 alone (Macro 1 [1-291]) did not localize to DNA damage sites (FIG. 2). Consistent with these findings, targeted mutation of critical amino acids in macro domain 2 (IE326,327AA [IE-AA]) markedly reduced BAL1 recruitment, whereas a macro domain 1 mutation (D126A) had no effect (FIG. 2). Therefore, BAL1 recruitment to DNA damage sites depends upon its macro domains and macro domain 2 plays a non-redundant and essential role.

Example 4

Figure 3:
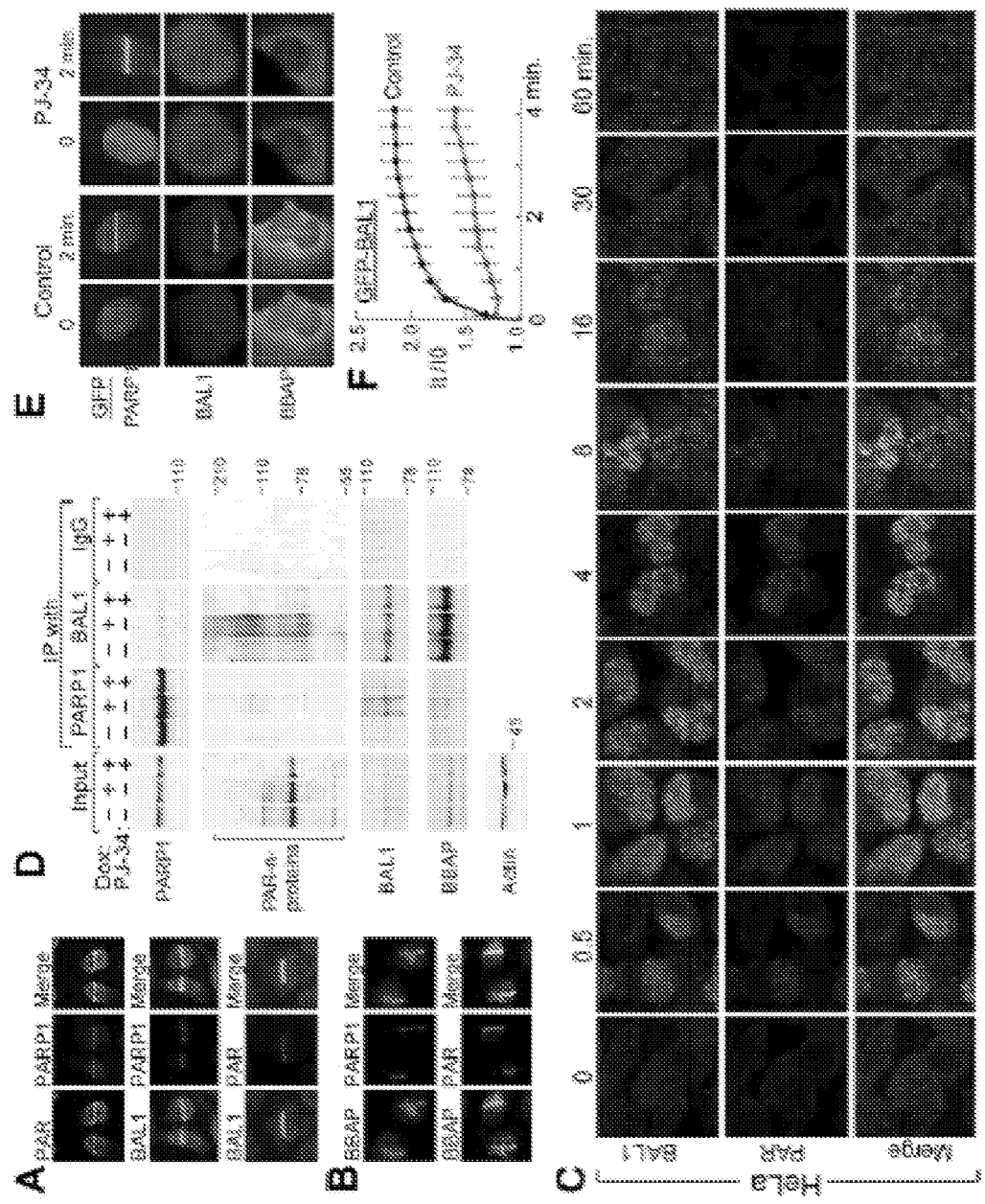
FIGS. 3A-3F show that BAL1 and BBAP co-localize with PARP1 and PAR and physically associate with PAR-n-proteins following DNA damage.

BAL1/BBAP Complex Co-Localizes with PARP1 and PAR and Physically Associates with PAR-n-Proteins Following a DNA Damage Response The kinetics of BAL1 recruitment to DNA damage sites were similar to those reported for PARP1 and its product, PAR (Ahel et al. (2009) *Science* 325:1240-1243 and Timinszky et al. (2009) *Nat. Struct. Mol. Biol.* 16:923-929). It was postulated that BAL1 interacted with PARP1 and/or PAR at sites of DNA damage and analyzed BAL1, PARP1 and PAR recruitment in Hela cells following laser microirradiation (FIG. 3A). PARP1 co-localized with its product, PAR, and with BAL1 in laser-induced DNA breaks (FIG. 3A). In addition, BBAP co-localized with PARP1 and PAR in DNA damage sites (FIG. 3B). Hela cells were also subjected to low-dose irradiation and early co-localization of BAL1 and PAR repair foci was observed (FIG. 3C).

The interactions between these proteins and protein modifications were subsequently assessed by immunoprecipitation. To define the basis of PARP1 interactions in these studies, the drug, PJ-34, which inhibits PARP1 generation of PAR but leaves PARP1 DNA binding intact, was used (Timinszky et al. (2009) *Nat. Struct. Mol. Biol.* 16:923-929). Hela cells were untreated or treated with low-dose Dox (50 mg) for 10 min with or without PJ-34 pretreatment. Thereafter, whole cell lysates were prepared and PARP1, BAL1 (and control IgG) were immunoprecipitated and immunoblotted for PARP1, PAR-n-proteins, BAL1 and BBAP (FIG. 3D). Input whole cell lysates were similarly analyzed (FIG. 3D, left panel).

Figure 4:
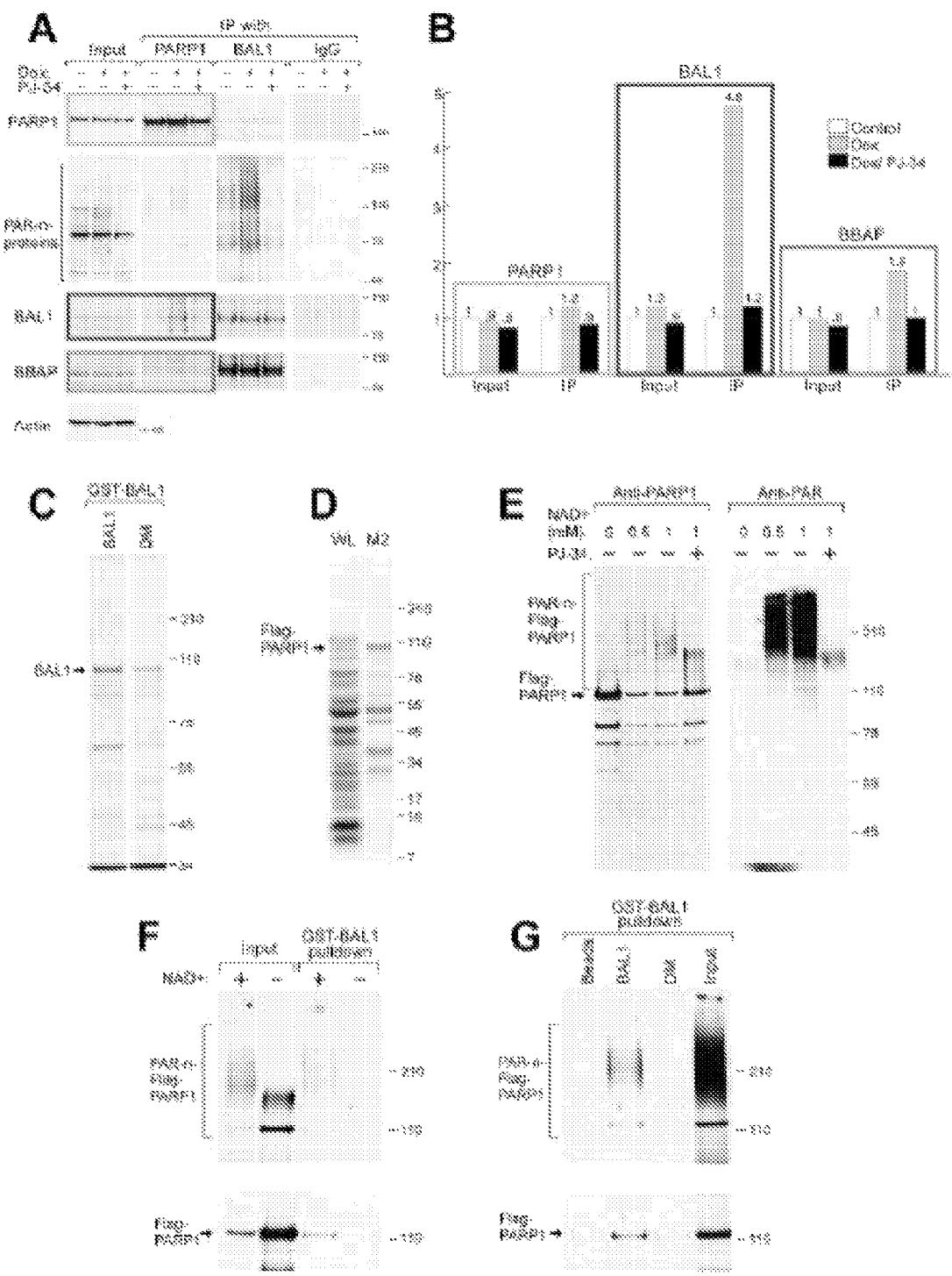
FIGS. 4A-4G show analyses of co-immunoprecipitated PARP1, BAL1 and BBAP and the interaction between GST-BAL1 and PAR.

As expected, input lysates from Dox-treated cells had a modest increase in PAR formation, which was abrogated by PJ-34 (FIG. 3D, left panel). PARP1 immune complexes from Dox-treated cells contained more abundant PAR-n-proteins in addition to increased BAL1 and BBAP and PJ-34 inhibited these interactions (FIGS. 3D, 4A, and 4B). Following Dox treatment, BAL1 immune complexes also included increased PAR-n-proteins unless PARP activity was inhibited by PJ-34 (FIG. 3D). These data indicate that BAL1 binds PAR-n-proteins, which are more abundant following DNA damage and PARP1 activation.

To distinguish between BAL1 binding to PAR-modified proteins, including PARP1, or PARP1 itself, in vitro pull-down assays were performed using GST-tagged BAL1 proteins and FLAG-tagged PARP1 (FIGS. 4C-4D). It was first demonstrated that FLAG-tagged PARP1 was functionally active in vitro, catalyzing the synthesis of PARP1-associated PAR chains in the presence of NAD+ (FIG. 4E). GST-tagged BAL1 selectively pulled down PAR-modified PARP1 in a macro domain-dependent manner, but did not bind unmodified PARP1 protein (FIGS. 4F-4G), confirming that BAL1 specifically binds to PAR.

Example 5

Recruitment of BAL1/BBAP to DNA Damage Sites is Dependent Upon PARP Activity

Given the interaction between BAL1 and PAR-n-proteins (FIGS. 3D and 4), it was next asked whether PARP1 activity was required for BAL1 and BBAP recruitment to DNA damage sites. GFP-tagged PARP1, BAL1 or BBAP were expressed in Hela cells and the cells were treated with PJ-34 or vehicle alone prior to laser microirradiation. As expected, PJ-34 did not impair GFP-PARP1 binding to laser-induced DNA breaks (FIG. 3E). However, PJ-34 pretreatment inhibited the recruitment of GFP-tagged BAL1 and BBAP to DNA damage sites (FIGS. 3E-3F).

Figure 5:
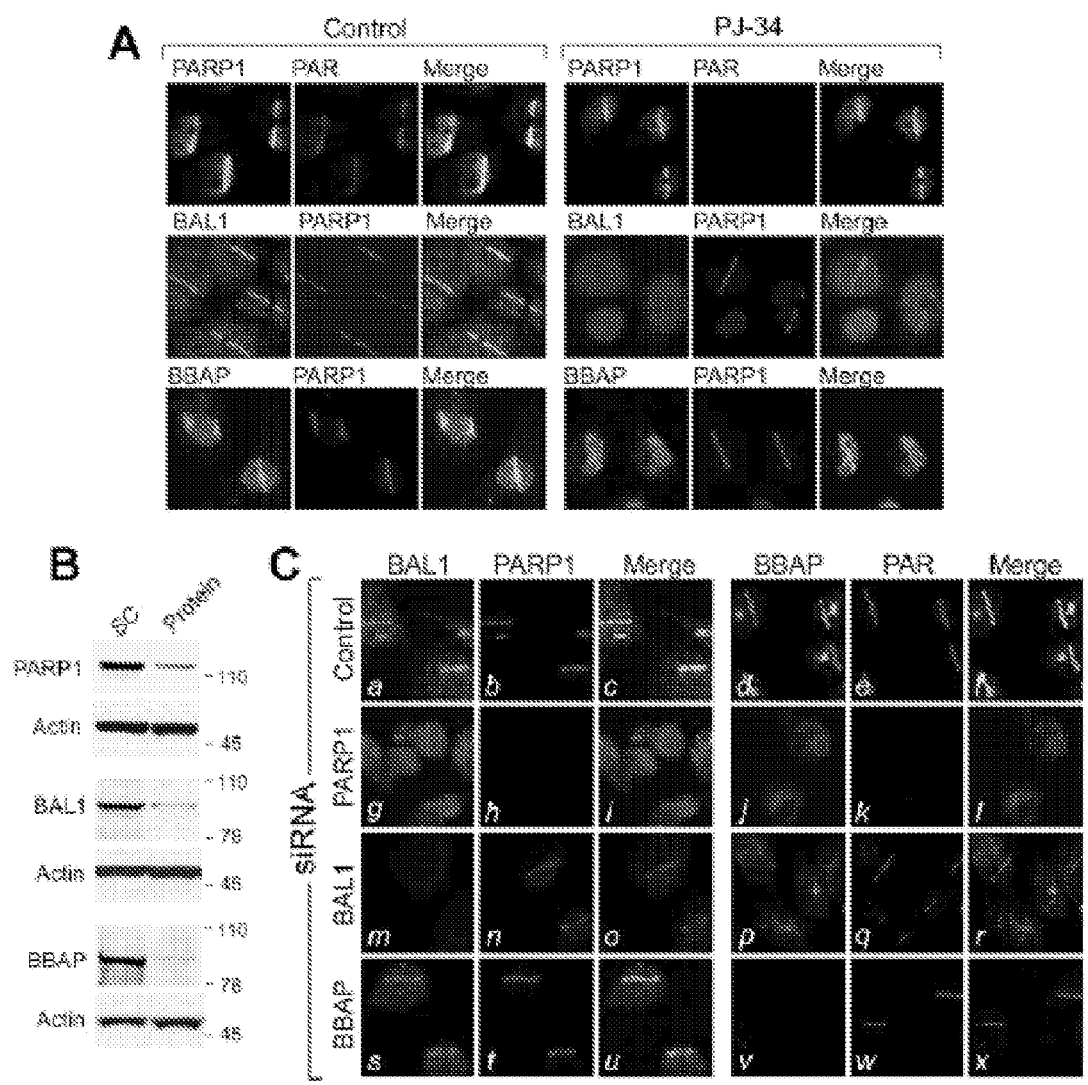
FIGS. 5A-5C show recruitment of endogenous PARP1, PAR, BAL1 and BBAP to DNA damage sites.
Figure 6:
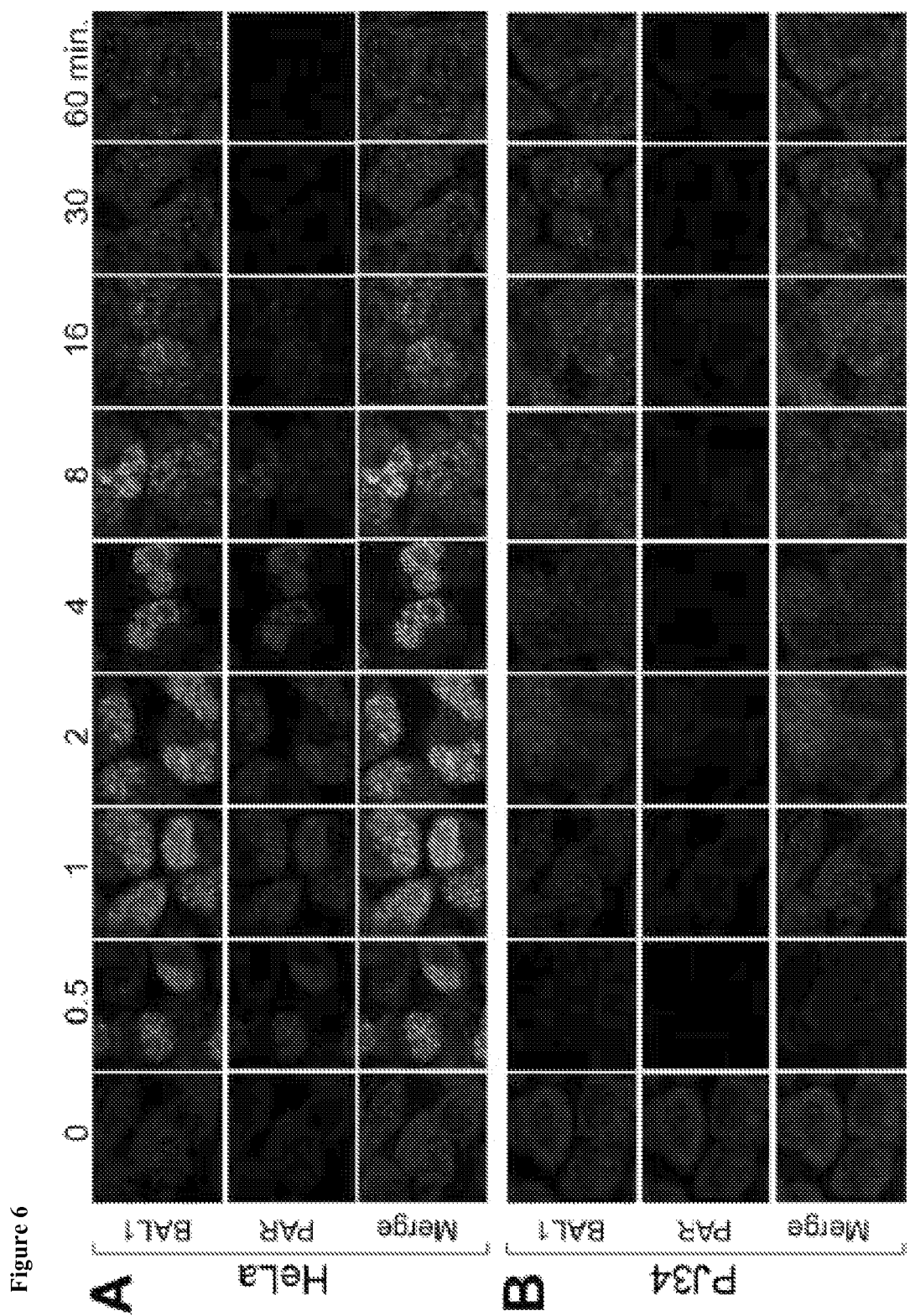
FIGS. 6A-6B show co-localization of BAL1 and PAR foci in γ-irradiated control Hela cells (FIG. 6A), and Hela cells pretreated with PJ-34 (FIG. 6B). Hela cells were treated with low-dose irradiation (100 cGy) and analyzed for BAL1 and PAR foci at baseline and at serial timepoints (0.5-60 min) thereafter. BAL1 is shown at the top; PAR is shown in the middle; and merged images are shown at the bottom.

Similar results were obtained when Hela cells were pre-incubated with PJ-34 or vehicle alone, laser microirradiated and immunostained for endogenous PARP1, PAR, BAL1 or BBAP (FIG. 5A). Although PJ-34 did not alter PARP1 recruitment to DNA damage sites, the compound eliminated PARP-mediated PAR formation (FIG. 5A, top panel) and abrogated BAL1 and BBAP recruitment to laser-induced DNA breaks (FIG. 5A, middle and bottom panels). PJ-34 treatment also inhibited irradiation-induced PAR and BAL foci formation in Hela cells (FIGS. 6A-6B). Taken together, these data indicate that PARP activity and PAR formation are required for BAL1 and BBAP localization to DNA damage sites.

To define the hierarchy of PARP1, BAL1 and BBAP interactions, each protein was individually depleted by siRNA and subsequent DNA damage response was assessed (FIGS. 5B-5C). PARP1 was a focus because over 85% of in vivo PARP activity is attributed to this family member (Yelamos et al. (2006) *EMBO* 1 25:4350-4360). PARP1 depletion (FIG. 5C, panels g-l) abrogated DNA-damaged induced PARP1 localization (panel h) and PARP-mediated PAR formation (panel k). In addition, PARP1 knockdown inhibited BAL1 and BBAP recruitment to laser-induced DNA breaks (FIG. 5C, panels g and j, respectively). In BAL1 or BBAP-depleted cells, activated PARP1 and PAR were still recruited to DNA-damage sites, confirming that PARP1 functions upstream of BAL1 and BBAP (FIG. 5C, panels n, q; and t, w, respectively). In BAL1-depleted cells, BBAP did not accumulate in laser-induced DNA breaks (FIG. 5C, panel p). In contrast, BAL1 localized to DNA damage sites in BBAP-depleted cells (FIG. 5C, panel s), placing BAL1 upstream of BBAP. Therefore, BAL1 is recruited to a DNA damage site via PARP1-mediated PAR formation and BBAP localizes to the site via its interaction with BAL1.

Example 6

BAL1 Limits the Cellular Response to DNA-Damaging Agents

The function of BAL1 in tumor (Hela) cell growth and (Dox)-induced cytotoxicity was next assessed by depleting endogenous BAL1 via siRNA and treating the cells with Dox (50-200 ng). Although BAL1 RNAi reduced the growth of untreated cells, the consequences of BAL1 depletion were most striking in cells treated with low-dose Dox (50 ng) (FIG. 7A). For example, after 72 hr of treatment with low-dose Dox (50 ng), cellular proliferation was ~80% lower in BAL1-depleted cells than in control RNAi or parental cells (FIG. 5A, $p<0.01$). BAL1 depletion also increased cellular apoptosis in both untreated and Dox-treated cells (FIG. 7B). These data indicate that the macro domain-containing BAL1 protein enhances tumor cell survival and decreases Dox-induced cytotoxicity.

To directly evaluate the role of PARP-dependent BAL1 recruitment on tumor cell viability, we depleted BAL1 by siRNA and depleted with GFP vector only, GFP-BAL1 or GFP-BAL1DM (which lacks the PAR binding domain; see FIG. 2). In BAL1-depleted cells, BAL1 recruitment to PARP-1 associated laser-induced DNA breaks was restored by GFP-BAL1 but not by GFP-BAL1DM (FIG. 7C; panels b vs. c, h vs. i). GFP-BAL1 repletion also limited the apoptosis of BAL1-depleted cells at baseline and following Dox treatment, unlike GFP-BAL1DM (FIG. 7D). These data directly and specifically associate the early macro domain- and PAR-dependent recruitment of BAL1 to DNA damage sites (FIG. 7C) with enhanced tumor cell survival (FIG. 7D).

In some embodiments, a skilled artisan can perform similar experiments using a variety of cancer therapies, including PARP inhibitors (e.g., inhibitors of PARP-1). It is believed that BAL1 limits the cellular response to PARP inhibitors (e.g., inhibitors of PARP-1).

Example 7

Figure 8:
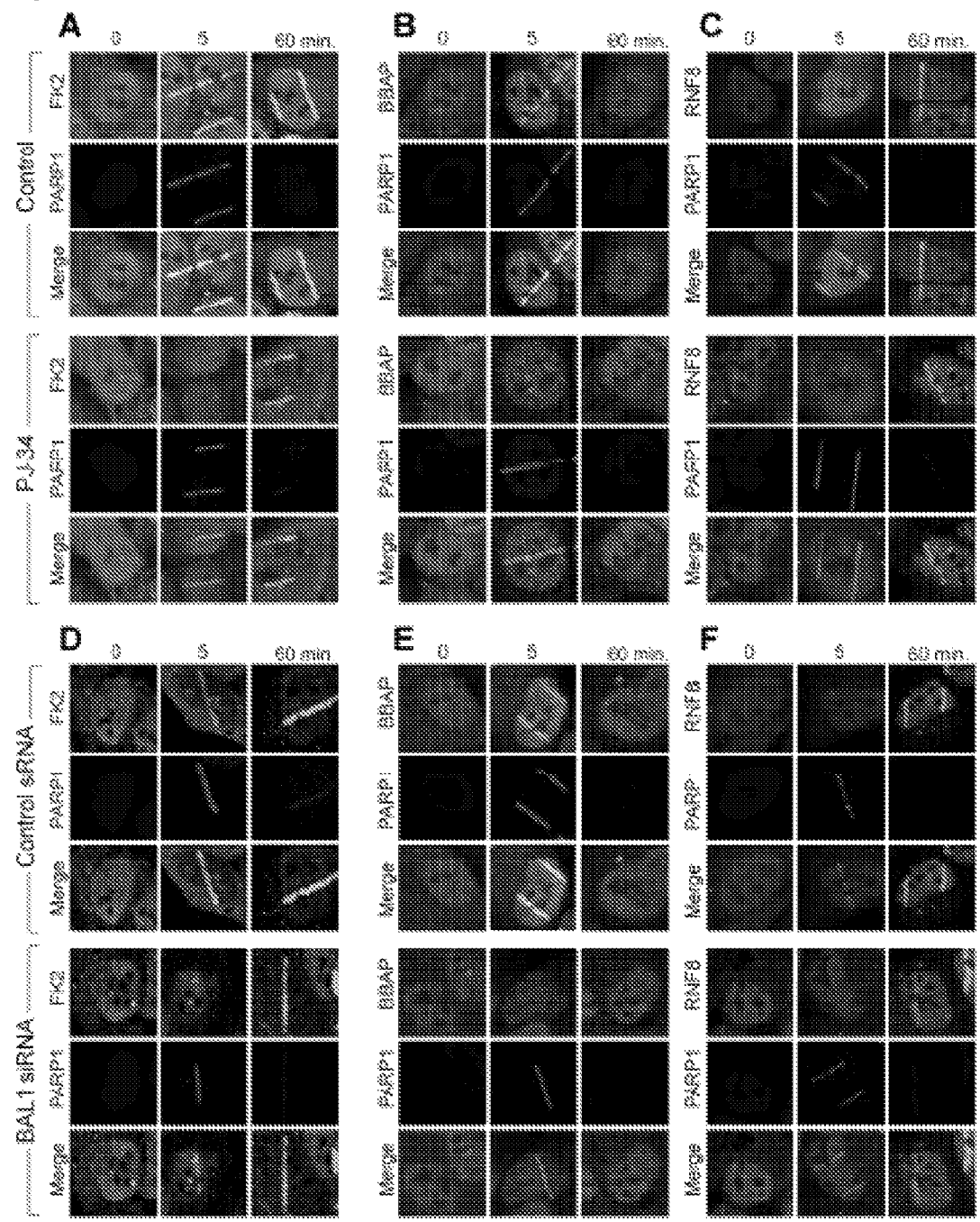
FIGS. 8A-8F show that PARP-dependent recruitment of BBAP to DNA damage sites is required for early ubiquitin chain formation. Ubiquitylation (conjugated ubiquitin, FK2 immunostaining) and PARP1 (FIG. 8A), BBAP (FIG. 8B) and RNF8 (FIG. 8C) recruitment to laser-induced DNA breaks in control or PJ-34 pre-treated cells (0, 5 and 60 min following DNA damage). FK2 immunostaining and PARP1 (FIG. 8D), BBAP (FIG. 8E) and RNF8 (FIG. 8F) in control siRNA or BAL siRNA cells at the same timepoints following laser microirradiation.
Figure 9:
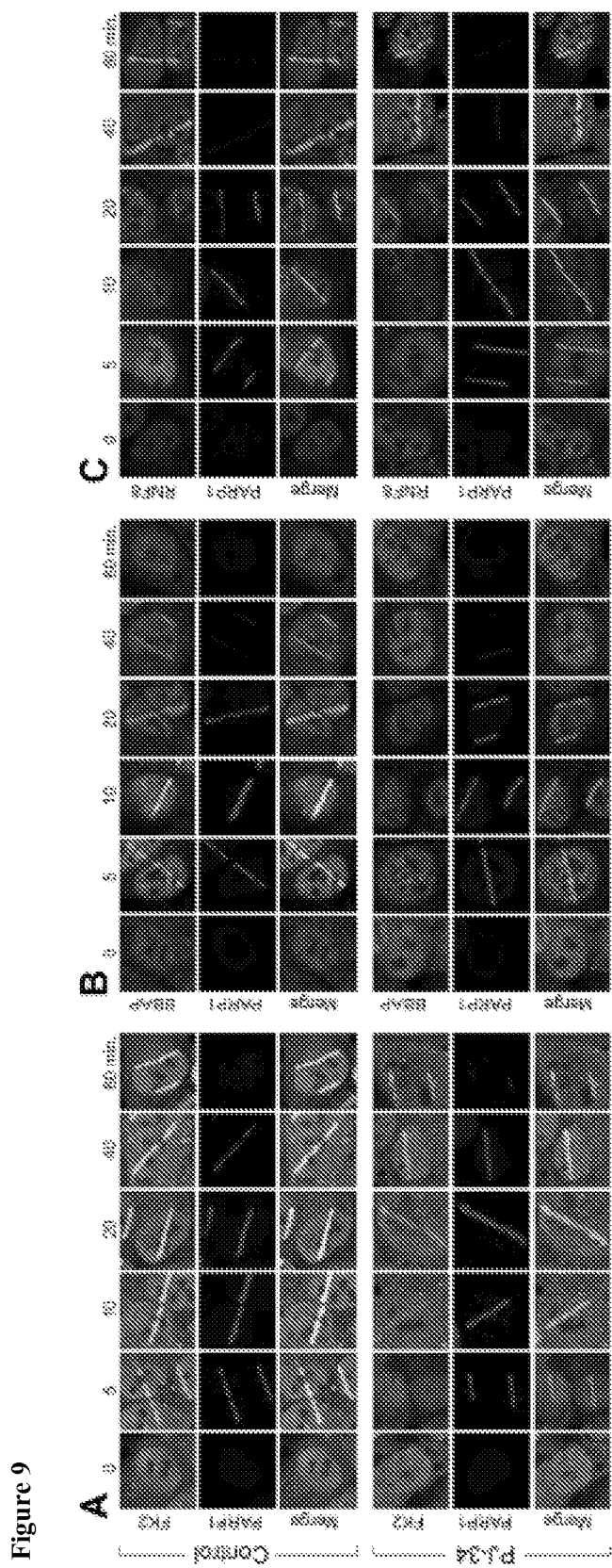
FIGS. 9A-9C show the kinetics of ubiquitylation and BBAP, RNF8 and PARP1 recruitment to laser-induced breaks.

Early Ubiquitin Chain Formation at DNA Damage Sites Requires PARP1, BAL1 and BBAP After demonstrating the functional significance of BAL1 recruitment to PARylated DNA damage sites (FIG. 7), it was assessed whether a potential link between PARP1 activation, localization of BAL1 partner E3 ligase, BBAP, and conjugated ubiquitin chain formation existed. Hela cells were pre-treated with PJ-34 or vehicle alone, laser microirradiated and immunostained for PARP1, BBAP and newly formed ubiquitin chains (using the FK2 antibody which recognizes conjugated ubiquitin) (FIGS. 8A, 8B, and 9). FK2 immunostaining was readily apparent from the earliest analyzed timepoint (5 min) through the last assessment (60 min) (FIGS. 8A and 9). Although PJ-34 did not impair PARP1 recruitment to DNA damage sites, the PARP inhibitor abrogated BBAP localization and early ubiquitin chain formation (FK2 immunostaining) (FIGS. 8A, 8B, 9A, and 9B). BAL1 depletion similarly decreased BBAP recruitment and early ubiquitin chain formation at laser-induced DNA breaks (FIGS. 8D-8E). Depletion of endogenous PARP1 or BBAP prior to laser microirradiation also decreased early FK2 immunostaining. The effects of chemical PARP inhibition or BAL1 depletion on ubiquitin chain formation were most striking in the first few minutes following laser microirradiation (FIGS. 8A, 8D, and 9). Taken together, these data indicate that early ubiquitin chain formation at DNA damage sites is dependent upon PARP1 activity, BAL/BBAP recruitment and the BBAP E3 ligase.

Example 8

PARP1 Activation and BAL1/BBAP Recruitment to DNA Damage Sites are Independent of ATM and MDC1

Given the recently described ATM/MDC1-dependent ubiquitylation at DNA damage sites (Doil et al. (2009) *Cell*

Figure 10:
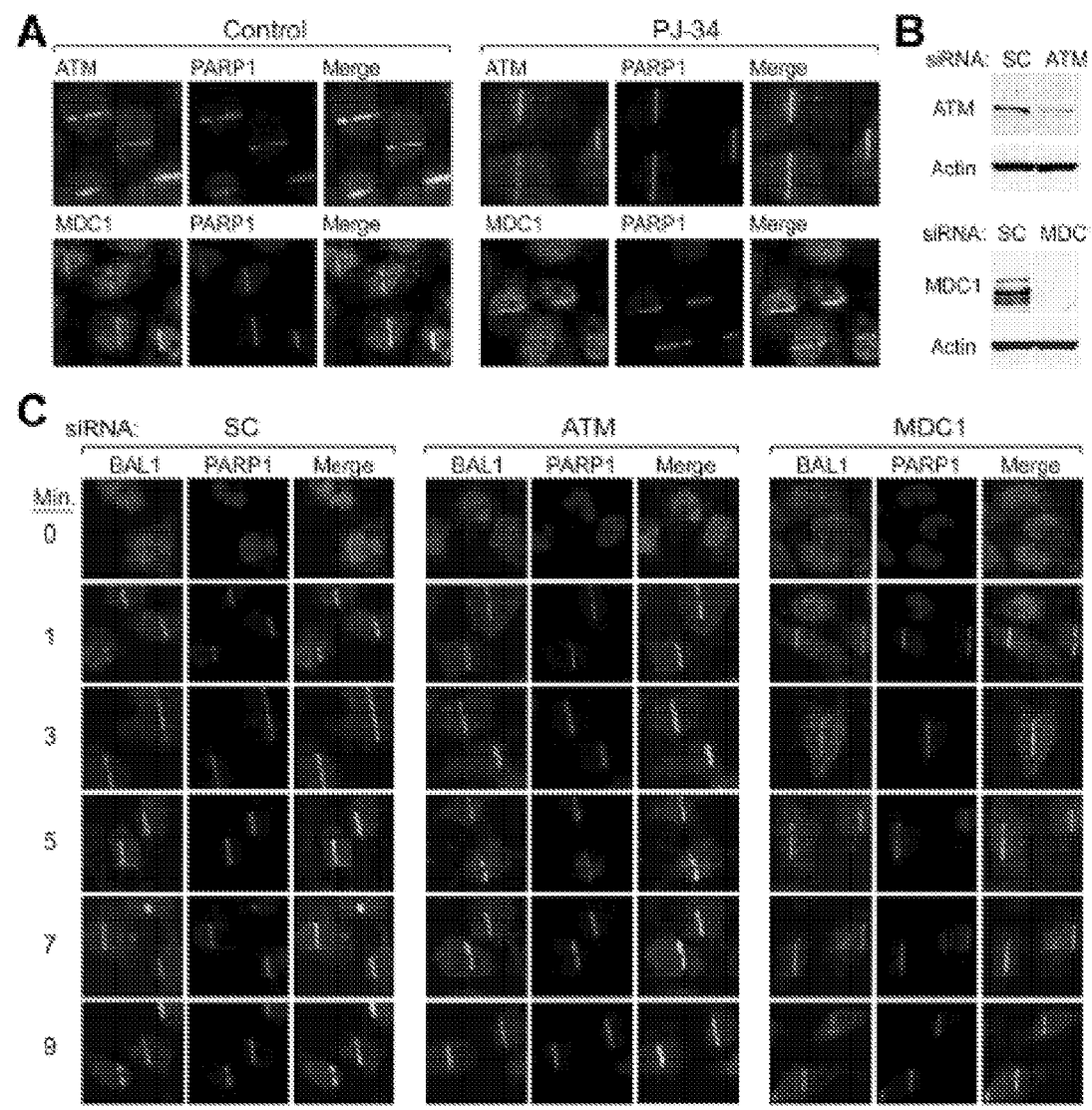
FIGS. 10A-10C show that PARP1 activation and BAL1/BBAP recruitment to DNA damage sites are independent of ATM and MDC1.

136:435-446 and Mailand et al. (2007) *Cell* 131:887-900), the relationship between ATM and MDC1 accumulation and PARP1 activation at laser-induced DNA breaks was assessed. Hela cells were pre-incubated with PJ-34 or vehicle alone, laser microirradiated and immunostained for endogenous ATM, MDC1 and PARP1 (FIG. 10). The chemical PARP inhibitor did not impair ATM or MDC1 recruitment to DNA damage sites (FIG. 10A). In complementary experiments, depletion of ATM or MDC1 by siRNA (FIG. 10B) had no effect on PARP1 or BAL1 accumulation at laser-induced DNA breaks (FIG. 10C). Therefore, PARP1 activation and BAL1 recruitment are independent of ATM and MDC1 suggesting that there are two separately regulated pathways of DNA damage-induced ubiquitylation. Consistent with this hypothesis, neither chemical PARP inhibition nor BAL1 depletion altered the delayed kinetics of accumulation of the ATM/MDC-1 dependent E3 ligase, RNF8, at DNA damage sites (FIGS. 8C and 9C). RNF8 was primarily detectable 40-60 min following laser microirradiation (FIGS. 8C, 8F, and 9C), in contrast to BBAP which was seen from the earliest evaluated timepoint, 5 min, through 20-40 min (FIGS. 8B, 8E, and 9B).

Example 9

Functional Analyses of PARP1/BAL1/BBAP- and MDC1/RNF8-Associated DDRs

The functional consequences of the respective PARP1/PAR-dependent BAL1/BBAP and ATM/MDC1/RNF8 DDR pathways were compared using comet assays, which measure unrepaired DNA damage in individual cells with gel electrophoresis (Olive and Banath (2006) *Nat. Protocol.* 1:23-29). In initial studies, Hela cells were pre-treated with PJ-34 or vehicle alone, subjected to low-dose irradiation (200 cGy) and analyzed by comet assay 15 min, 60 min or 24 hrs thereafter (FIG. 11A). In control cells, the intensity of the comet tails, which reflect unrepaired DNA damage, was modestly increased at 15 min, decreased at 60 min and then neared baseline by 24 hrs (FIG. 11A, left panel). In PJ-34 treated cells, comet tail intensity was markedly increased at 15 min and persistently elevated through 24 hrs (FIG. 11A, right panel). BAL1- and BBAP-depleted cells had similarly increased comet tail intensity 15 min through 24 hr following irradiation (FIGS. 11B and 11D, left and middle panels). Therefore, chemical PARP inhibition and BAL1 or BBAP depletion all markedly increase unrepaired DNA damage at early and later timepoints (FIGS. 11A, 11B, and 11D).

The apparent independence of PARP1/BAL1/BBAP and ATM/MDC1/RNF8 recruitment and ubiquitylation at DNA damage sites (FIGS. 8-10) prompted a comparison of these pathways using the comet assay. In contrast to BAL1-depleted cells, MDC1-knockdown cells had a more delayed pattern of unrepaired DNA damage (comet tail intensity) following irradiation (FIG. 11B). When BAL1 and MDC1 were both depleted prior to irradiation, comet tail intensity was greater than that of either single knockdown at 15 min through 24 hr (FIG. 11B, right panel).

DNA damage was also more delayed in RNF8-depleted cells than in BBAP-knockdown cells (FIGS. 11C-11D). When both E3 ligases, BBAP and RNF8, were depleted prior to irradiation, comet tail intensity was greater than that of either single knockdown from early through later timepoints (FIG. 11D). Taken together, these data indicate that PARP1-dependent BAL1/BBAP-mediated DNA damage repair is functionally distinct and non-redundant to that of ATM/MDC1/RNF8.

Example 10

Early 53BP1 Recruitment to DNA Damage Sites Requires PARP1, BAL1 and BBAP

Figure 12:
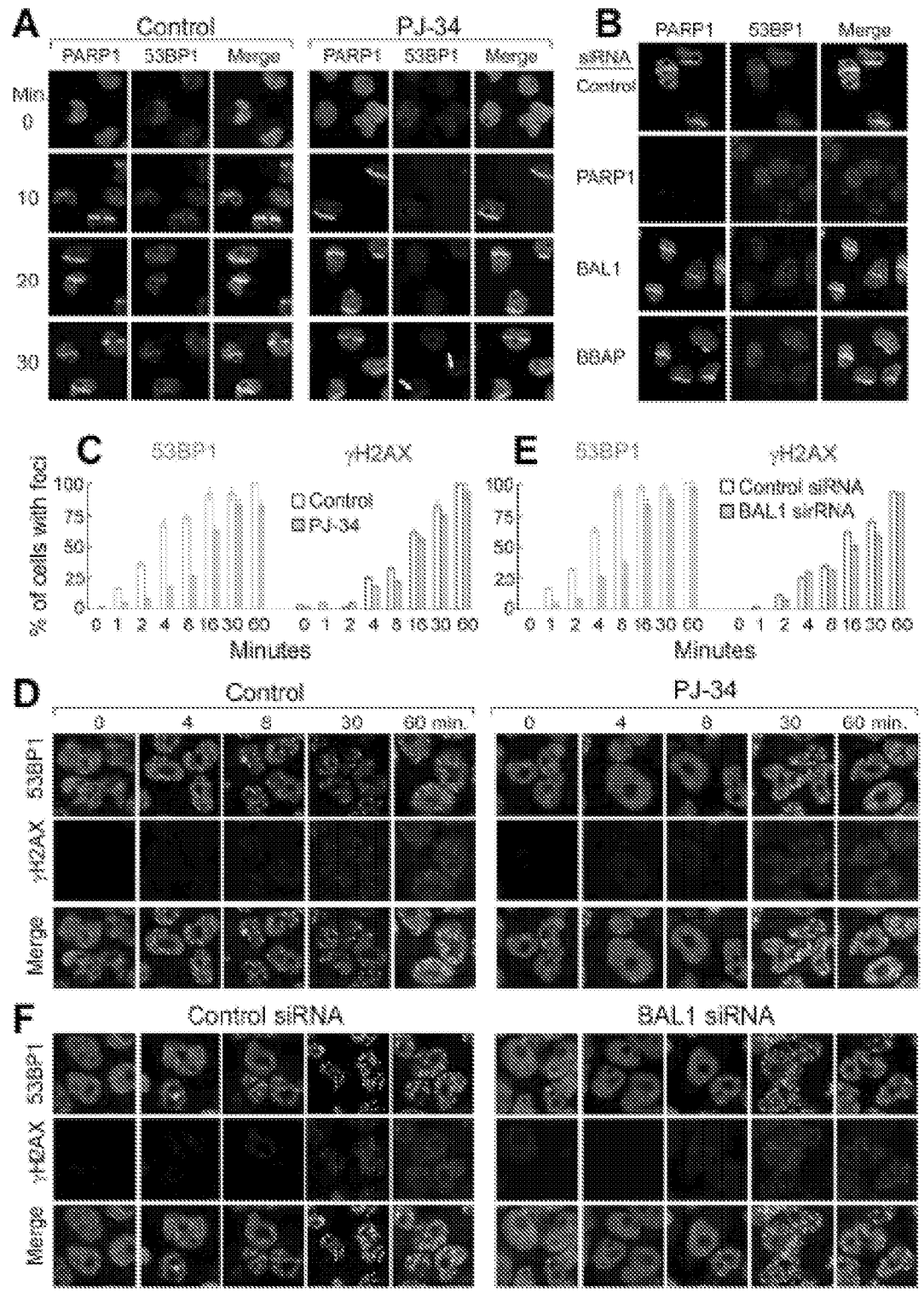
FIGS. 12A-12F show that early 53BP1 recruitment to DNA damage sites requires PARP1, 854 BAL1 and BBAP.

It was previously found that depletion of the BBAP E3 ligase delayed the accumulation of the checkpoint mediator, 53BP1, in repair foci ((Yan et al. (2009) *Mol. Cell.* 36:110-120). Given the dependence of BBAP on PARP1 activation and BAL1 recruitment, the consequences of chemical PARP1 inhibition (PJ-34 treatment) on 53BP1 accumulation at DNA damage sites were assessed (FIG. 12A). In PJ-34 treated cells, 53BP1 localization to laser-induced DNA breaks was significantly delayed (FIG. 12A). Similar results were obtained when endogenous PARP1, BAL1 or BBAP were depleted by siRNA prior to laser microirradiation (FIG. 12B; images obtained ~20 min. following microirradiation). These data directly implicate PARP1 activation and BAL1/BBAP recruitment in the early localization of 53BP1 to DNA damage sites.

To further characterize potentially separate PARP1- and ATM/MDC1/RNF8/H2AX-dependent pathways of 53BP1 accumulation, Hela cells were pre-treated with PJ34 or vehicle alone, subjected to low-dose irradiation and analyzed for 53BP1 and H2AX foci at 0-60 min thereafter. At the earliest timepoints following irradiation (<30 min), there were significantly more 53BP1 foci in control cells than in PJ34-treated cells (p=0.004; FIGS. 12C-12D). In contrast, H2AX foci formation was more delayed than that of 53BP1 and unaffected by treatment with PJ-34 (p=NS; FIGS. 12C-12D). After irradiation, 53BP1 foci formation was also more rapid in control cells than in BAL1-depleted cells (p=0.001; FIGS. 12E-12F). However, H2AX foci formation was more delayed and similar in control and BAL knockdown cells (p=NS; FIGS. 12E-12F). These data define the initial PARP1- and BAL1-dependent, H2AX-independent recruitment of 53BP1 to DNA damage sites.

Example 11

Early RAP80 and BRCA1 Localization to DNA Damage Sites Requires PARP1, BAL1 and BBAP BRCA1 accumulates at DNA damage sites via the adaptor protein, RAP80, and its ubiquitin-interacting motifs. For these reasons, we also analyzed the kinetics of BRCA1 and RAP80 accumulation at laser-induced DNA breaks following chemical PARP inhibition. In PJ-34 treated cells, RAP80 and BRCA1 recruitment to DNA damage sites were markedly delayed (FIGS. 13A-13B).

Figure 15:
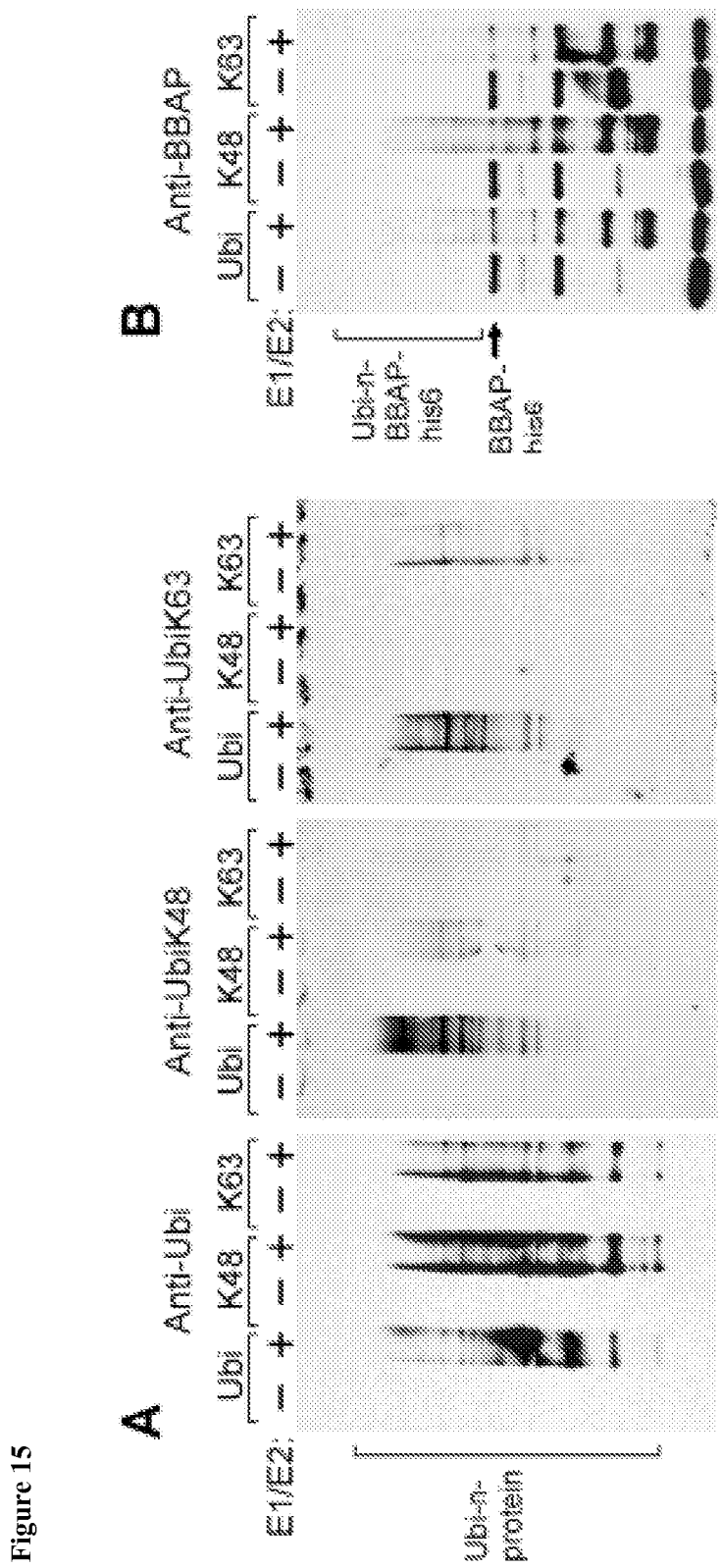
FIGS. 15A-15B show in vitro analysis of BBAP ubiquitylation using lysine-specific ubiquitin. BBAPhis6 was purified from E. coli. and was incubated with or without E1/E2 ligase and wild-type ubiquitin, K48-only ubiquitin, or K63-only ubiquitin. Thereafter, samples were size-fractionated and immunoblotted with the following antibodies: anti-ubiquitin, anti-ubiK48, anti-ubiK63 (FIG. 15A) and anti-BBAP (FIG. 15B).

RAP80 and BRCA1 localization to DNA damage sites were also delayed in BAL1-depleted cells (FIGS. 14A-14D). Furthermore, PARP1, BAL1 or BBAP knockdown all reduced early RAP80 and BRCA localization to laser-induced DNA breaks (FIG. 13C; PARP1, panels h and k; BAL1, panels n and q; and BBAP, panels t and w, respectively). Consistent with these findings, BBAP ubiquitylated the RAP80 residue, K63 (Lok et al. (2012) *Nuc. Acids Res.* 40:196-205), in addition to K48 (FIG. 15).

Figure 13:
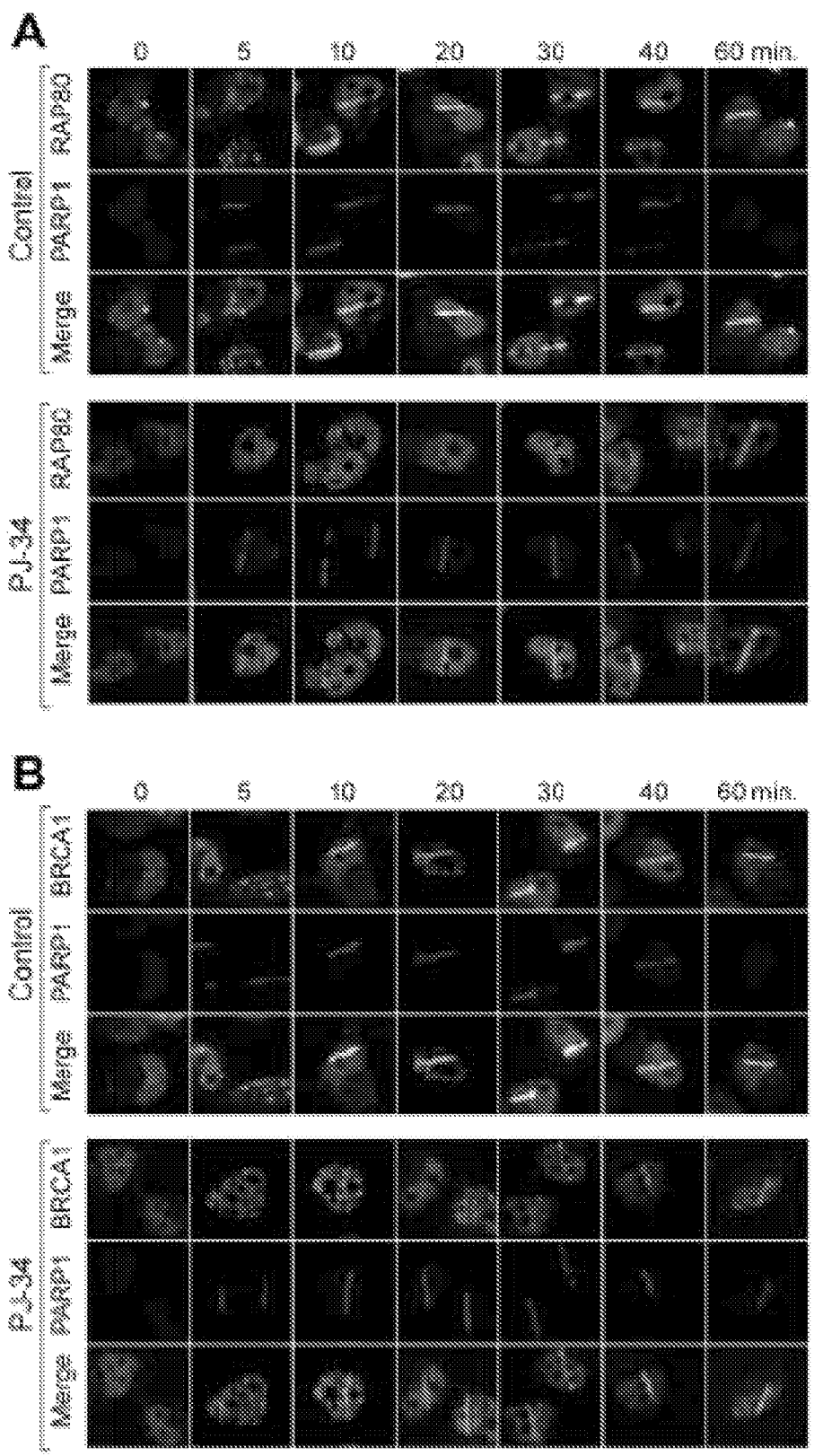
FIGS. 13A-13D show that early RAP80/BRCA1 recruitment to DNA damage sites requires PARP1, BAL1 and BBAP. PARP1, RAP80 (FIG. 13A) and BRCA1 (FIG. 13B) recruitment to laser-induced breaks in control or PJ-34 treated cells (0-60 min following laser microirradiation). RAP80 (FIG. 13A) or BRCA1 (FIG. 13B) is shown at the top; PARP1 is shown in the middle; and merged images are shown at the bottom.
Figure 13:
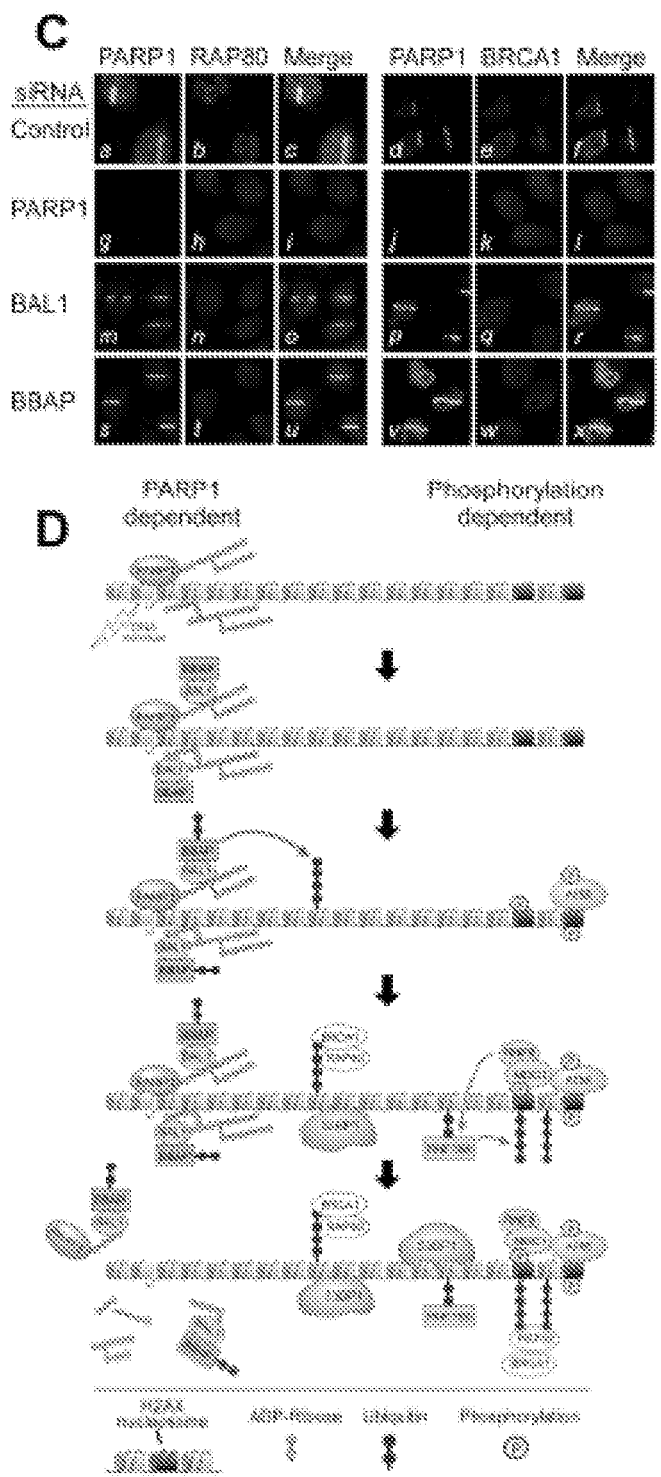
Figure 14:
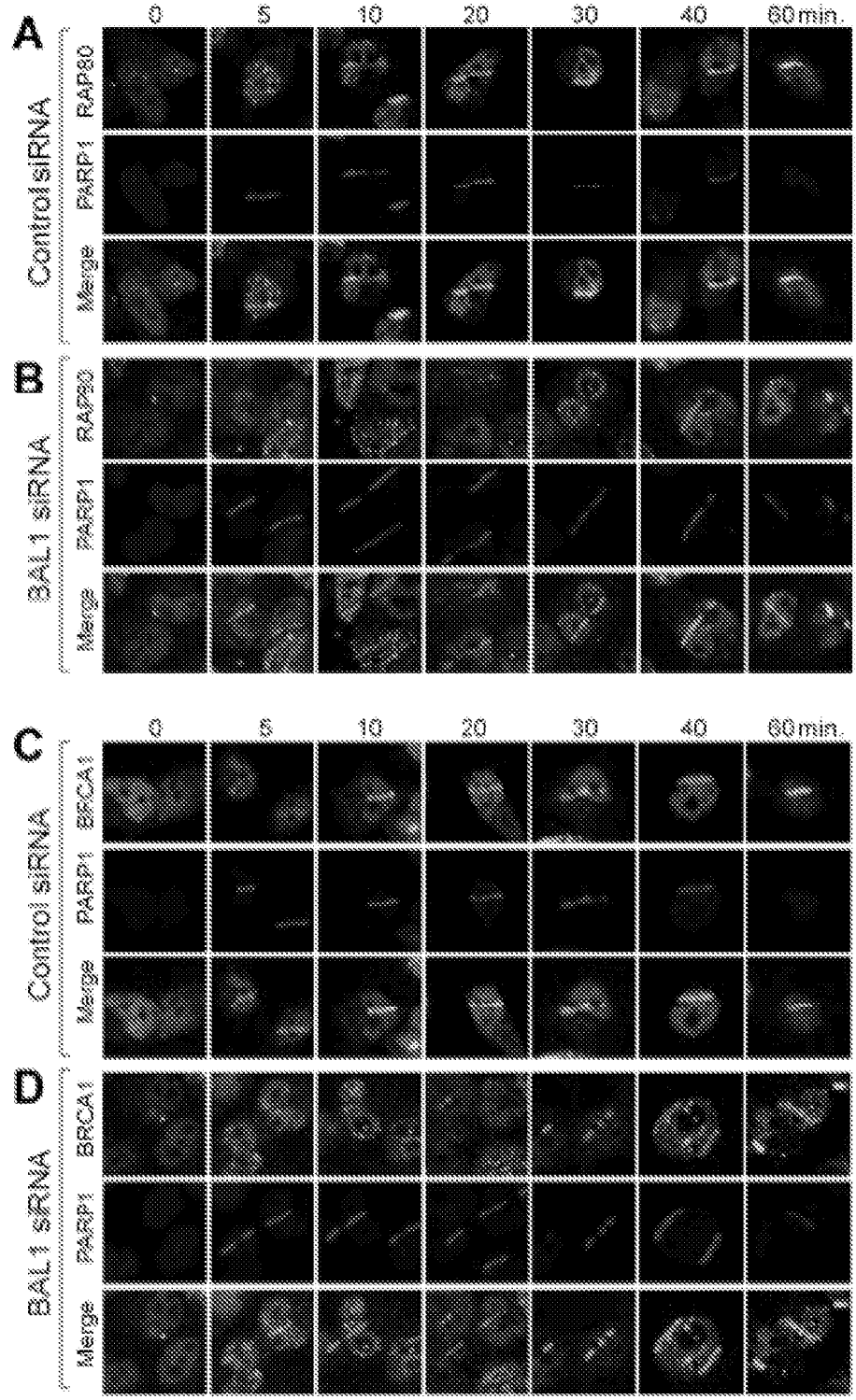

Taken together, these data indicate that PARP1-, BAL1 and BBAP-dependent ubiquitylation provides initial access to the downstream mediators, RAP80 and BRCA1, at DNA damage sites (FIG. 13D). These studies define separate temporally and functionally distinct mechanisms of DNA-damage induced ubiquitylation and recruitment of 53BP1 and BRCA1—an early PARP1, BAL1 and BBAP-dependent pathway and a later phosphorylation-dependent, ATM/MDC1/RNF8-associated route (FIG. 13D).

More generally, a direct link between the initial rapid and short-lived PARylation at DNA damage sites, PAR-dependent recruitment of the BAL1 macro domain-containing protein and its partner E3 ligase, BBAP, and BBAP-mediated ubiquitylation and localization of the checkpoint mediators, 53BP1 and BRCA1 has been defined herein. The PARP1-dependent localization of BAL1 and BBAP functionally limits early and delayed DNA damage and enhances cellular viability independent of ATM/MDC1/RNF8. These data firmly establish BAL and BBAP as bona fide DDR pathway members and provide new insights into PARP-mediated DNA repair.

The kinetics of BAL1 and BBAP recruitment to laser-induced breaks reflect their early PAR-dependent localization at these sites. These findings provide a mechanistic basis for the previously described delay in 53BP1 foci formation in BBAP-depleted cells (Yan et al. (2009) Mol. Cell. 36:110-120). In the earlier studies, BBAP knockdown selectively decreased 53BP1 recruitment at early timepoints following low-dose doxorubicin (50 ng) or γ-irradiation (100 cGy)-induced DNA damage; however, at later timepoints, the numbers of 53BP1 repair foci were similar in BBAP-depleted cells and controls (Yan et al. (2009) Mol. Cell. 36:110-120). The findings likely reflect selective impairment of early PAR-dependent, BAL1/BBAP-mediated 53BP1 recruitment with intact delayed ATM/MDC1/RNF8-dependent events (FIG. 13D).

Figure 7:
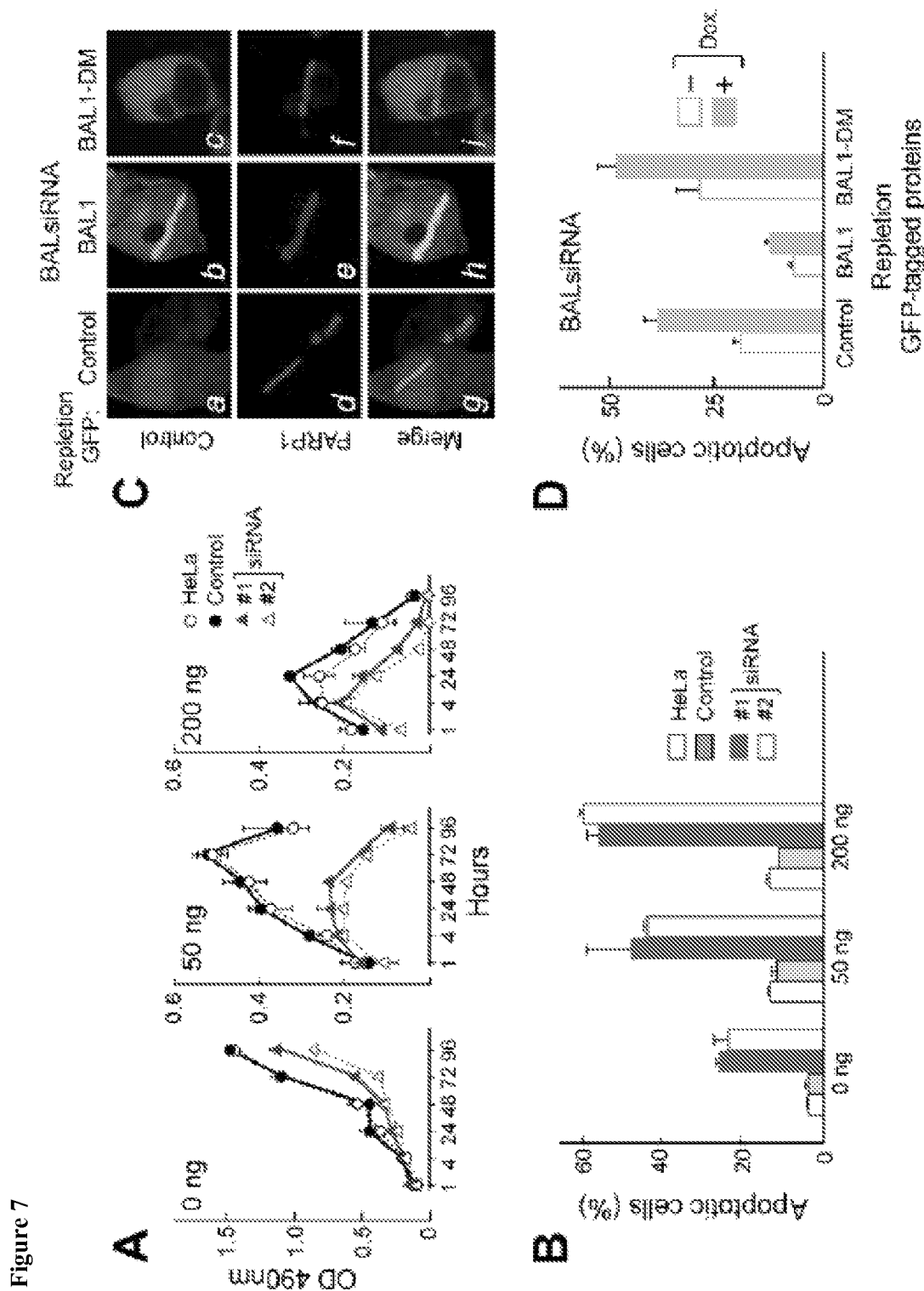
FIGS. 7A-7D show that BAL1 limits the cellular response to DNA damaging agents.
Figure 11:
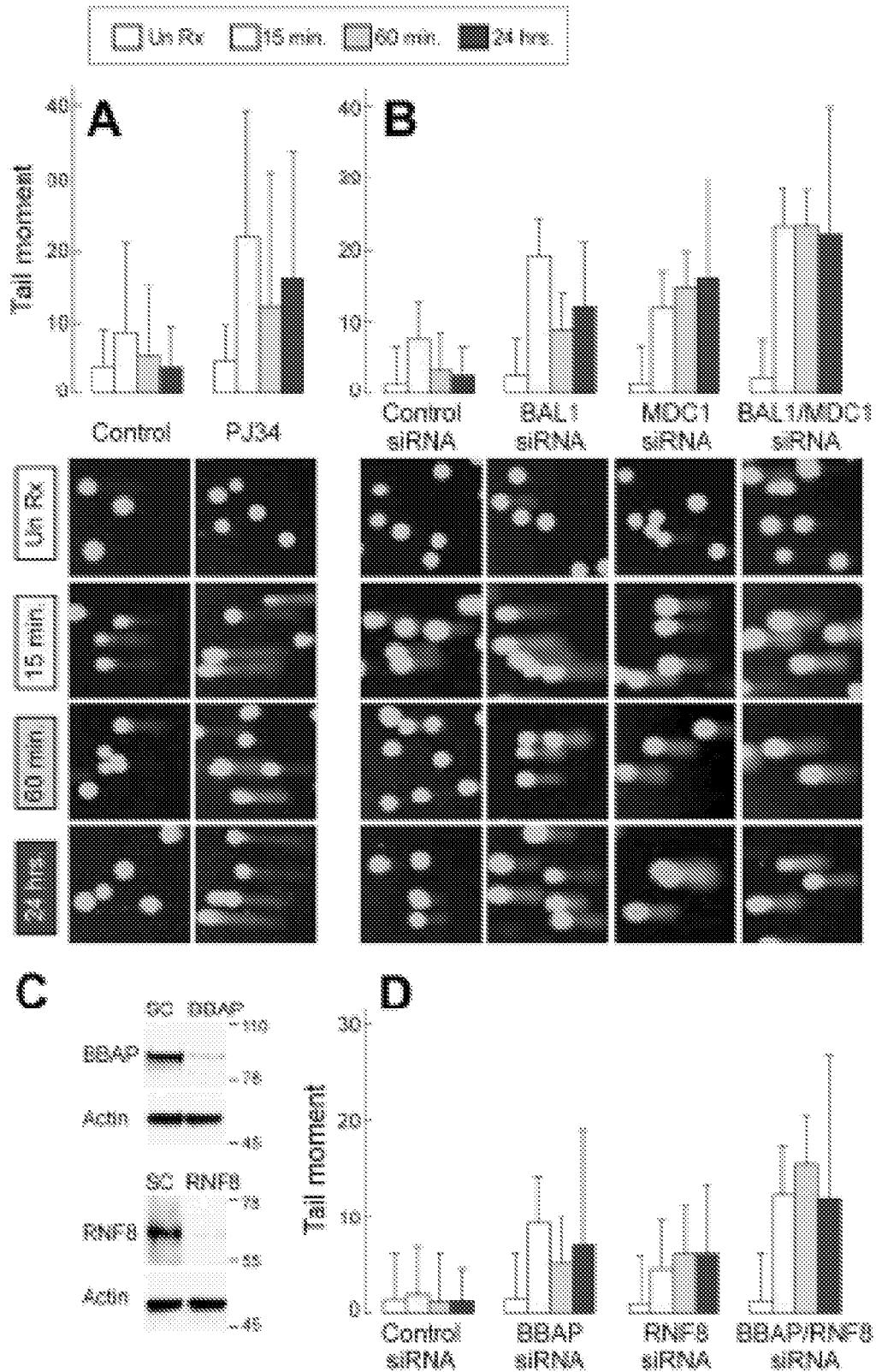
FIGS. 11A-11D show functional analyses of PARP1/BAL1/BBAP- and MDC1/RNF8-associated DDRs by comet assay. Comet assays of Hela cells pre-treated with PJ-34 or vehicle alone (FIG. 11A) or control BAL1, MDC1 or BAL1 and MDC1 siRNAs (FIG. 11B) or control, BBAP, RNF8 or BBAP and RNF8 siRNAs (FIG. 11D) treated with low-dose irradiation (200 cGy) and analyzed under alkaline conditions 15 min, 60 min or 24 hr thereafter are shown.

The present invention also defines an early wave of ubiquitylation at DNA damage sites that is dependent upon PARP1 activation, BAL1/BBAP recruitment and BBAP E3 ligase activity and independent of ATM/MDC1 and RNF8. PARP1-dependent, BAL1/BBAP-mediated ubiquitylation promotes the rapid and specific recruitment of 53BP1, RAP80 and BRCA1 to DNA damage sites. BBAP ubiquitylates histone H4 lysine 91 and increases the accessibility of H4K20 to methylation and 53BP1 recruitment via its tandem tudor domain (Yan et al. (2009) Mol. Cell. 36:110-120). BBAP-mediated ubiquitylation likely fosters RAP80/BRCA1 localization via RAP80 UIMs. Given the time course and kinetics of PARP1 activation and ATM/MDC1 phosphorylation, these studies define separate and complementary pathways of BBAP- and RNF8/RNF168-mediated ubiquitylation and recruitment of 53BP1 and BRCA1 to DNA damage sites. Functional analyses confirm the non-redundant role of PARP1-dependent BAL1/BBAP recruitment and ubiquitylation on DDR (FIGS. 7 and 11).

The roles of BAL1 and BBAP in PARP1-dependent DNA damage repair have additional clinical implications. The BAL1 macro protein and its partner E3 ligase were originally identified in a screen for genes that were overexpressed in treatment-resistant lymphomas. The results presented herein provide a mechanistic basis for the earlier observations and suggest that targeted inhibition of BAL1 and/or BBAP may increase the efficacy of chemotherapy (doxorubicin) or radiation treatment. It has been determined herein that a direct link exists between PARP1 activation and BRCA1 recruitment and BAL1 macro protein and BBAP E3 ligase are implicated in these processes.

Example 12: BAL1 and BBAP Form a Complex Via Specific Interaction Domains

Figure 16:
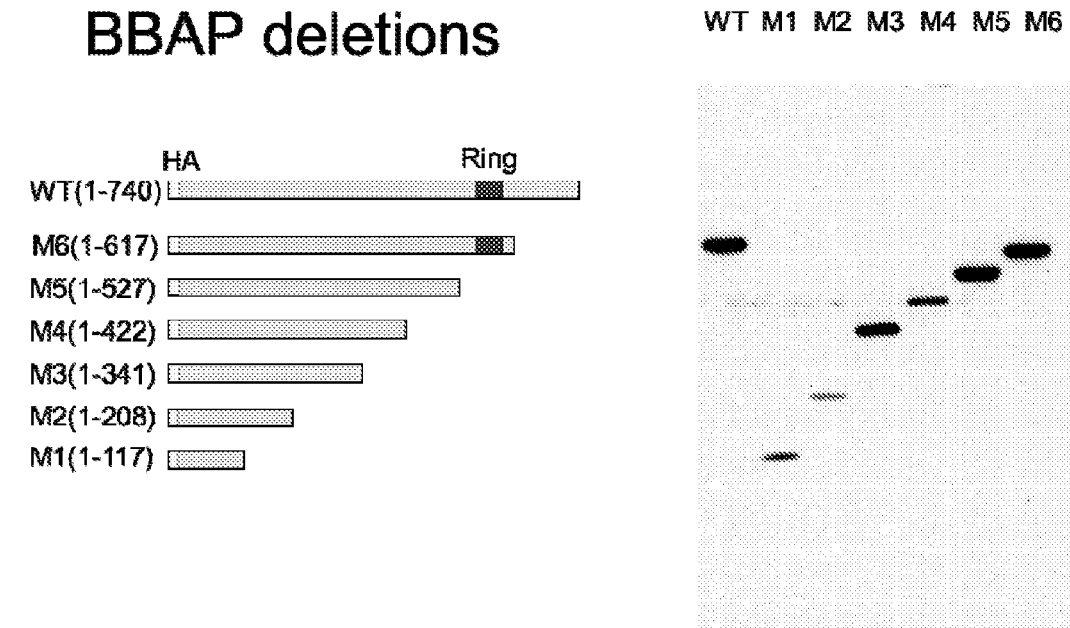
FIG. 16 shows a schematic view of several BBAP deletion constructs.
Figure 17:
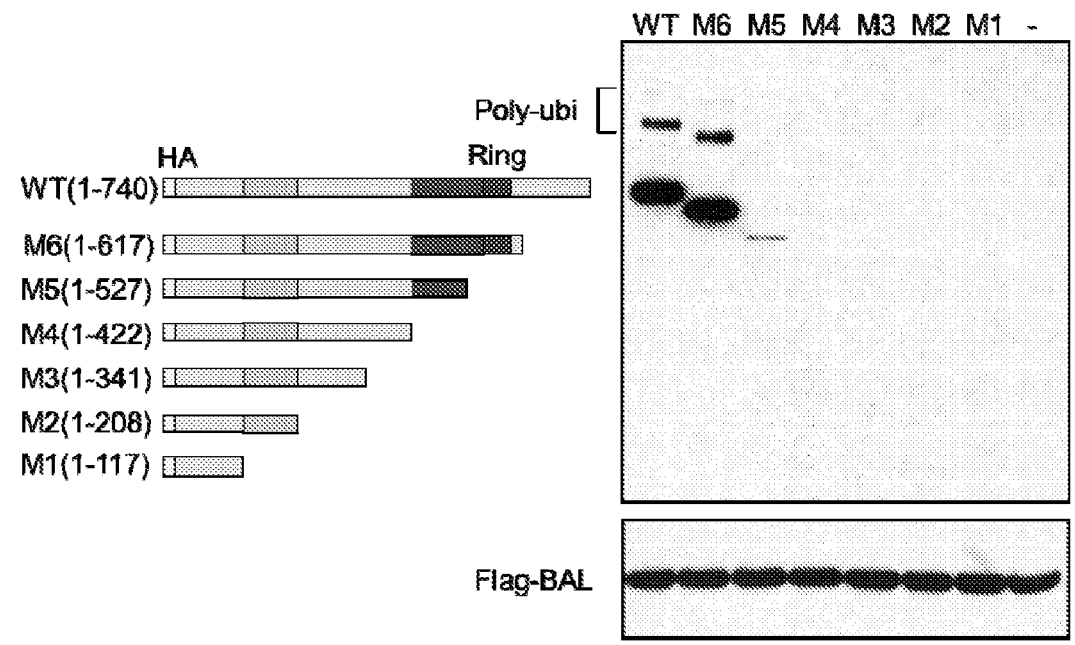
FIG. 17 shows a schematic view of BBAP's BAL1 binding domain based on the results of co-immunoprecipitation experiments.
Figure 18:
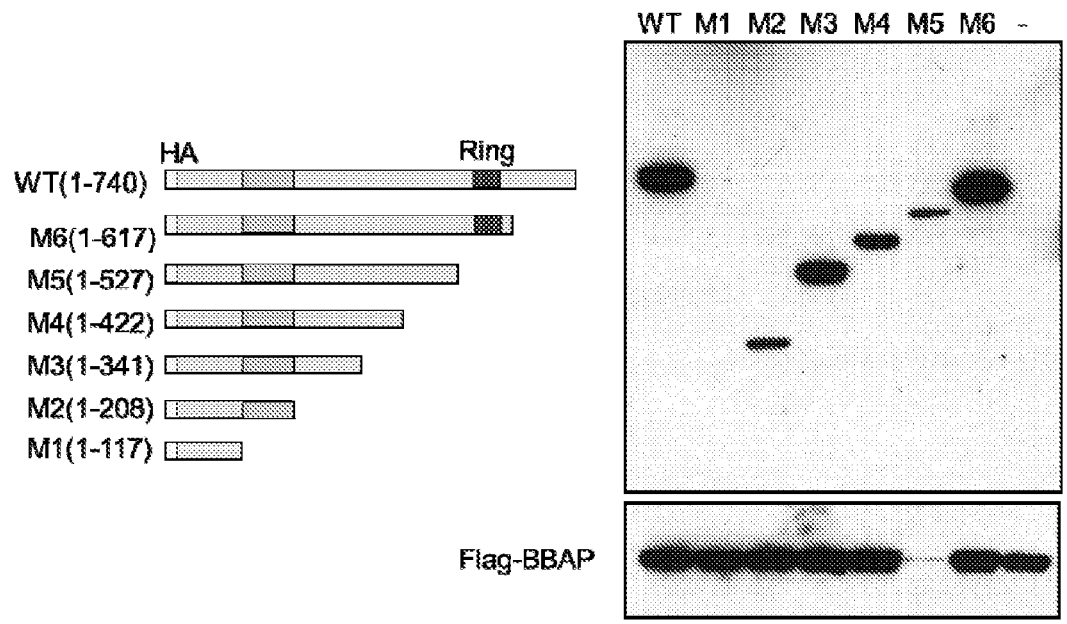
FIG. 18 shows a schematic view of BBAP's homodimerization domain based on the results of co-immunoprecipitation experiments.
Figure 19:
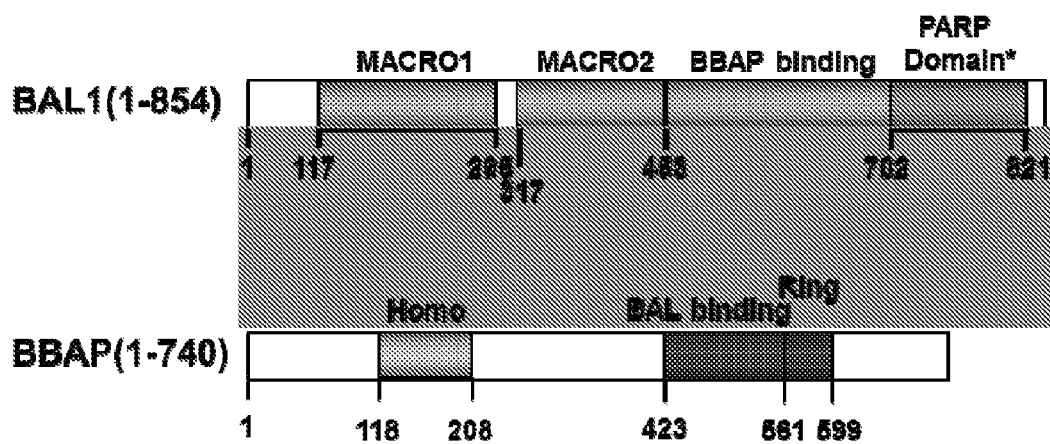
FIG. 19 shows a schematic view of the domain structures of BAL1 and BBAP, as well as the BBAP- and BAL1-interacting domains of the respective proteins.

In order to determine the protein domains necessary for BAL1 and BBAP to interact, BBAP deletion constructs and BAL1 deletion constructions were systematically generated. FIG. 16 shows a schematic view of several BBAP deletion constructs and FIG. 17 shows a schematic view of BBAP's BAL1 binding domain based on co-immunoprecipitation experiments. Similar co-immunoprecipitation experiments were conducted in order to map BBAP's homodimerization domain (FIG. 18), as well as the BBAP binding domain of BAL1 (Example 4). A schematic diagram summarizing and annotating the domain structures of BAL1 and BBAP, as well as the BBAP- and BAL1-interacting domains of the respective proteins, is shown in FIG. 19.

Figure 20:
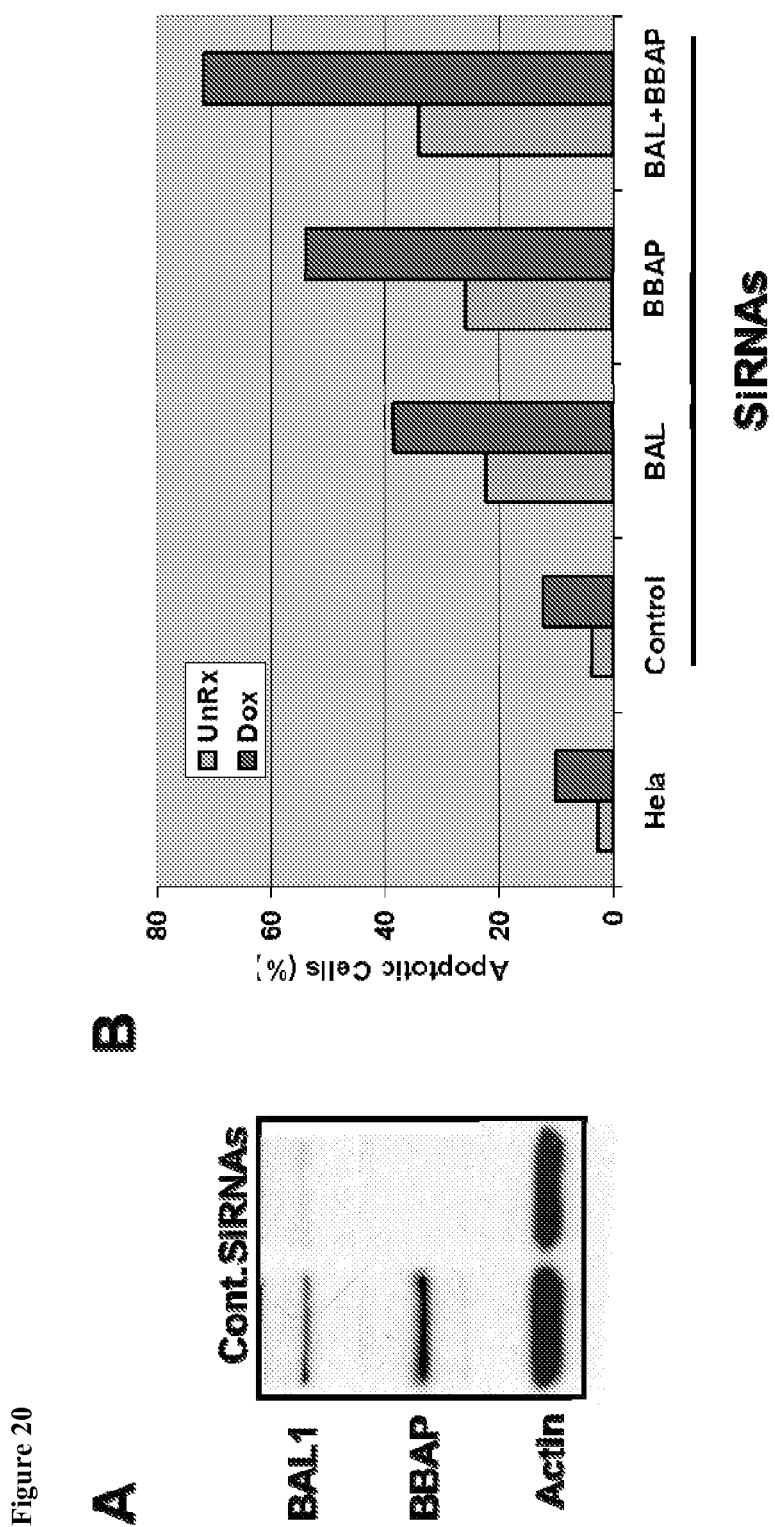
FIG. 20 shows the results of siRNA-mediated double knockdown of BAL1 and BBAP on apoptosis and chemotherapeutic sensitivity of HeLa cells.

Example 13: Double Knockdown of BAL1 and BBAP Increases Induction of Apoptosis in Cancer Cells and Increases the Sensitivity of Cancer Cells to Chemotherapeutic Agents Double knockdown of BAL1 and BBAP using siRNA-mediated depletion techniques described in Example 2 were performed to determine whether simultaneously reducing the expression of both BAL1 and BBAP increases the induction of apoptotic cells and sensitivity of cells to doxorubicin treatment of the HeLa cell line. FIG. 20 demonstrates that double knockdown of BAL1 and BBAP increases induction of apoptosis in cancer cells and increases the sensitivity of cancer cells to chemotherapeutic agents.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of treating diffuse large B-cell lymphoma by enhancing the efficacy of PARP-1 inhibitor therapy in a subject, comprising administering to the subject an effective amount of (a) an RNA interfering agent that inhibits expression of BAL1 comprising SEQ ID NOs: 1, 3, or 5, and/or an RNA interfering agent that inhibits expression of BBAP comprising SEQ ID NO: 9, and (b) the PARP-1 inhibitor therapy, wherein the RNA interfering agent is an siRNA molecule and/or an shRNA molecule that inhibits expression of the BAL1 and/or BBAP.

2. The method of claim 1, wherein the efficacy of treatment is measured by at least one criteria selected from the group consisting of survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

3. The method of claim 1, wherein the subject is a human.

4. A method of enhancing the efficacy of PARP-1 inhibitor therapy in inhibiting hyperproliferation of a hyperproliferative diffuse large B-cell lymphoma cell in a medium, comprising applying to said medium an effective amount of (a) an RNA interfering agent that inhibits expression of BAL1 comprising SEQ ID NOs: 1, 3, or 5, and/or BBAP comprising SEQ ID NO: 9, and (b) the PARP-1 inhibitor therapy, wherein the RNA interfering agent is an siRNA molecule and/or an shRNA molecule that inhibits expression of the BAL1 and/or BBAP.

5. The method of claim 4, wherein the cells are human cells.

6. The method of claim 1, comprising administering an siRNA molecule that inhibits expression of BAL1 comprising SEQ ID NOs: 1, 3, or 5.

7. The method of claim 1, comprising administering an shRNA molecule that inhibits expression of BAL1 comprising SEQ ID NOs: 1, 3, or 5.

8. The method of claim 1, comprising administering an siRNA molecule that inhibits expression of BBAP comprising SEQ ID NO: 9.

9. The method of claim 1, comprising administering an shRNA molecule that inhibits expression of BBAP comprising SEQ ID NO: 9.

10. The method of claim 4, comprising administering an siRNA molecule that inhibits expression of BAL1 comprising SEQ ID NOs: 1, 3, or 5.

11. The method of claim 4, comprising administering an shRNA molecule that inhibits expression of BAL1 comprising SEQ ID NOs: 1, 3, or 5.

12. The method of claim 4, comprising administering an siRNA molecule that inhibits expression of BBAP comprising SEQ ID NO: 9.

13. The method of claim 4, comprising administering an shRNA molecule that inhibits expression of BBAP comprising SEQ ID NO: 9.

* * * * *